US009802185B2

(12) United States Patent
Eastham et al.

(10) Patent No.: US 9,802,185 B2
(45) Date of Patent: Oct. 31, 2017

(54) CATALYST SYSTEM

(71) Applicant: Lucite International UK Limited, Southampton (GB)

(72) Inventors: Graham Eastham, Redcar (GB); Neil Tindale, Redcar (GB)

(73) Assignee: LUCITE INTERNATIONAL UK LIMITED, Southhampton (GB)

( * ) Notice: Subject to any disclaimer, the term of this patent is extended or adjusted under 35 U.S.C. 154(b) by 58 days.

(21) Appl. No.: 14/682,656

(22) Filed: Apr. 9, 2015

(65) Prior Publication Data

US 2015/0321186 A1 Nov. 12, 2015

Related U.S. Application Data

(62) Division of application No. 10/589,971, filed as application No. PCT/GB2005/000569 on Feb. 17, 2005, now Pat. No. 9,040,445.

(30) Foreign Application Priority Data

Feb. 18, 2004 (GB) .................................. 0403592.9

(51) Int. Cl.
C07C 51/14 (2006.01)
C07C 67/38 (2006.01)
B01J 31/22 (2006.01)
B01J 31/24 (2006.01)
B01J 31/02 (2006.01)
B01J 31/18 (2006.01)

(52) U.S. Cl.
CPC ....... B01J 31/2433 (2013.01); B01J 31/0225 (2013.01); B01J 31/1895 (2013.01); B01J 31/2295 (2013.01); B01J 31/24 (2013.01); B01J 31/2457 (2013.01); B01J 31/2485 (2013.01); C07C 51/14 (2013.01); C07C 67/38 (2013.01); B01J 2231/321 (2013.01); B01J 2531/0205 (2013.01); B01J 2531/80 (2013.01); B01J 2531/824 (2013.01); B01J 2531/842 (2013.01)

(58) Field of Classification Search
CPC .......... C07C 67/38; C07C 51/14; C07C 69/24
See application file for complete search history.

(56) References Cited

U.S. PATENT DOCUMENTS

| | | |
|---|---|---|
| 2,504,049 A | 4/1950 | Richards |
| 3,131,204 A | 4/1964 | Sisler et al. |
| 3,564,020 A | 2/1971 | Fenton |
| 3,962,074 A | 6/1976 | Schropp |
| 3,968,153 A | 7/1976 | Ohrui et al. |
| 4,142,058 A | 2/1979 | Matsumura et al. |
| 4,245,115 A | 1/1981 | Butter |
| 4,377,708 A | 3/1983 | Morris |
| 4,500,727 A | 2/1985 | Kitamura et al. |
| 4,504,684 A | 3/1985 | Fox et al. |
| 4,517,061 A | 5/1985 | Fauvarque |
| 4,555,557 A | 11/1985 | Fukumoto et al. |
| 4,786,443 A | 11/1988 | Drent et al. |
| 4,792,620 A * | 12/1988 | Paulik .................. B01J 31/0231 560/232 |
| 4,818,810 A | 4/1989 | Drent |
| 4,835,250 A | 5/1989 | Drent |
| 4,868,282 A | 9/1989 | Van Broekhoven et al. |
| 4,879,412 A | 11/1989 | Iwasaki et al. |
| 4,880,903 A | 11/1989 | Van Broekhoven et al. |
| 4,900,413 A | 2/1990 | Tanaka et al. |
| 4,950,703 A | 8/1990 | Smutny |
| 4,956,493 A | 9/1990 | Ueoka et al. |
| 4,960,926 A | 10/1990 | Drent |
| 4,960,949 A | 10/1990 | Devon et al. |
| 5,028,576 A | 7/1991 | Drent et al. |
| 5,099,062 A | 3/1992 | Drent et al. |
| 5,103,043 A | 4/1992 | Drent et al. |
| 5,149,868 A | 9/1992 | Drent |
| 5,158,921 A | 10/1992 | Drent et al. |
| 5,166,116 A | 11/1992 | Drent et al. |
| 5,177,253 A | 1/1993 | Drent et al. |
| 5,179,225 A | 1/1993 | Drent et al. |

(Continued)

FOREIGN PATENT DOCUMENTS

| | | |
|---|---|---|
| AU | 2003259322 A1 | 2/2004 |
| AU | 2006314268 A1 | 5/2007 |

(Continued)

OTHER PUBLICATIONS

White et al, Basic Energy Sciences Advisory Committee Subpanel Workshop Report, Opportunities for Catalysis in the 21st Century, 2002, pp. 1-47.*
Doherty et al, Journal of Organometallic Chemistry, Selectivity for Methoxycarbonylation of Ethylene Versus Co-Ethylene Copolymerization with Catalysts Based on C4-bridged Bidentate Phosphines and Phospholes, 2001, 640, pp. 182-196.*
Office Action issued in U.S. Appl. No. 13/516,176 dated Jan. 22, 2016.
Office Action issued in U.S. Appl. No. 12/517,215 dated Jan. 4, 2016.
Notice of Allowance issued in U.S. Appl. No. 12/084,575 dated Jan. 14, 2016.
Abbenhuis et al., "Successful Application of a "Forgotten" Phosphine in Asymmetric Catalysis: A 9-Phosphabicyclo[3.3.1]non-9-yl Ferrocene Derivative as a Chiral Ligand," Organometallics, vol. 14, pp. 759-766, 1995.

(Continued)

Primary Examiner — Paul A Zucker
(74) Attorney, Agent, or Firm — Venable LLP; Keith G. Haddaway; Annette K. Kwok

(57) ABSTRACT

The present invention provides a catalyst system capable of catalyzing the carbonylation of an ethylenically unsaturated compound, which system is obtainable by combining:
a) a metal of Group VIB or Group VIIIB or a compound thereof,
b) a bidentate phosphine, arsine or stibine ligand, and
c) an acid,
wherein the ligand is present in at least a 2:1 molar excess compared to the metal or the metal in the metal compound, and that the acid is present in at least a 2:1 molar excess compared to the ligand, a process for the carbonylation of an ethylenically unsaturated compound, a reaction medium, and use of the system.

22 Claims, 3 Drawing Sheets

(56) References Cited

U.S. PATENT DOCUMENTS

| | | | |
|---|---|---|---|
| 5,189,003 A | 2/1993 | Klusener et al. |
| 5,196,578 A | 3/1993 | Kuragano et al. |
| 5,210,280 A | 5/1993 | Drent |
| 5,245,098 A | 9/1993 | Hamilton et al. |
| 5,246,558 A | 9/1993 | Chevigne et al. |
| 5,258,546 A | 11/1993 | Klusener et al. |
| 5,350,876 A | 9/1994 | Drent et al. |
| 5,369,074 A | 11/1994 | Drent |
| 5,436,356 A | 7/1995 | Drent et al. |
| 5,563,308 A | 10/1996 | Spindler et al. |
| 5,565,594 A | 10/1996 | Spindler et al. |
| 5,612,417 A | 3/1997 | Rhein et al. |
| 5,618,983 A | 4/1997 | Burke |
| 5,710,344 A | 1/1998 | Breikss et al. |
| 5,719,313 A | 2/1998 | Drent et al. |
| 5,760,264 A | 6/1998 | Brieden |
| 5,773,661 A | 6/1998 | Unruh et al. |
| 5,783,715 A | 7/1998 | Pugin |
| 5,962,732 A | 10/1999 | Burke |
| 6,015,919 A | 1/2000 | Pugin |
| 6,156,934 A | 12/2000 | Suykerbuyk et al. |
| 6,169,192 B1 | 1/2001 | Pugin et al. |
| 6,191,284 B1 | 2/2001 | Knochel et al. |
| 6,232,262 B1 | 5/2001 | Sielcken et al. |
| 6,258,979 B1 | 7/2001 | Kagan et al. |
| 6,284,919 B1 | 9/2001 | Pearson et al. |
| 6,284,925 B1 | 9/2001 | Knochel et al. |
| 6,307,065 B1 | 10/2001 | Tjaden et al. |
| 6,335,471 B1 | 1/2002 | Eastham et al. |
| 6,337,406 B1 | 1/2002 | Zhang |
| 6,348,621 B1 * | 2/2002 | Wang ............ B01J 31/1875 560/232 |
| 6,391,818 B1 | 5/2002 | Bonsel et al. |
| 6,462,095 B1 | 10/2002 | Bonsel et al. |
| 6,476,255 B1 | 11/2002 | Hadden et al. |
| 6,521,769 B1 | 2/2003 | Zhang |
| 6,706,912 B2 | 3/2004 | Drent et al. |
| 6,723,882 B2 | 4/2004 | Slany et al. |
| 6,737,542 B1 | 5/2004 | Drent et al. |
| 6,743,911 B2 | 6/2004 | Drent et al. |
| 6,753,450 B2 | 6/2004 | Ahlers et al. |
| 6,844,463 B2 | 1/2005 | Slany et al. |
| 6,916,954 B2 | 7/2005 | Schafer et al. |
| 6,982,357 B2 | 1/2006 | Crabtree et al. |
| 6,984,668 B1 | 1/2006 | Eastham et al. |
| 7,026,473 B2 | 4/2006 | Drent et al. |
| 7,129,367 B2 | 10/2006 | Suzuki et al. |
| 7,148,176 B2 | 12/2006 | Beller et al. |
| 7,265,240 B2 | 9/2007 | Eastham et al. |
| 7,371,705 B2 | 5/2008 | Eastham et al. |
| 7,629,470 B2 | 12/2009 | Campos et al. |
| 8,604,236 B2 | 12/2013 | Eastham et al. |
| 9,040,445 B2 | 5/2015 | Eastham et al. |
| 2001/0044556 A1 | 11/2001 | Drent et al. |
| 2001/0051745 A1 | 12/2001 | Pearson et al. |
| 2002/0016484 A1 | 2/2002 | Drent et al. |
| 2002/0045748 A1 | 4/2002 | Drent et al. |
| 2003/0191339 A1 | 10/2003 | Schfer et al. |
| 2004/0110989 A1 | 6/2004 | Slany et al. |
| 2004/0115475 A1 | 6/2004 | Hashimoto |
| 2004/0162440 A1 | 8/2004 | Bunel et al. |
| 2005/0090694 A1 | 4/2005 | Drent et al. |
| 2006/0106259 A1 | 5/2006 | Eastham et al. |
| 2006/0122435 A1 | 6/2006 | Eastham et al. |
| 2006/0128985 A1 | 6/2006 | Eastham et al. |
| 2006/0235241 A1 | 10/2006 | Drent et al. |
| 2006/0252935 A1 | 11/2006 | Eastham et al. |
| 2008/0051475 A1 | 2/2008 | Eastham et al. |
| 2008/0086015 A1 | 4/2008 | Eastham |
| 2008/0269459 A1 | 10/2008 | Drent et al. |
| 2008/0269520 A1 | 10/2008 | Drent et al. |
| 2009/0163724 A1 | 6/2009 | Eastham et al. |
| 2009/0216041 A1 | 8/2009 | Eastham et al. |
| 2009/0234126 A1 | 9/2009 | Hartwig et al. |
| 2009/0312561 A1 | 12/2009 | Eastham et al. |
| 2010/0030036 A1 | 2/2010 | Mottram et al. |
| 2010/0113255 A1 | 5/2010 | Eastham et al. |
| 2010/0197958 A1 | 8/2010 | Eastham et al. |
| 2010/0273970 A1 | 10/2010 | Koestner et al. |
| 2010/0324332 A1 | 12/2010 | Carrington-Smith et al. |
| 2011/0287991 A1 | 11/2011 | Dubois |
| 2012/0010413 A1 | 1/2012 | Abrecht et al. |
| 2012/0309911 A1 | 12/2012 | Johnson et al. |

FOREIGN PATENT DOCUMENTS

| | | |
|---|---|---|
| BR | PI 9000965 A | 2/1991 |
| BR | 9510249-3 | 11/1997 |
| BR | PI 0109239 A | 12/2002 |
| BR | PI 0313289-7 A | 7/2005 |
| CA | 2498293 A1 | 3/2004 |
| CN | 1171098 A | 1/1998 |
| CN | 1429228 A | 7/2003 |
| CN | 1478071 A | 2/2004 |
| CN | 101137611 A | 3/2008 |
| CN | 101142162 A | 3/2008 |
| DE | 19745904 A1 | 4/1999 |
| DE | 19754304 A1 | 6/1999 |
| DE | 10023470 A1 | 11/2001 |
| DE | 10037961 A1 | 2/2002 |
| EP | 0055875 A1 | 7/1982 |
| EP | 0106379 A1 | 4/1984 |
| EP | 121965 A2 | 10/1984 |
| EP | 0144118 A1 | 6/1985 |
| EP | 181014 A1 | 5/1986 |
| EP | 213671 A1 | 3/1987 |
| EP | 0 227 160 A2 | 7/1987 |
| EP | 0235864 A1 | 9/1987 |
| EP | 0274795 A2 | 7/1988 |
| EP | 0282142 A1 | 9/1988 |
| EP | 0305089 A1 | 3/1989 |
| EP | 0375573 A1 | 6/1990 |
| EP | 0386833 A1 | 9/1990 |
| EP | 0441447 A1 | 8/1991 |
| EP | 0489472 A2 | 6/1992 |
| EP | 0 495 548 A2 | 7/1992 |
| EP | 0495347 A1 | 7/1992 |
| EP | 0495348 A1 | 7/1992 |
| EP | 0495547 A2 | 7/1992 |
| EP | 0 499 329 A1 | 8/1992 |
| EP | 0577205 A2 | 1/1994 |
| EP | 0683764 A1 | 11/1995 |
| EP | 0728733 A1 | 8/1996 |
| EP | 0879642 A2 | 11/1998 |
| EP | 1330309 A1 | 7/2003 |
| FR | 2034147 A5 | 12/1970 |
| GB | 2006208 A | 5/1979 |
| GB | WO 98/41495 A1 * | 10/1998 |
| JP | 6216737 A | 1/1987 |
| JP | 04-215851 A | 8/1992 |
| JP | H0558949 A | 3/1993 |
| JP | 06-065148 A | 3/1994 |
| JP | 08134218 A | 5/1996 |
| JP | 10-511034 A | 10/1998 |
| JP | 10 339929 A | 12/1998 |
| JP | 2001-517218 A | 10/2001 |
| JP | 2003-527365 A | 9/2003 |
| JP | 2003-528849 A | 9/2003 |
| JP | 2004-509741 A | 4/2004 |
| JP | 2004-515487 A | 5/2004 |
| JP | 2004-515537 A | 5/2004 |
| JP | 2005-535455 A | 11/2005 |
| JP | 2005-535695 A | 11/2005 |
| JP | 2007-502315 A | 2/2007 |
| JP | 2007-524700 A | 8/2007 |
| JP | 2008-505903 A | 2/2008 |
| JP | 2009-504620 A | 2/2009 |
| JP | 2009-515936 A | 4/2009 |
| JP | 2009-533409 A | 9/2009 |
| JP | 2010511600 A | 4/2010 |
| JP | 2013063440 A | 4/2013 |
| JP | 2013-091651 A | 5/2013 |
| JP | 5198267 B2 | 5/2013 |
| JP | 2013-147503 A | 8/2013 |

(56) References Cited

FOREIGN PATENT DOCUMENTS

| | | |
|---|---|---|
| JP | 5350592 B2 | 11/2013 |
| JP | 2014-208649 A | 11/2014 |
| KR | 2000-0076427 | 12/2000 |
| KR | 20050084042 A | 8/2005 |
| KR | 10-0851423 B1 | 8/2008 |
| TW | 524801 B | 3/2003 |
| TW | 552257 B | 9/2003 |
| TW | 200416212 | 9/2004 |
| TW | 200404773 | 4/2010 |
| TW | I410280 B | 10/2013 |
| WO | WO-96/19434 A1 | 6/1996 |
| WO | WO-97/08124 A1 | 3/1997 |
| WO | WO-97/40001 A1 | 10/1997 |
| WO | WO-98/41495 A1 | 9/1998 |
| WO | WO-98/42717 A1 | 10/1998 |
| WO | WO-98/45040 A1 | 10/1998 |
| WO | WO-99/47528 A1 | 9/1999 |
| WO | WO-00/56695 A1 | 9/2000 |
| WO | WO-01/10551 A1 | 2/2001 |
| WO | WO-01/28972 A1 | 4/2001 |
| WO | WO-01/38336 A1 | 5/2001 |
| WO | WO-01/65583 A1 | 9/2001 |
| WO | WO-01/70659 A1 | 9/2001 |
| WO | WO-0168583 A2 | 9/2001 |
| WO | WO-01/72697 A2 | 10/2001 |
| WO | WO-01/85662 A2 | 11/2001 |
| WO | WO-0187899 A1 | 11/2001 |
| WO | WO-02/12161 A1 | 2/2002 |
| WO | WO-02/46143 A1 | 6/2002 |
| WO | WO-02/48094 A1 | 6/2002 |
| WO | WO-03/040159 A2 | 5/2003 |
| WO | WO-03/070370 A1 | 8/2003 |
| WO | WO-2004/014552 A1 | 2/2004 |
| WO | WO-2004/014834 A1 | 2/2004 |
| WO | WO-2004/024322 A2 | 3/2004 |
| WO | WO-2004/028689 A2 | 4/2004 |
| WO | WO-2004/050599 A1 | 6/2004 |
| WO | WO-2004050599 A1 | 6/2004 |
| WO | WO-2004/072088 A2 | 8/2004 |
| WO | WO-2004/103948 A1 | 12/2004 |
| WO | WO-2005/003070 A1 | 1/2005 |
| WO | WO-2005/079981 A1 | 9/2005 |
| WO | WO-2005/082830 A1 | 9/2005 |
| WO | WO-2005/118519 A1 | 12/2005 |
| WO | WO-2006/062467 A1 | 6/2006 |
| WO | WO-2006/084892 A2 | 8/2006 |
| WO | WO-2007/020379 A1 | 2/2007 |
| WO | WO-2007109365 A2 | 9/2007 |
| WO | WO-2007/119079 A1 | 10/2007 |
| WO | WO-2007119079 A1 | 10/2007 |
| WO | WO-2008/031750 A2 | 3/2008 |
| WO | WO-2008/065448 A1 | 6/2008 |
| WO | WO-2008/075108 A1 | 6/2008 |
| WO | WO-2008145976 A1 | 12/2008 |
| WO | WO-2009010782 A1 | 1/2009 |

OTHER PUBLICATIONS

Andrews et al. "Regioselective complexation of unprotected carbohydrates by Platinum(II); Synthesis, structure, complexation equilibria, and hydrogen-bonding in carbonate-derived bis(phosphine)platinum(II) diolate and alditolate complexes", Journal of American Chemical Society, No. 116, pp. 5730-5740, (1994).
Andrews et al. "Syntheses, spectra and structures of (diphosphine)platinum(II) carbonate complexes" Inorganic Chemistry, No. 35, pp. 5478-5483, (1996).
Argouarch, et al., "Synthesis of Some Ferrocene-Based 1,3(phosphanes) with Planar Chirality as the Sole Source of Chirality", European J of Organic Chemistry, 2000, vol. 16 pp. 2885-2891.
Armor, "Perspective: Do you really have a better catalyst?," Applied Catalysis A: General, vol. 282, pp. 1-4, 2005.
Becker et al. "Imprinting chiral information into rigidified dendrimers", Organometallics, No. 22, pp. 4984-4998, (2003).

Becker et al. "Synthesis and characterization of chiral diphosphine platinum(II) VANOL and Vapol complexes", Organometallics, No. 22, pp. 3245-3249, (2003).
Bellabarba et al., "Synthesis, X-ray characterization and reactions of a trigonal planar palladium()) carbonyl complex", Chemical Communications, No. 15, pp. 1916-1917, (2003).
Brauer et al., "Reactions of coordinated ligands. XIV. Synthesis of a tetradentate phosphorus macrocycle in a palladium (II) template", Chemische Berichte, vol. 119, No. 1, pp. 349-365 (1986).
Brunkan et al. "Effect of chiral cavities associated with molecularly imprinted platinum centers on the selectivity of ligand-exchange reactions at platinum", Journal of American Chemical Society, No. 22, pp. 6217-6225, (2000).
Brunkan et al. "Unorthodox C,O binding mode of Me2BINOL in Pt(II) complexes", Journal of American Chemical Society, No. 120, pp. 11002-11003, (1998).
Cecconi et al. "Palladium complexes with the tripodal phosphine tris(2-diphenylphosphinoethyl)amine. Synthesis and structure of trigonal, tetrahedral, trigonal bipyramidal, and square planar complexes", J. Chem. Soc. Dalton Trans., iss. 1, pp. xvii-xx, 1989.
Clegg et al, "Highly active and selective catalysts for the production of methyl propanoate via the methoxycarbonylation of ethene," Chem. Commun., pp. 1877-1878 (1999).
Clegg et al., "Characterisation and dynamics of [Pd(L-L)H(solv)]+, [Pd(L-L(CH2CH3)]+ and [Pd(L-L)(C(0)Et)(THF)]+ (L-L=1,2-(CH2PBut2)2C6H4): key intermediates in the catalytic methoxycarbonylation of ethane to methylpropanoate", Organometallics, vol. 21, No. 9, pp. 1832-1840 (2002).
Clegg et al., "Synthesis and reactivity of palladium hydrido-solvento complexes, including a key intermediate in the catalytic methoxycarbonylation of ethane to methypropanoate", Journal of the Chemical Society, Dalton Transactions, No. 17, pp. 3300-3308 (2002).
Corrected Notice of Allowability issued in U.S. Appl. No. 10/589,971 dated Mar. 24, 2015.
Cullen et al., "Structure of the Hydrogenation Catalyst [(PP)Rh(NBD)]ClO4, (PP)=(η5- [(CH3)3C]2PC5H4)2Fe, and Some Comparative Rate Studies," Organometallics, vol. 2, pp. 714-719, 1983.
Dias et al., "Synthesis and characterization of .eta.5-monocyclopentadienyl (p-nitrobenzonitrile)ruthenium(II) salts: second harmonic generation powder efficiencies", Journal of Organometallic Chemistry, vol. 475, No. 1-2, pp. 241-245 (1994).
Doherty et al., "Selectivity for the methoxycarbonylation of ethylene versus Co-ethylene copolymerization with catalysts based on C4-bridged bidentate phosphines and phospholes," Journal of Organometallic Chemistry, vol. 640, pp. 182-196, 2001.
Dörwald, Side Reactions in Organic Synthesis: A Guide to Successful Synthesis Design, Weinheim—Wiley-VCH, pp. ix, 1-16, 2005.
Edelbach et al., "Catalytic hydrogenolysis of biphenylene with platinum, palladium, and nickelphosphine complexes", Organometallics, vol. 17, No. 22, pp. 4784-4794 (1998).
Godard, et al., "Systematic Study of the Asymmetric Methoxycarbonylation of Styrene Catalyzed by Palladium Systems Containing Chiral Ferrocenyl Diphosphine Ligands", Helvetica Chimica Acta, 2006 vol. 89(8) pp. 1610-1622.
Gray et al., "The Di-t-Butylphosphinyl Directed ortho Metalation Group, Synthesis of Hindered Dialkylarylphosphines," Synlett Letters, vol. 4, pp. 422-424 (1998).
Grimmer, et al., "Zirconium bis-cyclopentadienyl compounds: An investigation into the influence of substituent effects on the ethene polymerisation behaviour of (CpR)2ZrCl2/MAO catalysts," Journal of Molecular Catalysis A: Chemical, vol. 188, No. 1-2, pp. 105-113, 2002.
Hagen, "Industrial Catalysis: A Practical Approach," pp. v-xvii and 1-6, 2006.
Hartley, Supported Metal Complexes: A New Generation of Catalysts, Section 1.3, pp. 1, 9, 1985.
Hartwig, et al. "Structure and reactions of oxametallacyclobutanes and oxametallacyclobutenes of ruthenium", Organometallics, vol. 10, No. 9, pp. 3344-3362 (1991).

(56) References Cited

OTHER PUBLICATIONS

Hayward et al. "Some reactions of peroxobis(triphenylphosphine)platinum(II) and analogs with carbon dioxide, carbon disulfide, and other unsaturated molecules", Journal of American Chemical Society, vol. 92, issue 20, pp. 5873-5878, (1970).
Hofmann et al., "Bis(Di-T-Butylphosphino)Methane complexes of Rhodium: Homogeneous Alkyne Hydrosilation by Catalyst-Dependent Aklyne Insertion into Rh-Si or Rh-H Bonds. Molecular Structure of the Dimer [(dtbpm) RHcL]2 and of the Silyl Complex (dtbpm) Rh[Si(OEt)3](PMe3)", Journal of Organometallic Chemistry, vol. 490, 1995, pp. 51-70.
Imwinkelried, "Catalytic Asymmetric Hydrogenation in the Manufacture of d-Biotin and Dextromethorphan," NSCS Spring Meeting 97: Industrial Asymmetric Synthesis, Chimia 51 (1997) 300-302.
International Preliminary Report on Patentability issued in Application No. PCT/GB2010/052093 dated Jun. 28, 2012.
International Search Report issued in International Application No. PCT/GB2007/050717 dated Mar. 30, 2007.
International Search Report issue in GB0716530.1 dated Jan. 30, 2008.
International Search Report issued in International Application No. PCT/GB2009/050780 dated Oct. 15, 2009.
International Search Report issued in International Application No. PCT/GB2010/052093 dated Apr. 8, 2011.
International Search Report issued in International Application No. PCT/GB2010/052214 dated Mar. 30, 2011.
Jones et al, "Rhodium-Catalyzed Activation and Functionalization of the C—C Bond of Biphenylene", Organometallics, vol. 20, 2001, pp. 5745-5750.
Kim et al., "Synthesis and theoretical study of palladium (II) complexes with aminophosphines as 7-membered chelate rings", Bulletin KR Chem. Society, vol. 18, No. 11, pp. 1162-1166 (1997).
Kirk Othmer Encyclopaedia of Chemical Terminology, vol. 9, 4th Ed., p. 783, Hydrolysis of Organic Esters, pp. 783-85 and 87, John Wiley & Sons, Jan. 1994.
Kiss, "Palladium-catalyzed Reppe Carbonylation," Chem. Rev. 2001, 101(11): 3435 (Abstract Only).
Knight et al: "Remarkable Differences in Catalyst Activity and Selectivity fo rthe production of Methyl Propanoate versus Co-Ethylene Copolymer by a Series of palladium Complexes of Related C4-Bridged Diphosphines" Organometallics 2000, 19 4957-4967.
Konno et al. "Preparation and spectroscopic characteristics of geometrical isomers of bis[1,2-bis(dimethylphosphino)ethane]cobalt(III) complexes with thiolate ligands", The Chemical Society of Japan, No. 62, pp. 3475-3478, (1989).
Kraatz et al., "The reactions of tridentate cationic palladium (II) complexes with olefins and nucleophiles," the Journal of Organometallic Chemistry, vol. 488, No. 1, pp. 223-232 (1995).
Latif et al. "Square planar platinum(II) complexes, crystal structures of cis-bis(triphenylphosphine) hydro(triphenylstannyl) platinum(II) and cis-bis(triphenylphosphine) hydro(triphenylsilyl) platinum(II)", Journal of Organometallic Chemistry, No. 474, pp. 217-221, (1994).
Lee et al., "improved Catalysts for the Palladium-Catalyzed Synthesis of Oxindoles by Amide α-Arylation, Rate Acceleration, Use of Aryl Chloride Substrates, and a New Carbene Ligand for Asymmetric Transformations," J. Org. Chem, 2001, 66, 3402-3415.
Lide et al., Handbook of Chem and Phys., 76th Ed., CRC Press, 1995, p. 8-141, 6-155 to 6-177; 15-16 to 15-25.
Lindner et al., "Catakytic Activity of Cationic Diphospalladium (II)Complexes in the Alkene/Co Copolymerization in Organic Solvents and Water in Dependence on the Lgenth of the Alkyl Chain at the Phosphine Ligands", Journal of Organometallic Chemistry, vol. 602, 2000, pp. 173-187.
Machine Translation of JP 08-134218, May 28, 1996.
Masters et al. "Homogeneous Transition Metal Catalysis—A Gentle Are", C Masters, Chapman & Hall, Feb. 1981, title page, contents page and pp. 4-21.
Mikami et al. "Molecular design of DABNTf as a highly efficient resolving reagent for racemic Pd complex with tropos biphenylphosphine (BIPHEP) ligand: circular dichroism (CD) spectra of enantiopure BIPHEP-Pd complex", Chirality, No. 15, pp. 105-107, (2003).
Miskowski et al. "Preparation and spectroscopic properties of Cobalt(III) complexes containing phosphine ligands. The electronic structural description of side-bonded dioxygen", Journal of American Chemical Society, vol. 98, No. 9, pp. 2477-2483, (1976).
Molander et al., "Synthesis and application of chiral cyclopropane-based ligands in palladium-catalyzed allylic alkylation", Journal of Organic Chemistry, vol. 69, No. 23, pp. 8062-8069 (2004).
Notice of Allowance issued in U.S. Appl. No. 12/297,023 dated Dec. 26, 2012.
Notice of Allowance issued in U.S. Appl. No. 12/297,023 dated Feb. 21, 2013.
Notice of Allowance issued in U.S. Appl. No. 11/990,272 dated Jul. 25, 2013.
Notice of Allowance issued in U.S. Appl. No. 10/589,971 dated Dec. 5, 2014.
Notice of Allowance issued in U.S. Appl. No. 13/002,406 dated Apr. 9, 2014.
Notice of Allowance issued in U.S. Appl. No. 13/002,406 dated Jul. 3, 2014.
Notice of Allowance issued in U.S. Appl. No. 13/520,523 dated Jun. 23, 2014.
Notice of Allowance issued in U.S. Appl. No. 13/520,523 dated Oct. 14, 2014.
Oblad et al., Catalysis and Catalysts. In McKetta ed, *Encyclopedia of Chemical Processing and Design*, pp. 420-490, 1978.
Office Action for U.S. Appl. No. 10/536,801, issued by the USPTO dated Apr. 8, 2008.
Office Action for U.S. Appl. No. 10/536,801, issued by the USPTO dated Jan. 7, 2010.
Office Action for U.S. Appl. No. 10/536,801, issued by the USPTO dated Jun. 17, 2009.
Office Action for U.S. Appl. No. 10/561,912, issued by the USPTO dated Aug. 25, 2008.
Office Action for U.S. Appl. No. 10/561,912, issued by the USPTO dated Feb. 11, 2009.
Office Action for U.S. Appl. No. 10/561,912, issued by the USPTO dated Jan. 14, 2008.
Office Action for U.S. Appl. No. 10/561,912, issued by the USPTO dated Sep. 2, 2009.
Office Action for U.S. Appl. No. 10/589,971, issued by the USPTO dated Jul. 27, 2010.
Office Action for U.S. Appl. No. 10/589,971, issued by the USPTO dated Mar. 22, 2011.
Office Action for U.S. Appl. No. 11/597,787, issued by the USPTO dated May 20, 2009.
Office Action for U.S. Appl. No. 11/597,787, issued by the USPTO dated Oct. 8, 2008.
Office Action for U.S. Appl. No. 11/597,787, issued by the USPTO dated Oct. 8, 2009.
Office Action for U.S. Appl. No. 11/990,272, issued by the USPTO dated Jul. 12, 2011.
Office Action for U.S. Appl. No. 11/990,272, issued by the USPTO dated May 2, 2012.
Office Action for U.S. Appl. No. 11/990,272, issued by the USPTO dated Oct. 28, 2011.
Office Action for U.S. Appl. No. 12/084,575, issued by the USPTO dated Aug. 29, 2011.
Office Action for U.S. Appl. No. 12/084,575, issued by the USPTO dated Mar. 19, 2012.
Office Action for U.S. Appl. No. 12/297,023, issued by the USPTO dated Apr. 12, 2012.
Office Action for U.S. Appl. No. 12/297,023, issued by the USPTO dated Sep. 27, 2011.
Office Action for U.S. Appl. No. 12/517,215, issued by the USPTO dated Feb. 27, 2012.
Office Action for U.S. Appl. No. 12/518,320, issued by the USPTO dated Dec. 6, 2011.

(56) References Cited

OTHER PUBLICATIONS

Office Action issued by the USPTO in U.S. Appl. No. 12/518,320 dated Dec. 8, 2010.
Office Action issued in U.S. Appl. No. 10/589,971 dated Aug. 8, 2013.
Office Action issued in U.S. Appl. No. 12/084,575 dated Jan. 2, 2015.
Office Action issued in U.S. Application No. 13/002,406 dated Aug. 19, 2013.
Office Action issued in U.S. Appl. No. 10/589,971 dated Mar. 6, 2014.
Office Action issued in U.S. Appl. No. 12/084,575 dated Apr. 25, 2014.
Office Action issued in U.S. Appl. No. 12/517,215 dated Apr. 6, 2015.
Office Action issued in U.S. Appl. No. 12/517,215 dated Jun. 24, 2014.
Office Action issued in U.S. Appl. No. 12/517,215 dated Mar. 12, 2014.
Office Action issued in U.S. Appl. No. 12/517,215 dated Nov. 14, 2014.
Office Action issued in U.S. Appl. No. 13/516,176 dated Mar. 6, 2015.
Office Action issued in U.S. Appl. No. 13/516,176 dated Oct. 9, 2014.
Office Action issued in U.S. No. 11/990,272 dated Feb. 6, 2013.
Office Action issued in U.S. Appl. No. 13/002,406 dated Mar. 15, 2013.
Olah, George A., et al., "AlCl3—Catalyzed Dichlorophosphorylation of Saturated Hydrocarbons with PCl3 in Methylene Chloride Solution," J. Org. Chem., 1990, 55, 1224-1227.
Ooka et al., "Highly active and selective palladium catalyst for hydroesterification of styrene and vinyl acetate promoted by polymeric sulfonic acids," Chemical Communications, pp. 1173-1175 (2005).
Osman, Serindag "Synthesis of some platinum(II) diphosphine complexes of the type [PtX2(P-P)] (X2=CO3; X=CH3COO, CF3COO, NCO)", Synth. React. Inorg. Met.-Org. Chem., vol. 27. No. 1, pp. 69-76, (1997).
Peng et al. "Chiral rodlike platinum complexes, double helical chains and potential asymmetric hydrogenation ligand based on "linear" building blocks: 1,8,9,16-tetrahydroxytetraphenylene and 1,8,9,16-tetrakis(diphenylphosphino)tetraphenylene" Journal of American Chemical Society, No. 127, pp. 9603-9611, (2005).
Portnoy et al., "Reactions of electron-rich arylpalladium complexes with olefins. Origin of the chelate effect in vinylation catalysis", Organometallics, vol. 13, No. 9, pp. 3465-3479 (1994).
Pugh et al., "Methoxycaronylation versus Hydroacylation of Ethene; Dramatic Influence of the Ligandin Cationic Palladium Catalysis," Adv. Synth. Catal., 2002, vol. 344, No. 8, pp. 837-840.
Pugh et al. "Tandem isomerisation-carbonylation catalysis: highly active palladium(II) catalysts for the selective methoxycarbonylation of internal alkenes to linear esters", Chemical Communications—CHEMCOM, Royal Society of Chemistry, GB, No. 16, (2001), pp. 1476-1477.
Reddy et al., "Unexpected cross-metathesis between Si—C and Si—Si bonds", Chemical Communications, No. 16, pp. 1865-1866 (1996).
Related U.S. Appl. No. 10/524,023, filed Nov. 17, 2005, Eastham et al.
Richmond et al., "Preparation of New Catalysts by the Immobilization of Palladium (II) Species onto Silica: An Investigation of their Catalytic Activity for the Cyclization of Aminoalkynes", J. Am Chem. Soc., vol. 123, 2001, pp. 10521-10525.
Rucklidge, et al., "Methoxycarbonylation of vinyl acetate catalysed by palladium complexes of bis(ditertiarybutylphosphinomethyl) benzene and related ligands", Chemical Communications, 2005, vol. 9 pp. 1176-1178.

Seayad et al., "Hydroesterification of styrene using an in situ formed Pd(OTs)2(PPh3)2 complex catalyst", Journal of Molecular Cat. A. Chem., vol. 151, 2000, pp. 47-59.
Supplemental Notice of Allowance issued in U.S. Appl. No. 13/520,523 dated Feb. 10, 2015.
Tamao et al., "Alkyl Group Isomerization in the Cross-Coupling Reaction of Secondary Alkyl Gringnard Reagents with Organic Halides in the Presence of Nickel-Phosphine Complexes as Catalysts", Journal of the American Chemical Society, vol. 94, 1972, pp. 9268-9269.
Tanaka et al., "Synthesis of ketones via carbonylation of organic halides. II. Palladium-catalysed carbonylation of organic halides with terminal acetylenes in the presence of amines. Novel acetylenic ketone synthesis", Nippon Kagaku Kaishi, No. 3, pp. 537-546 (1985).
Tolman, "Phosphorous Ligand Exchange Equilibria on Zerovalent Nickel. A Dominant Role for Steric Effects," Journal of the American Chemical Society, vol. 92, No. 10, pp. 2956-2965, 1970.
Tolman, "Steric Effects of Phosphorous Ligands in Organometallic Chemistry and Homogeneous Catalysis," Chemical Reviews, vol. 77, No. 3, pp. 313-348, 1977.
Tudor et al. "Diasteroisomer interconversion in chiral BiphepPtX2 complexes", Organometallics, No. 19, pp. 4376-4384, (2000).
Uchimaru et al., "Ring-opening polymerization of 1,1,2,2-tetramethyl-1,2-disilacyclopentane via palladium complex-catalysed Si—Si bond metathesis", Chemistry Letters, No. 2, p. 164 (1995).
Vavasori et al., "Carbon monoxide-ethylene copolymerization catalyzed by a Pd(AcO)2/dpppTs0H$^1$ system: the promoting effect of water and of the acid", Journal of Molecular Cat. A. Chem., vol. 110, 1996, Abstract.
Vavasori et al., "Highly active [Pd(AcO)$_2$(dppp(] catalyst for the CO-C$_2$H$_4$ copolymerization in H$_2$O-CH$_3$COOH solvent [dppp=1,3-bis (diphenylphosphino)propane]" Journal of Molecular Cat. A. Chem., vol. 204-205, 2003, pp. 295-303.
Wang et al., "Polymer-Bound Bidentate-Phospine-Palladium Complex as a Catalyst in the Heck Arylation", J. Org. Chem, vol. 59, No. 18, 1994, pp. 5358-5364.
Wang, et al., "Synthesis and Use in Asymmetric Hydrogenations of Solely Planar Chiral 1,2-Disubstituted and 1,2,3-Trisubstituted Ferrocenyl Diphosphines: A Comparative Study", Organometallics, 2007, vol. 26, pp. 3530-3540.
Yu, et al., "Preparation of Polymer-Protected Pt/Co Bimetallic Colloid and its Catalytic Properties in Selective Hydrogenation of Cinnamaldehyde to Cinnamyl Alcohol," Polymers FOR Advanced Technologies, GB, John Wiley and Sons, Chichester, Aug. 1, 1996, 719-722, vol. 7, No. 8.
Wen et al. "Synthesis, resolution, and applications of 1,16-dihydroxytetraphenylene as a novel building block in molecular recognition and assembly", Journal of Organic Chemistry, No. 68, pp. 8918-8931, (2003).
White et al., "Basic Energy Sciences Advisory Committee Subpanel Workshop Report," Opportunities for Catalysis in the 21st Century, 2002, pp. 1-47.
Written Opinion of the International Searching Authority issued in International Application No. PCT/GB2009/050780 dated Oct. 15, 2009.
Written Opinion of the International Searching Authority issued in International Application No. PCT/GB2010/052093 dated Apr. 8, 2011.
Written Opinion of the International Searching Authority issued in International Application No. PCT/GB2010/052214 dated Mar. 30, 2011.
Written Opinion of the International Searching Authority, issued in PCT/GB2007/050189 filed Apr. 10, 2007.
Wurst et al., "Synthesis and structure of the platinum (0) compounds [(dipb)Pt]2(COD) and (dipb)3Pt2 and of the cluster Hg6[Pt(dipb)]4 (dipb=(iPr)2P(CH2)4P(i-Pr)2)", Zeitschrift Für Anorganische Und Allgemeine Chemie, vol. 395, pp. 239-250 (1991).
Office Action issued in U.S. Appl. No. 12/084,575 dated Jul. 24, 2015.
Office Action issued in U.S. Appl. No. 12/517,215 dated Jul. 21, 2015.

(56) References Cited

OTHER PUBLICATIONS

Office Action issued in U.S. Appl. No. 13/516,176 dated Aug. 19, 2015.
"Basic Energy Sciences Advisory Committee Subpanel Workshop Report," Opportunities for catalysis in the 21st century, 2002, p. 1-46.
Hessler et al., "Synthesis and coordination chemistry of hemilabile P, N-hybrid ligands with terminal 2-pyridyl or groups," Chemische Berichte, Germany 1994, 127(3): 481-488.
Hessler et al., "Water Soluble Cationic Phosphine Ligands Containing m-Guanidinium Phenyl Moieties," Syntheses and Applications in Aqueous Heck Type Reactions, Journal of Organic Chemistry, 1997, 62(8): 2362-2369.

* cited by examiner

CATALYST SYSTEM

The present invention relates to a novel catalyst system, a novel carbonylation reaction medium and a process for the carbonylation of ethylenically unsaturated compounds using a novel catalyst system.

The carbonylation of ethylenically unsaturated compounds using carbon monoxide in the presence of an alcohol or water and a catalyst system comprising a Group VIII metal, eg. palladium, and a phosphine ligand eg. an alkyl phosphine cycloalkyl phosphine, aryl phosphine, pyridyl phosphine or bidentate phosphine, has been described in numerous European patents and patent applications, eg. EP-A-0055875, EP-A-04489472, EP-A-0106379, EP-A-0235864, EP-A-0274795, EP-A-0499329, EP-A-0386833, EP-A-0441447, EP-A-0489472, EP-A-0282142, EP-A-0227160, EP-A-0495547 and EP-A-0495548. In particular, EP-A-0227160, EP-A-0495547 and EP-A-0495548 disclose that bidentate phosphine ligands provide catalyst systems which enable higher reaction rates to be achieved.

WO 96/19434 discloses a bridging group in the form of an optionally substituted aryl moiety, linked to the said phosphorous atoms via available adjacent carbon atoms on the said aryl moiety. Such a ligand is more stable and leads to reaction rates which are significantly higher than those previously disclosed and produces little or no impurities for the carbonylation of ethylene. Each phosphorous atom in the said ligand is also linked to two tertiary carbon atoms.

However, conventional metal-catalysed reactions, such as those described in WO 96/19434 tend to suffer from the drawback that the catalyst tends to de-activate over the course of a period of continuous operation as the palladium compound is reduced to palladium metal, this contributing to the economic viability of the process. WO 01/10551 addressed this problem via the use of stabilising compounds such as polymeric dispersants in the reaction medium, thus improving in the recovery of metal which has been lost from the catalyst system.

Although catalyst systems have been developed which exhibit reasonable stability during the carbonylation process and permit relatively high reaction rates to be achieved, there still exists a need for improved catalyst systems. Suitably, the present invention aims to provide an improved catalyst for carbonylating ethylenically unsaturated compounds.

J. Mol. Cat. A 204-205 (2003) pgs 295-303 suggests that a relative increase in the ligand concentration, for example by the addition of more ligand, has a detrimental effect on productivity. Similar results are reported in J. Mol. Cat. A. Chem. 110 (1996) pgs 13-23 and J. Mol. Cat. A. Chem. 151 (2000) pgs 47-59.

Moreover, WO-A-01/72697 describes a process for the carbonylation of pentenenitrile but teaches that there are disadvantages associated at relatively high acid:palladium ratios. The authors state that the disadvantages occur because high acid concentration conditions are corrosive and more ligand degradation results from quaternisation with the acid and the olefinic compound.

WO-A-01/68583 discloses a process for the carbonylation of ethylenically unsaturated compounds using phosphine-based bidentate ligands. However, this disclosure is directed towards the use of relatively low acid levels, leading to low acid:ligand values. Moreover, the ligand:metal ratios are low. WO-A-03/040159 similarly discloses low acid:ligand and ligand:metal ratios.

WO-A-98/45040 discloses catalyst systems comprising palladium compound and bidentate phosphorus ligands. However, acid:ligand ratios of less than 1:1 are taught.

Finally, WO-A-01/72697 discloses a process for the preparation of a 5-cyanovaleric acid by carbonylation of a pentenenitrile. The disclosure points out the disadvantages in using high acid concentrations and teaches towards the use of relatively low acid levels.

Hence, an aim of the present invention is to seek to establish a catalyst system wherein the levels of ligand and acid are relatively high, but wherein the disadvantages of the prior art noted hereinbefore are addressed and alleviated, at least to some extent, the aforesaid being one object of the present invention.

DESCRIPTION

Figure 1:
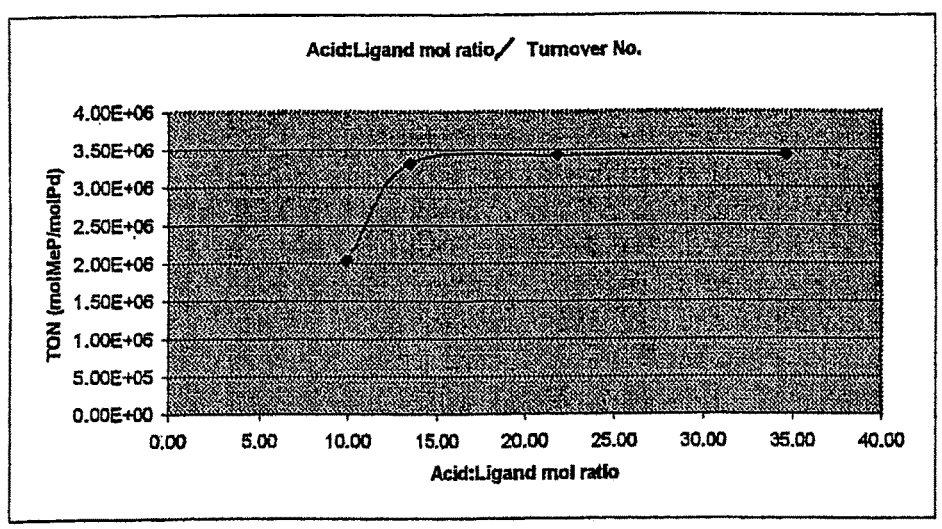
FIG. 1 shows TON versus acid:ligand mol ratio.

According to the present invention there is provided a catalyst system, a process for the carbonylation of an ethylenically unsaturated compound, a reaction medium, and use as set forth in the appended claims.

Preferred features of the invention will be apparent from the dependent claims, and the description which follows.

According to a first aspect, the present invention provides a catalyst system capable of catalysing the carbonylation of an ethylenically unsaturated compound, which system is obtainable by combining:
a) a metal of Group VIB or Group VIIIB or a compound thereof,
b) a bidentate phosphine, arsine, or stibine ligand, preferably a bidentate phosphine ligand, and
c) an acid,
wherein said ligand is present in at least a 2:1 molar excess compared to said metal or said metal in said metal compound, and that said acid is present in at least a 2:1 molar excess compared to said ligand.

Typically, component b) is a bidentate phosphine, arsine, or stibine.

Suitably, all of components a) to c) of the catalyst system can be added in situ to the reaction vessel wherein the carbonylation is to take place. Alternatively, the components a) to c) can be added sequentially in any order to form the catalyst system, or in some specified order, either directly into the vessel or outside the vessel and then added to the vessel. For instance, the acid component c) may first be added to the bidentate ligand component b), to form a protonated ligand, and then the protonated ligand can be added to the metal or compound thereof (component a)) to form the catalyst system. Alternatively, the ligand component b) and metal or compound thereof (component a)) can be mixed to form a chelated metal compound, and the acid (component c)) is then added. Alternatively, any two components can be reacted together to form an intermediate moiety which is then either added to the reaction vessel and the third component added, or is first reacted with the third component and then added to the reaction vessel.

As such, the present invention is directed to a catalyst system wherein the relative molar concentrations of both the bidentate ligand and the acid are at levels in excess of those previously envisaged, leading to surprising and unexpected advantages when using the catalyst system in the carbonylation of ethylenically unsaturated compounds, and the alleviation or at least reduction of at least some of the disadvantages of the prior art systems. In particular, the use of a catalyst system of the present invention leads at least to a more stable system, increased reaction rates, and improved turnover numbers in carbonylation reactions of ethylenically unsaturated compounds.

As stated above, the ligand is present in the catalyst system, or precursor thereto, in such quantity that the ratio of said ligand to the said metal (i.e. component b) to component a)) is at least a 2:1 molar ratio. Preferably, the ratio of said ligand to the said metal is greater than a 2:1 molar ratio, more preferably in the range 2:1 to 1000:1, even more preferably in the range 2.5:1 to 1000:1, yet more preferably in the range 3:1 to 1000:1, even more preferably in the range 5:1 to 750:1, more preferably in the range 7:1 to 1000:1, especially in the range 8:1 to 900:1, still more preferably in the range 10:1 to 500:1, yet still more preferably in the range 20:1 to 400:1, even more preferably in the range 50:1 to 250:1, most preferably in the range in excess of 50:1, for example 51:1 and upwards, more specifically 51:1 to 250:1 or even to 1000:1. Alternatively, the said ratio can be in the range 15:1 to 45:1, preferably 20:1 to 40:1, more preferably 25:1 to 35:1.

As stated above, the acid is present in the catalyst system, or precursor thereto, in such quantity that the ratio of said acid to the said ligand (i.e. component c) to component b)) is at least a 2:1 molar ratio. Preferably, the ratio of said acid to the said ligand is greater than a 2:1 molar ratio, more preferably in the range 2:1 to 100:1, even more preferably in the range 4:1 to 100:1, yet more preferably in the range 5:1 to 95:1, still more preferably in the range greater than 5:1 to 95:1, yet more preferably in the range greater than 5:1 to 75:1, more preferably in the range 10:1 to 50:1, even more preferably in the range 20:1 to 40:1, still more preferably in the range greater than 20:1 to 40:1 (e.g. 25:1 to 40:1, or 25:1 to less than 30:1), more preferably in excess of 30:1, suitably with any of the upper limits provided hereinbefore (e.g. 30:1 to 40:1, or 50:1, etc.), or more preferably in excess of 35:1, yet more preferably in excess of 37:1, suitably either with any of the upper limits provided hereinbefore. Each of the ranges in this paragraph can be used in conjunction with each of the ligand to metal ratio ranges disclosed hereinabove, i.e. ratios of component b) to component a).

By "acid", we mean an acid or salt thereof, and references to acid should be construed accordingly.

The advantages in working within the ligand to metal, and acid to ligand ratios, set out above are manifest in that the stability of the catalyst system is improved, as evidenced by increases in the turnover number (TON) of the metal. By improving the stability of the catalyst system, the usage of metal in the carbonylation reaction scheme is kept to a minimum.

Without wishing to be bound by theory, it is believed that by working within the specific ratio ranges noted herein, it is surprisingly found that the ligand component of the catalyst system is protected against inadvertent aerial oxidation (in instances where there is any ingress of air into the reaction system), and the overall stability of the catalyst system is improved, thus keeping the usage of the metal component of the catalyst system to a minimum. Moreover, the forward reaction rate of the reaction is surprisingly improved.

In effect, the level of acid should be such that for the particular bidentate ligand employed, the level of acid should be such that phosphine, arsine or stibine is fully protonated. Hence, to show the improved effects, the level of ligand should be above some minimum level, as given by the ligand:metal molar ratio, and the level of acid should be above some minimum level with respect to the level of ligand present to encourage protonation, as given by the acid:ligand molar ratio.

Preferably, the acid is present in the catalyst system, or precursor thereto, in such quantity that the molar ratio of said acid to said metal (i.e. component c) to component a)) is at least 4:1, more preferably from 4:1 to 100000:1, even more preferably 10:1 to 75000:1, yet more preferably 20:1 to 50000:1, yet still more preferably 25:1 to 50000:1, yet still more preferably 30:1 to 50000:1, yet even more preferably 40:1 to 40000:1, still more preferably 100:1 to 25000:1, more preferably 120:1 to 25000:1, more preferably 140:1 to 25000:1, yet still more preferably 200:1 to 25000:1, most preferably 550:1 to 20000:1, or greater than 2000:1 to 20000:1. Alternatively, the said ratio can be in the range 125:1 to 485:1, more preferably 150:1 to 450:1, even more preferably 175:1 to 425:1, yet even more preferably 200:1 to 400:1, most preferably 225:1 to 375:1. Each of these ranges in this paragraph can be used in conjunction with each of the ligand to metal ratio ranges disclosed hereinabove, i.e. ratios of component b) to component a), and/or each of the acid to ligand ratio ranges disclosed hereinabove, i.e. ratios of component c) to component b).

For the avoidance of any doubt, all of the aforementioned ratios and ratio ranges apply to all of the ligand embodiments set out in more detail hereinafter.

In one embodiment of the present invention, the bidentate phosphine ligand is of general formula (I)

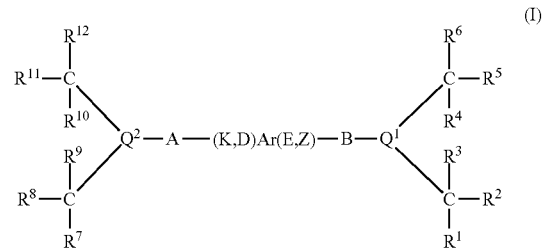

wherein:
Ar is a bridging group comprising an optionally substituted aryl moiety to which the phosphorus atoms are linked on available adjacent carbon atoms;
A and B each independently represent lower alkylene;
K, D, E and Z are substituents of the aryl moiety (Ar) and each independently represent hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J represents lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;
$R^{13}$ to $R^{18}$ each independently represent hydrogen, lower alkyl, aryl, or Het, preferably each independently represent lower alkyl, aryl, or Het;
$R^{19}$ to $R^{27}$ each independently represent hydrogen, lower alkyl, aryl or Het;

$R^1$ to $R^{12}$ each independently represent hydrogen, lower alkyl, aryl, or Het, preferably each independently represent lower alkyl, aryl, or Het;

$Q^1$, $Q^2$ and $Q^3$ (when present) each independently represent phosphorous, arsenic or antimony and in the latter two cases references to phosphine or phosphorous above are amended accordingly, with preferably both $Q^1$ and $Q^2$ representing phosphorus, more preferably all of $Q^1$, $Q^2$ and $Q^3$ (when present) representing phosphorus.

Suitably, the bidentate phosphines of the invention should preferably be capable of bidentate coordination to the Group VIB or Group VIIIB metal or compound thereof, more preferably to the preferred palladium.

Preferably, when K, D, E or Z represent -J-$Q^3$ ($CR^{13}(R^{14})$ ($R^{15}$))$CR^{16}(R^{17})(R^{18})$, the respective K, D, E or Z is on the aryl carbon adjacent the aryl carbon to which A or B is connected or, if not so adjacent, is adjacent a remaining K, D, E or Z group which itself represents -J-$Q^3$($CR^{13}(R^{14})$ ($R^{15}$))$CR^{16}(R^{17})(R^{18})$.

Specific but non-limiting examples of bidentate ligands within this embodiment include the following: 1,2-bis-(di-tert-butylphosphinomethyl)benzene, 1,2-bis-(di-tert-pentylphosphinomethyl)benzene, 1,2-bis-(di-tert-butylphosphinomethyl)naphthalene. Nevertheless, the skilled person in the art would appreciate that other bidentate ligands can be envisaged without departing from the scope of the invention.

The term "Ar" or "aryl" when used herein, includes five-to-ten-membered, preferably, six-to-ten membered carbocyclic aromatic groups, such as phenyl and naphthyl, which groups are optionally substituted with, in addition to K, D, E or Z, one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group may itself be optionally substituted or terminated as defined below). Furthermore, the aryl moiety may be a fused polycyclic group, e.g. naphthalene, biphenylene or indene.

By the term "a metal of Group VIB or Group VIIIB" we include metals such as Cr, Mo, W, Fe, Co, Ni, Ru, Rh, Os, Ir, Pt and Pd. Preferably, the metals are selected from Ni, Pt and Pd. More preferably, the metal is Pd. For the avoidance of doubt, references to Group VIB or VIIIB metals herein should be taken to include Groups 6, 8, 9 and 10 in the modern periodic table nomenclature.

The term "Het", when used herein, includes four-to-twelve-membered, preferably four-to-ten-membered ring systems, which rings contain one or more heteroatoms selected from nitrogen, oxygen, sulphur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below) $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen, aryl or lower alkyl (which alkyl group itself may be optionally substituted or terminated as defined below). The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The term "lower alkyl" when used herein, means $C_1$ to $C_{10}$ alkyl and includes methyl, ethyl, propyl, butyl, pentyl, hexyl and heptyl groups. Unless otherwise specified, alkyl groups may, when there is a sufficient number of carbon atoms, be linear or branched, be saturated or unsaturated, be cyclic, acyclic or part cyclic/acyclic, and/or be substituted or terminated by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or lower alkyl, and/or be interrupted by one or more oxygen or sulphur atoms, or by silano or dialkylsilcon groups.

Lower alkyl groups or alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, K, D, E and Z may represent and with which aryl and Het may be substituted, may, when there is a sufficient number of carbon atoms, be linear or branched, be saturated or unsaturated, be cyclic, acyclic or part cyclic/acyclic, and/or be interrupted by one or more of oxygen or sulphur atoms, or by silano or dialkylsilicon groups, and/or be substituted by one or more substituents selected from halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het wherein $R^{19}$ to $R^{27}$ each independently represent hydrogen, aryl or lower alkyl.

Similarly, the term "lower alkylene" which A, B and J (when present) represent in a compound of formula I, when used herein, includes $C_1$ to $C_{10}$ groups which are bonded to other moieties at least at two places on the group and is otherwise defined in the same way as "lower alkyl".

Halo groups with which the above-mentioned groups may be substituted or terminated include fluoro, chloro, bromo and iodo.

Where a compound of a formula herein contains an alkenyl group, cis (E) and trans (Z) isomerism may also occur. The present invention includes the individual stereoisomers of the compounds of any of the formulas defined herein and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of a compound one of the formulas or a suitable salt or derivative thereof. An individual enantiomer of a compound of one of the formulas may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the process of the invention.

It will be appreciated by those skilled in the art that the compounds of formula I may function as ligands that coordinate with the Group VIB or Group VIIIB metal or compound thereof in the formation of the catalyst system of the invention. Typically, the Group VIB or Group VIIIB metal or compound thereof coordinates to the one or more phosphorous, arsenic and/or antimony atoms of the compound of formula I.

Preferably, $R^1$ to $R^{18}$ each independently represent lower alkyl or aryl. More preferably, $R^1$ to $R^{18}$ each independently represent $C_1$ to $C_6$ alkyl, $C_1$-$C_6$ alkyl phenyl (wherein the phenyl group is optionally substituted as defined herein) or phenyl (wherein the phenyl group is optionally substituted as defined herein). Even more preferably, $R^1$ to $R^{18}$ each independently represent $C_1$ to $C_6$ alkyl, which is optionally substituted as defined herein. Most preferably, $R^1$ to $R^{18}$ each represent non-substituted $C_1$ to $C_6$ alkyl such as methyl, ethyl, n-propyl, iso-propyl, n-butyl, iso-butyl, tert-butyl, pentyl, hexyl and cyclohexyl.

Alternatively, or additionally, each of the groups $R^1$ to $R^3$, $R^4$ to $R^6$, $R^7$ to $R^9$, $R^{10}$ to $R^{12}$, $R^{13}$ to $R^{15}$ or $R^{16}$ to $R^{18}$ together independently may form cyclic structures such as 1-norbornyl or 1-norbornadienyl. Further examples of composite groups include cyclic structures formed between $R^1$-$R^{18}$. Alternatively, one or more of the groups may represent a solid phase to which the ligand is attached.

In a particularly preferred embodiment of the present invention $R^1$, $R^4$, $R^7$, $R^{10}$, $R^{13}$ and $R^{16}$ each represent the same lower alkyl, aryl or Het moiety as defined herein, $R^2$, $R^5$, $R^8$, $R^{11}$, $R^{14}$ and $R^{17}$ each represent the same lower alkyl, aryl or Het moiety as defined herein, and $R^3$, $R^6$, $R^9$, $R^{12}$, $R^{15}$ and $R^{18}$ each represent the same lower alkyl, aryl or Het moiety as defined herein. More preferably $R^1$, $R^4$, $R^7$, $R^{10}$, $R^{13}$ and $R^{16}$ each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl; $R^2$, $R^5$, $R^8$, $R^{11}$, $R^{14}$ and $R^{17}$ each independently represent the same $C_1$-$C_6$ alkyl as defined above; and $R^3$, $R^6$, $R^9$, $R^{12}$, $R^{15}$ and $R^{18}$ each independently represent the same $C_1$-$C_6$ alkyl as defined above. For example: $R^1$, $R^4$, $R^7$, $R^{10}$, $R^{13}$ and $R^{16}$ each represent methyl; $R^2$, $R^5$, $R^8$, $R^{11}$, $R^{14}$ and $R^{17}$ each represent ethyl; and, $R^3$, $R^6$, $R^9$, $R^{12}$, $R^{15}$ and $R^{18}$ each represent n-butyl or n-pentyl.

In an especially preferred embodiment of the present invention each $R^1$ to $R^{18}$ group represents the same lower alkyl, aryl, or Het moiety as defined herein. Preferably, each $R^1$ to $R^{18}$ represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl. Most preferably, each $R^1$ to $R^{18}$ represents methyl.

In the compound of formula I, preferably each $Q^1$, $Q^2$ and $Q^3$ (when present) are the same. Most preferably, each $Q^1$, $Q^2$ and $Q^3$ (when present) represents phosphorous.

Preferably, in the compound of formula I, A, B and J (when present) each independently represent $C_1$ to $C_6$ alkylene which is optionally substituted as defined herein, for example with lower alkyl groups. Preferably, the lower alkylene groups which A, B and J (when present) represent are non-substituted. A particular preferred lower alkylene which A, B and J may independently represent is —$CH_2$— or —$C_2H_4$—. Most preferably, each of A, B and J (when present) represent the same lower alkylene as defined herein, particularly —$CH_2$—.

Preferably, in the compound of formula I when K, D, E or Z does not represent -J-$Q^3$($CR^{13}$($R^{14}$)($R^{15}$))$CR^{15}$($R^{17}$)($R^{18}$), K, D, E or Z represents hydrogen, lower alkyl, phenyl or lower alkylphenyl. More preferably, K, D, E or Z represent hydrogen, phenyl, $C_1$-$C_6$ alkylphenyl or $C_1$-$C_6$ alkyl, such as methyl, ethyl, propyl, butyl, pentyl and hexyl. Most preferably, K, D, E or Z represents hydrogen.

Preferably, in the compound of formula I when K, D, E and Z together with the carbon atoms of the aryl ring to which they are attached do not form a phenyl ring, K, D, E and Z each independently represent hydrogen, lower alkyl, phenyl or lower alkylphenyl. More preferably, K, D, E and Z each independently represent hydrogen, phenyl, $C_1$-$C_6$ alkylphenyl or $C_1$-$C_6$ alkyl, such as methyl, ethyl, propyl, butyl, pentyl and hexyl. Even more preferably, K, D, E and Z represent the same substituent. Most preferably, they represent hydrogen.

Preferably, in the compound of formula I when K, D, E or Z does not represent -J-$Q^3$($CR^{13}$($R^{14}$)($R^{15}$))$CR^{16}$($R^{17}$)($R^{18}$) and K, D, E and Z together with the carbon atoms of the aryl ring to which they are attached do not form a phenyl ring, each of K, D, E and Z represent the same group selected from hydrogen, lower alkyl, aryl, or Het as defined herein; particularly hydrogen or $C_1$-$C_6$ alkyl (more particularly unsubstituted $C_1$-$C_6$ alkyl), especially hydrogen.

Preferably, in the compound of formula I when two of K, D, E and Z together with the carbon atoms of the aryl ring to which they are attached form a phenyl ring, then the phenyl ring is optionally substituted with one or more substituents selected from aryl, lower alkyl (which alkyl group may itself be optionally substituted or terminated as defined below), Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$ or $C(S)NR^{25}R^{26}$ wherein $R^{19}$ to $R^{27}$ each independently represent hydrogen or lower alkyl (which alkyl group may itself be optionally substituted or terminated as defined herein). More preferably, the phenyl ring is not substituted by any substituents i.e. it bears hydrogen atoms only.

Preferred compounds of formula I include those wherein:
A and B each independently represent unsubstituted $C_1$ to $C_6$ alkylene;
K, D, Z and E each independently represent hydrogen, $C_1$-$C_6$ alkyl, phenyl, $C_1$-$C_6$ alkylphenyl or -J-$Q^3$($CR^{13}$($R^{14}$)($R^{15}$))$CR^{16}$($R^{17}$)($R^{18}$) where J represents unsubstituted $C_1$ to $C_6$ alkylene; or two of K, D, Z and E together with the carbon atoms of the aryl ring to which they are attached form a phenyl ring which is optionally substituted by one or more substituents selected from lower alkyl, phenyl or lower alkylphenyl.
$R^1$ to $R^{18}$ each independently represent $C_1$ to $C_6$ alkyl, phenyl or $C_1$ to $C_6$ alkylphenyl.

Further preferred compounds of formula I include those wherein:
A and B both represent —$CH_2$— or $C_2H_4$, particularly $CH_2$;
K, D, Z and E each independently represent hydrogen, $C_1$-$C_6$ alkyl phenyl or $C_1$-$C_6$ alkyl or -J-$Q^3$($CR^{13}$($R^{14}$)($R^{15}$))$CR^{16}$($R^{17}$)($R^{18}$) where J is the same as A; or two of K, D, E and Z together with the carbon atoms of the aryl ring to which they are attached form an unsubstituted phenyl ring;
$R^1$ to $R^{18}$ each independently represent $C_1$ to $C_6$ alkyl;

Still further preferred compounds of formula I include those wherein:
$R^1$ to $R^{18}$ are the same and each represents $C_1$ to $C_6$ alkyl, particularly methyl.

Still further preferred compounds of formula I include those wherein:
K, D, Z and E are each independently selected from the group consisting of hydrogen or $C_1$ to $C_6$ alkyl, particularly where each of K, D, Z and E represent the same group, especially where each of K, D, Z and E represent hydrogen; or
K represents —$CH_2$-$Q^3$($CR^{13}$($R^{14}$)($R^{15}$))$CR^{16}$($R^{17}$)($R^{18}$) and D, Z and E are each independently selected from the group consisting of hydrogen or $C_1$ to $C_6$ alkyl, particularly where both D and E represent the same group, especially where D, Z and E represent hydrogen.

Especially preferred specific compounds of formula I include those wherein:
each $R^1$ to $R^{12}$ is the same and represents methyl;
A and B are the same and represent —$CH_2$—;
K, D, Z and E are the same and represent hydrogen.

In a still further embodiment, at least one ($CR^xR^yR^z$) group attached to $Q^1$ and/or $Q^2$, i.e. $CR^1R^2R^3$, $CR^4R^5R^6$, $CR^7R^8R^9$, or $CR^{10}R^{11}R^{12}$, may instead be represented by the group (Ad) wherein:

Ad each independently represent an optionally substituted adamantyl or congressyl radical bonded to the phosphorous atom via any one of its tertiary carbon atoms, the said optional substitution being by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$; or if both ($CR^xR^yR^z$) groups attached to either or both $Q^1$ and/or $Q^2$, or $Q^3$ (if present) together with either $Q^1$ or $Q^2$ (or $Q^3$) as appropriate, form an optionally substituted 2-phospha-tricyclo[3.3.1.1{3,7}]decyl group or derivative thereof, or form a ring system of formula

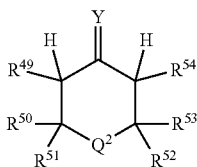

wherein
$R^{49}$, and $R^{54}$, each independently represent hydrogen, lower alkyl or aryl;
$R^{50}$ to $R^{53}$, when present, each independently represent hydrogen, lower alkyl, aryl or Het; and
Y represents oxygen, sulfur or N—$R^{55}$; and $R^{55}$, when present, represents hydrogen, lower alkyl or aryl.

In this embodiment, formula I may be represented as:

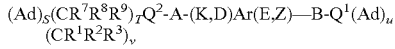

wherein Ar, A, B, K, D, E and Z, $Q^1$, $Q^2$, and $Q^3$, and $R^1$ to $R^{27}$ are as defined hereinbefore except that K, D, E and Z may represent -J-$Q^3$($Ad)_w(CR^{13}(R^{14})(R^{15}))_x$ instead of -J-$Q^3$($CR^{13}(R^{14})(R^{15}))CR^{16}(R^{17})(R^{18})$ and Ad is as defined above,
S & U=0, 1 or 2 provided that S+U≥1;
T & V=0, 1 or 2 provided that T+V≤3;
W & X=0, 1 or 2.

In addition to the preferred embodiments for $R^1$ to $R^{18}$, $Q^1$ to $Q^3$, A, B, J (when present), K, D, E or Z, $R^{19}$ to $R^{27}$, noted hereinbefore, all of which equally apply to the present embodiment where at least one (Ad) group is present, the following also applies.

Further preferred compounds of formula I include those wherein:
A and B both represent —$CH_2$— or —$C_2H_4$—, particularly —$CH_2$—;
K, D, Z and E each independently represent hydrogen, $C_1$-$C_6$ alkyl phenyl or $C_1$-$C_6$ alkyl or -J-$Q^3$($Ad)_w(CR^{13}(R^{14})(R^{15}))_x$ where J is the same as A; or two of K, D, E and Z together with the carbon atoms of the aryl ring to which they are attached form an unsubstituted phenyl ring;
$R^1$ to $R^3$, $R^7$ to $R^9$, and $R^{13}$ to $R^{15}$ (when present) each independently represent $C_1$ to $C_6$ alkyl, and the total number of (Ad) groups attached to $Q^1$ and $Q^2$ is ≥3, i.e. S+U≥3, and W and X=0, 1 or 2.

Still further preferred compounds of formula I include those wherein:
$R^1$ to $R^3$, $R^7$ to $R^9$ and $R^{13}$ to $R^{15}$ (when present) are the same and each represents $C_1$ to $C_6$ alkyl, particularly methyl, and the total number of (Ad) groups attached to $Q^1$ and $Q^2$ is ≥3, i.e. S+U≥3.

Still further preferred compounds of formula I include those wherein:
K, D, Z and E are each independently selected from the group consisting of hydrogen or $C_1$ to $C_6$ alkyl, particularly where each of K, D, Z and E represent the same group, especially where each of K, D, Z and E represent hydrogen; or
K represents —$CH_2$-$Q^3$($Ad)_w(CR^{13}(R^{14})(R^{15})_x$ and D, Z and E are each independently selected from the group consisting of hydrogen or $C_1$ to $C_6$ alkyl, particularly where both D and E represent the same group, especially where D, Z and E represent hydrogen, wherein W and X=0, 1 or 2.

Especially preferred specific compounds of formula I include those wherein:
each $R^1$ to $R^3$, and $R^7$ to $R^9$ is the same and represents methyl or the total number of (Ad) groups attached to $Q^1$ and $Q^2$ is 2, i.e. S+U=2;
A and B are the same and represent —$CH_2$—;
K, D, Z and E are the same and represent hydrogen.

Especially preferred specific compounds of formula I include those wherein Ad is joined to $Q_1$ or $Q^2$ at the same position in each case. Preferably S≥1 and U≥1, more preferably, S=2 and U≥1 or vice versa, most preferably S & U=2, wherein S is the number of (Ad) groups attached to $Q^2$ and U is the number of (Ad) groups attached to $Q^1$.

Specific but non-limiting examples of bidentate ligands within this embodiment include the following: 1,2 bis(diadamantylphosphinomethyl)benzene, 1,2 bis(di-3,5-dimethyladamantylphosphinomethyl)benzene, 1,2 bis(di-5-tert-butyladamantaylphosphinomethyl)benzene, 1,2 bis(1-adamantyl tert-butyl-phosphinomethyl)benzene, 1,2 bis(di-1-diamantanephosphinomethyl)benzene, 1-[(diadamantylphosphinomethyl)-2-(di-tert-butylphosphinomethyl)]benzene, 1-(di-tert-butylphosphinomethyl)-2-(dicongressylphosphinomethyl)benzene, 1-(di-tert-butylphosphinomethyl)-2-(phospha-adamantylphosphinomethyl)benzene, 1-(diadamantylphosphinomethyl)-2-(phospha-adamantylphosphinomethyl)benzene, 1-(tert-butyladamantyl)-2-(di-adamantyl)-(phosphinomethyl) benzene and 1-[(P-(2,2,6,6,-tetra-methylphosphinan-4-one) phosphinomethyl)]-2-(phospha-adamantylphosphinomethyl)benzene.

Nevertheless, the skilled person in the art would appreciate that other bidentate ligands can be envisaged without departing from the scope of the invention.

In a yet further embodiment, the bidentate phosphine ligand is of general formula (III).
wherein:

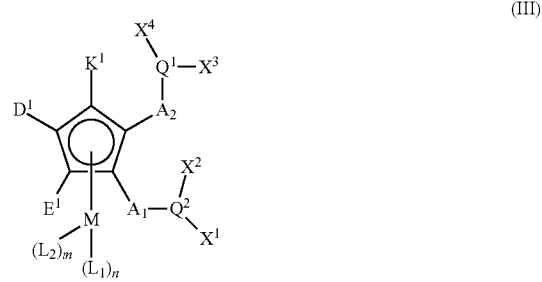

$A_1$ and $A_2$, and $A_3$, $A_4$ and $A_5$ (when present), each independently represent lower alkylene;

$K^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_3$-$Q^3$($X^5$)$X^6$;

$D^1$ is selected from the group consisting of hydrogen, lower alkyl, aryl, Het, halo, cyano, nitro, —$OR^{19}$, $OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_4$-$Q^4$($X^7$)$X^8$;

$E^1$ is selected from the group consisting of hydrogen, lower alkyl, aryl, Het, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$, —$SR^{29}$, —$C(O)SR^{30}$, —$CF_3$ or -$A_5$-$Q^5$($X^9$)$X^{10}$;

or both $D^1$ and $E^1$ together with the carbon atoms of the cyclopentadienyl ring to which they are attached form an optionally substituted phenyl ring:

$X^1$ represents $CR^1(R^2)(R^3)$, congressyl or adamantyl, $X^2$ represents $CR^4(R^5)(R^6)$, congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

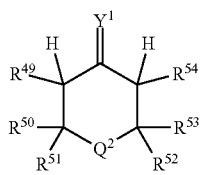

(IIIa)

$X^3$ represents $CR^7(R^8)(R^9)$, congressyl or adamantyl, $X^4$ represents $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

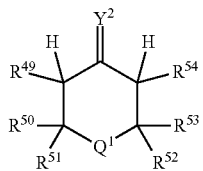

(IIIb)

$X^5$ represents $CR^{13}(R^{14})(R^{15})$, congressyl or adamantyl, $X^6$ represents $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

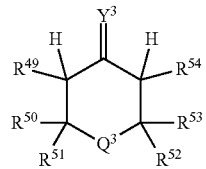

(IIIc)

$X^7$ represents $CR^{31}(R^{32})(R^{33})$, congressyl or adamantyl, $X^8$ represents $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula Hid

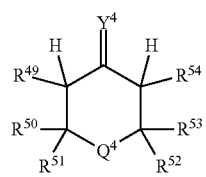

(IIId)

$X^9$ represents $CR^{37}(R^{38})(R^{39})$, congressyl or adamantyl, $X^{10}$ represents $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula Hie

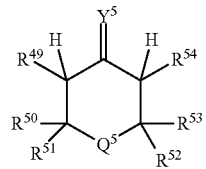

(IIIe)

and in this yet further embodiment, $Q^1$ and $Q^2$, and $Q^3$, $Q^4$ and $Q^5$ (when present), each independently represent phosphorus, arsenic or antimony;

M represents a Group VIB or VIIIB metal or metal cation thereof;

$L_1$ represents an optionally substituted cyclopentadienyl, indenyl or aryl group;

$L_2$ represents one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently represent hydrogen, lower alkyl, aryl, halo or Het;

$R^{19}$ to $R^{30}$ and $R^{43}$ to $R^{48}$, when present, each independently represent hydrogen, lower alkyl, aryl or Het;

$R^{49}$, $R^{54}$ and $R^{55}$, when present, each independently represent hydrogen, lower alkyl or aryl;

$R^{50}$ to $R^{53}$, when present, each independently represent hydrogen, lower alkyl, aryl or Het;

$Y^1$, $Y^2$, $Y^3$, $Y^4$ and $Y^5$, when present, each independently represent oxygen, sulfur or N—$R^{55}$;

n=0 or 1;

and m=0 to 5;

provided that when n=1 then m equals 0, and when n equals 0 then m does not equal 0.

Preferably in a compound of formula III when both $K^1$ represents $-A_3-Q^3(X^5)X^6$ and $E^1$ represents $-A_5-Q^5(X^9)X^{10}$, then $D^1$ represents $-A_4-Q^4(X^7)X^8$.

Preferably, in this embodiment, $R^1$ to $R^{18}$ and $R^{31}$ to $R^{42}$, when present, each independently represent hydrogen, optionally substituted $C_1$ to $C_6$ alkyl, $C_1$-$C_6$ alkyl phenyl (wherein the phenyl group is optionally substituted as defined herein), trifluoromethyl or phenyl (wherein the phenyl group is optionally substituted as defined herein). Even more preferably, $R^1$ to $R^{18}$ and $R^{31}$ to $R^{42}$, when present, each independently represent hydrogen, $C_1$ to $C_6$ alkyl, which is optionally substituted as defined herein, trifluoromethyl or optionally substituted phenyl. Even more preferably, $R^1$ to $R^{18}$ and $R^{31}$ to $R^{42}$, when present each independently represent hydrogen, non-substituted $C_1$ to $C_6$ alkyl or phenyl which is optionally substituted with one or more substituents selected from non-substituted $C_1$ to $C_6$ alkyl or $OR^{19}$ where $R^{19}$ represents hydrogen or unsubstituted $C_1$ to $C_6$ alkyl. More preferably, $R^1$ to $R^{18}$ and $R^{31}$ to $R^{42}$, when present, each independently represent hydrogen or non-substituted $C_1$ to $C_6$ alkyl such as methyl, ethyl, n-propyl, iso-propyl, n-butyl, iso-butyl, tert-butyl, pentyl, hexyl and cyclohexyl, especially methyl. Most preferably, $R^1$ to $R^{18}$ and $R^{31}$ to $R^{42}$ when present, each independently represent non-substituted $C_1$ to $C_6$ alkyl such as methyl, ethyl, n-propyl, iso-propyl, n-butyl, iso-butyl, tert-butyl, pentyl, hexyl and cyclohexyl, especially methyl.

Alternatively, or additionally, one or more of the groups $R^1$ to $R^3$, $R^4$ to $R^6$, $R^7$ to $R^9$, $R^{10}$ to $R^{12}$, $R^{13}$ to $R^{15}$, $R^{16}$ to $R^{18}$, $R^{31}$ to $R^{33}$, $R^{34}$ to $R^{36}$, $R^{37}$ to $R^{39}$ or $R^{40}$ to $R^{42}$ (when present) together with the carbon atom to which they are attached independently may form cyclic alkyl structures such as 1-norbornyl or 1-norbornadienyl.

Alternatively, or additionally, one or more of the groups $R^1$ and $R^2$, $R^4$ and $R^5$, $R^7$ and $R^8$, $R^{10}$ and $R^{11}$, $R^{13}$ and $R^{14}$, $R^{16}$ and $R^{17}$, $R^{31}$ and $R^{32}$, $R^{34}$ and $R^{35}$, $R^{37}$ and $R^{38}$ or $R^{40}$ and $R^{41}$ (when present) together with the carbon atom to which they are attached independently may form a cyclic alkyl structures, preferably a $C_5$ to $C_7$ cyclic alkyl structure such as cyclohexyl and cyclopentyl, and $R^3$, $R^6$, $R^9$, $R^{12}$, $R^{15}$, $R^{18}$, $R^{33}$, $R^{36}$, $R^{39}$ and $R^{42}$ (when present) each independently represent hydrogen, lower alkyl, trifluoromethyl or aryl as defined above, particularly non-substituted $C_1$ to $C_6$ alkyl and hydrogen, especially non-substituted $C_1$ to $C_6$ alkyl.

In an especially preferred embodiment, each of $R^1$ to $R^{18}$ and $R^{31}$ to $R^{42}$, when present, do not represent hydrogen. Suitably, such an arrangement means $Q^1$, $Q^2$, $Q^3$, $Q^4$ and $Q^5$ are bonded to a carbon atom of $X^1$ to $X^{10}$, respectively, which bears no hydrogen atoms.

Preferably, $R^1$, $R^4$, $R^7$, $R^{10}$, $R^{13}$, $R^{16}$, $R^{31}$, $R^{34}$, $R^{37}$ and $R^{40}$ (when present), each represent the same substituent as defined herein; $R^2$, $R^5$, $R^8$, $R^{11}$, $R^{14}$, $R^{17}$, $R^{32}$, $R^{35}$, $R^{38}$ and $R^{41}$ (when present), each represent the same substituent as defined herein; and $R^3$, $R^6$, $R^9$, $R^{12}$, $R^{15}$, $R^{18}$, $R^{33}$, $R^{36}$, $R^{39}$ and $R^{42}$ (when present), each represent the same substituent as defined herein. More preferably $R^1$, $R^4$, $R^7$, $R^{10}$, $R^{13}$, $R^{15}$, $R^{31}$, $R^{34}$, $R^{37}$ and $R^{40}$ (when present) each represent the same $C_1$-$C_6$ alkyl, particularly non-substituted $C_1$-$C_6$ alkyl, such as methyl, ethyl, n-propyl, iso-propyl, n-butyl, iso-butyl, tert-butyl, pentyl, hexyl or cyclohexyl, or trifluoromethyl; $R^2$, $R^5$, $R^8$, $R^{11}$, $R^{14}$, $R^{17}$, $R^{32}$, $R^{35}$, $R^{38}$ and $R^{41}$ (when present), each independently represent the same $C_1$-$C_6$ alkyl as defined above, or trifluoromethyl; and $R^3$, $R^6$, $R^9$, $R^{12}$, $R^{15}$, $R^{18}$, $R^{33}$, $R^{36}$, $R^{39}$ and $R^{42}$ (when present), each independently represent the same $C_1$-$C_6$ alkyl as defined above, or trifluoromethyl. For example: $R^1$, $R^4$, $R^7$, $R^{10}$, $R^{13}$ and $R^{16}$ (when present) each represent methyl; $R^2$, $R^5$, $R^8$, $R^{11}$, $R^{14}$ and $R^{17}$ each represent ethyl (when present); and, $R^3$, $R^6$, $R^9$, $R^{12}$, $R^{15}$ and $R^{18}$ (when present) each represent n-butyl or n-pentyl.

In an especially preferred embodiment each $R^1$ to $R^{18}$ and $R^{31}$ to $R^{42}$ group (when present) represents the same substituent as defined herein. Preferably, each $R^1$ to $R^{18}$ and $R^{31}$ to $R^{42}$ group represents the same $C_1$ to $C_6$ alkyl group, particularly non-substituted $C_1$-$C_6$ alkyl, such as methyl, ethyl, n-propyl, iso-propyl, n-butyl, iso-butyl, tert-butyl, pentyl, hexyl and cyclohexyl, or trifluoromethyl. Most preferably, each $R^1$ to $R^{18}$ and $R^{31}$ to $R^{42}$ group represents non-substituted $C_1$-$C_6$ alkyl, particularly methyl.

The term adamantyl when used herein means an adamantyl group which may be bonded to $Q^1$, $Q^2$, $Q^3$, $Q^4$ and $Q^5$, respectively, in position 1 or 2. Tricyclo[3.3.1.1.{3,7}]decyl is the systematic name for an adamantyl group, suitably $Q^1$, $Q^2$, $Q^3$, $Q^4$ and $Q^5$, respectively, may be bonded to the 1 position or 2 position of one or two tricyclo[3.3.1.1.{3,7}]decyl groups. Preferably, $Q^1$ and $Q^2$, and $Q^3$, $Q^4$ and $Q^5$, when present, is bonded to a tertiary carbon of one or more adamantyl groups. Suitably, when the adamantyl group represents unsubstituted adamantyl, $Q^1$ and $Q^2$, and $Q^3$, $Q^4$ and $Q^5$ when present are preferably bonded to the 1 position of one or more tricyclo[3.3.1.1{3,7}]decyl groups i.e. the carbon atom of the adamantyl group bears no hydrogen atom.

The adamantyl group may optionally comprise, besides hydrogen atoms, one or more substituents selected from lower alkyl, $-OR^{19}$, $-OC(O)R^{20}$, halo, nitro, $-C(O)R^{21}$, $-C(O)OR^{22}$, cyano, aryl, $-N(R^{23})R^{24}$, $-C(O)N(R^{25})R^{26}$, $-C(S)$ $(R^{27})R^{28}$, $-CF_3$, $-P(R^{56})R^{57}$, $-PO(R^{58})(R^{59})$, $-PO_3H_2$, $-PO(OR^{60})(OR^{61})$, or $-SO_3R^{62}$, wherein $R^{19}$, $R^{20}$, $R^{21}$, $R^{22}$, $R^{23}$, $R^{24}$, $R^{25}$, $R^{26}$, $R^{27}$, $R^{28}$, lower alkyl, cyano and aryl are as defined herein and $R^{56}$ to $R^{62}$ each independently represent hydrogen, lower alkyl, aryl or Het.

Suitably, when the adamantyl group is substituted with one or more substituents as defined above, highly preferred substituents include unsubstituted $C_1$ to $C_6$ alkyl, $-OR^{19}$, $-OC(O)R^{20}$, phenyl, $-C(O)OR^{22}$, fluoro, $-SO_3H$, $-N(R^{23})R^{24}$, $-P(R^{56})R^{57}$, $-C(O)N(R^{25})R^{26}$ and $-PO(R^{58})(R^{59})$, $-CF_3$, wherein $R^{19}$ represents hydrogen, unsubstituted $C_1$-$C_8$ alkyl or phenyl, $R^{20}$, $R^{22}$, $R^{23}$, $R^{24}$, $R^{25}$, $R^{26}$ each independently represent hydrogen or unsubstituted $C_1$-$C_8$ alkyl, $R^{56}$ to $R^{53}$, $R^{56}$ each independently represent unsubstituted $C_1$-$C_8$ alkyl or phenyl.

Suitably, the adamantyl group may comprise, besides hydrogen atoms, up to 10 substituents as defined above, preferably up to 5 substituents as defined above, more preferably up to 3 substituents as defined above. Suitably, when the adamantyl group comprises, besides hydrogen atoms, one or more substituents as defined herein, preferably each substituent is identical. Preferred substituents are unsubstituted $C_1$-$C_8$ alkyl and trifluoromethyl, particularly unsubstituted $C_1$-$C_8$ alkyl such as methyl. A highly preferred adamantyl group comprises hydrogen atoms only i.e. the adamantyl group is not substituted.

Preferably, when more than one adamantyl group is present in a compound of formula III, each adamantyl group is identical.

By the term 2-phospha-tricyclo[3.3.1.1.{3,7}]decyl group we mean a 2-phospha-adamantyl group formed by the combination of $X^1$ and $X^2$ together with $Q^2$ to which they are attached, a 2-phospha-adamantyl group formed by the combination of $X^3$ and $X^4$ together with $Q^1$ to which they are attached, a 2-phospha-adamantyl group formed by the combination of $X^5$ and $X^6$ together with $Q^3$ to which they are attached, a 2-phospha-adamantyl group formed by the combination of $X^7$ and $X^8$ together with $Q^4$ to which they are attached and a 2-phospha-adamantyl group formed by the combination of $X^9$ and $X^{10}$ together with $Q^5$ to which they are attached, wherein $Q^1$, $Q^2$, $Q^3$, $Q^4$ and $Q^5$ is in the 2-position of the adamantyl group of which it forms an integral part and each of $Q^1$, $Q^2$, $Q^3$, $Q^4$ and $Q^5$ represents phosphorus.

The 2-phospha-tricyclo[3.3.1.1.{3,7}]decyl group (referred to as 2-phospha-adamantyl group herein) may optionally comprise, beside hydrogen atoms, one or more substituents. Suitable substituents include those substituents as defined herein in respect of the adamantyl group. Highly preferred substituents include lower alkyl, particularly unsubstituted $C_1$-$C_8$ alkyl, especially methyl, trifluoromethyl, —$OR^{19}$ wherein $R^{19}$ is as defined herein particularly unsubstituted $C_1$-$C_8$ alkyl or aryl, and 4-dodecylphenyl. When the 2-phospha-adamantyl group includes more than one substituent, preferably each substituent is identical.

Preferably, the 2-phospha-adamantyl group is substituted on one or more of the 1, 3, 5 or 7 positions with a substituent as defined herein. More preferably, the 2-phospha-adamantyl group is substituted on each of the 1, 3 and 5 positions. Suitably, such an arrangement means the phosphorous atom of the 2-phospha-adamantyl group is bonded to carbon atoms in the adamantyl skeleton having no hydrogen atoms. Most preferably, the 2-phospha-adamantyl group is substituted on each of the 1, 3, 5 and 7 positions. When the 2-phospha-adamantyl group includes more than 1 substituent preferably each substituent is identical. Especially preferred substituents are unsubstituted $C_1$-$C_8$ alkyl and trifluoromethyl, particularly unsubstituted $C_1$-$C_8$ alkyl such as methyl.

Preferably, the 2-phospha-adamantyl group includes additional heteroatoms, other than the 2-phosphorous atom, in the 2-phospha-adamantyl skeleton. Suitable additional heteroatoms include oxygen and sulphur atoms, especially oxygen atoms. More preferably, the 2-phospha-adamantyl group includes one or more additional heteroatoms in the 6, 9 and 10 positions. Even more preferably, the 2-phospha-adamantyl group includes an additional heteroatom in each of the 6, 9 and 10 positions. Most preferably, when the 2-phospha-adamantyl group includes two or more additional heteroatoms in the 2-phospha-adamantyl skeleton, each of the additional heteroatoms are identical. An especially preferred 2-phospha-adamantyl group, which may optionally be substituted with one or more substituents as defined herein, includes an oxygen atom in each of the 6, 9 and 10 positions of the 2-phospha-adamantyl skeleton.

Highly preferred 2-phospha-adamantyl groups as defined herein include 2-phospha-1,3,5,7-tetramethyl-6,9,10-trioxadamantyl group, 2-phospha-1,3,5-trimethyl-6,9,10-trioxadamantyl group, 2-phospha-1,3,5,7-tetra(trifluoromethyl)-6,9,10-trioxadamantyl group, and 2-phospha-1,3,5-tri(trifluoromethyl)-6,9,10-trioxadamantyl group. Most preferably, the 2-phospha-adamantyl is selected from 2-phospha-1,3,5,7-tetramethyl-6,9,10-trioxadamantyl group or 2-phospa-1,3,5,-trimethyl-6,9,10-trioxadamantyl group.

Preferably, when more than one 2-phospha-adamantyl group is present in a compound of formula III, each 2-phospha-adamantyl group is identical.

The above definition of the term "2-phospha-tricyclo [3.3.1.1.{3,7}]decyl group" applies equally to the group when it is present in formula I but wherein $X^n$ in formula III, i.e. $X^1$, $X^2$, $X^3$ . . . $X^{10}$, is denoted $CR^xR^yR^z$, i.e. $CR^1R^2R^3$, . . . $CR^{16}R^{17}R^{18}$, in formula I.

The term congressyl when used herein means a congressyl group (also known as diamantyl group) which may be bonded to $Q^1$, $Q^2$, $Q^3$, $Q^4$ and $Q^5$ respectively. Preferably, $Q^1$ and $Q^2$, and $Q^3$, $Q^4$ and $Q^5$, when present, are bonded to one of the tertiary carbon atoms of the congressyl groups. Suitably, when the congressyl group is unsubstituted, $Q^1$ and $Q^2$, and $Q^3$, $Q^4$ and $Q^5$ when present, are preferably bonded to the 1-position of one or more congressyl groups.

The congressyl group may optionally comprise, beside hydrogen atoms, one or more substituents. Suitable substituents include those substituents as defined herein in respect of the adamantyl group. Highly preferred substituents include unsubstituted $C_1$-$C_6$ alkyl groups, particularly methyl, and trifluoromethyl. Most preferably, the congressyl group is unsubstituted and comprises hydrogen atoms only.

Preferably, when more than one congressyl group is present in a compound of formula III, each congressyl group is identical.

Preferably, where one or more ring systems of formula IIIa, IIIb, IIIc, IIId or IIIe are present in a compound of formula III, $R^{50}$ to $R^{53}$ each independently represent lower alkyl, aryl or Het, which groups are optionally substituted and/or terminated as defined herein. Such an arrangement means $Q^2$, $Q^1$, $Q^3$, $Q^4$ and $Q^5$ of the ring system of formula IIIa to IIIe, respectively, is not bonded to a carbon atom bearing a hydrogen atom. Even more preferably, $R^{50}$ to $R^{53}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, or trifluoromethyl. Even more preferably $R^{50}$ to $R^{53}$ each represent the same group as defined herein, particularly non-substituted $C_1$-$C_6$ alkyl, especially methyl.

Preferably, where one or more ring system of formula IIIa to IIIe are present in a compound of formula III, $R^{49}$ and $R^{54}$ each independently represent optionally substituted $C_1$-$C_6$ alkyl, preferably non-substituted $C_1$-$C_6$ alkyl, phenyl optionally substituted with non-substituted $C_1$-$C_6$ alkyl or $OR^{19}$ where $R^{19}$ represents non-substituted $C_1$-$C_6$ alkyl, trifluoromethyl or hydrogen. More preferably, $R^{49}$ and $R^{54}$ represent the same group as defined herein, especially hydrogen.

Preferably, where one or more ring systems of formula IIIa to IIIe are present in a compound of formula III, $Y^1$ to $Y^5$ are identical. Most preferably, each of $Y^1$ to $Y^5$ represents oxygen. Preferably, where more than one ring system of formula IIIa to IIIe is present in a compound of formula III, each such ring system is identical.

Preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ represents $CR^1(R^2)(R^3)$, $X^2$ represents $CR^4(R^5)(R^6)$, and $X^3$ and $X^4$ together with $Q^1$ to which they are attached form a ring system of formula IIIb or a 2-phospha-adamantyl group;

$X^1$ represents $CR^1(R^2)(R^3)$, $X^2$ represents adamantyl, $X^3$ and $X^4$ together with $Q^1$ to which they are attached form a ring system of formula IIIb or a 2-phospha-adamantyl group;

$X^1$ represents $CR^1(R^2)(R^3)$, $X^2$ represents congressyl, $X^3$ and $X^4$ together with $Q^1$ to which they are attached form a ring system of formula IIIb or a 2-phospha-adamantyl group;

$X^1$ to $X^4$ each independently represent adamantyl;

$X^1$ to $X^4$ each independently represent congressyl;

$X^1$ and $X^2$ each independently represent adamantyl and $X^3$ and $X^4$ each independently represent congressyl;

$X^1$ and $X^3$ independently represent adamantyl and $X^2$ and $X^4$ independently represent congressyl;

$X^1$ and $X^2$ independently represent adamantyl, $X^3$ represents $CR^7(R^8)(R^9)$ and $X^4$ represents $CR^{10}(R^{11})(R^{12})$;

$X^1$ and $X^2$ independently represent congressyl, $X^3$ represents $CR^7(R^8)(R^9)$ and $X^4$ represents $CR^{10}(R^{11})(R^{12})$;

$X^1$ and $X^2$ independently represent adamantyl, and $X^3$ and $X^4$ together with $Q^1$ to which they are attached form a ring system of formula IIIb or a 2-phospha-adamantyl group;

$X^1$ and $X^2$ independently represent congressyl, and $X^3$ and $X^4$ together with $Q^1$ to which they are attached form a ring system of formula IIIb or a 2-phospha-adamantyl group;

$X^1$ and $X^2$ together with $Q^2$ to which they are attached form a ring system of formula IIIa, and $X^3$ and $X^4$ together with $Q^1$ to which they are attached form a ring system of formula IIIb;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Highly preferred embodiments of the present invention include those wherein:

$X^1$ represents $CR^1(R^2)(R^3)$, $X^2$ represents $CR^4(R^5)(R^6)$, $X^3$ represents $CR^7(R^8)(R^9)$ and $X^4$ represents $CR^{10}(R^{11})(R^{12})$;

$X^1$ represents $CR^1(R^2)(R^3)$, $X^2$ represents adamantyl, $X^3$ represents $CR^7(R^8)(R^9)$ and $X^4$ represents adamantyl;

$X^1$ represents $CR^1(R^2)(R^3)$, $X^2$ represents congressyl, $X^3$ represents $CR^7(R^8)(R^9)$ and $X^4$ represents congressyl;

$X^1$ to $X^4$ each independently represent adamantyl;

$X^1$ to $X^4$ each independently represent congressyl;

$X^1$ and $X^2$ together with $Q^2$ to which they are attached form a ring system of formula IIIa, and $X^3$ and $X^4$ together with $Q^1$ to which they are attached form a ring system of formula IIIb;

$X^1$ and $X^2$ together with $Q^2$ to which they are attached form a 2-phospha-adamantyl group, and $X^3$ and $X^4$ together with $Q^1$ to which they are attached form a 2-phospha-adamantyl group;

Preferably in a compound of formula III, $X^1$ is identical to $X^3$ and $X^2$ is identical to $X^4$. More preferably, $X^1$ is identical to $X^3$ and $X^5$, $X^7$ and $X^9$ when present, and $X^2$ is identical to $X^4$ and $X^6$, $X^8$ and $X^{10}$ when present. Even more preferably, $X^1$ to $X^4$ are identical. Most preferably, $X^1$ to $X^4$ are identical to each of $X^6$ to $X^{10}$ when present.

Preferably, in the compound of formula III, $X^1$ and $X^2$ represent identical substituents, $X^3$ and $X^4$ represent identical substituents, $X^5$ and $X^6$ (when present) represent identical substituents, $X^7$ and $X^8$ (when present) represent identical substituents, and $X^9$ and $X^{10}$ (when present) represent identical substituents.

Preferably, in a compound of formula III, $K^1$ represents $-A_3-Q^3(X^5)X^6$, hydrogen, lower alkyl, $-CF_3$, phenyl or lower alkyl phenyl. More preferably, $K^1$ represents $-A_3-Q^3(X^5)X^6$, hydrogen, unsubstituted $C_1-C_6$ alkyl, unsubstituted phenyl, trifluoromethyl or $C_1-C_6$ alkyl phenyl.

In a particular preferred embodiment $K^1$ in a compound of formula III represents hydrogen.

In an alternative embodiment where $K^1$ does not represent hydrogen, $K^1$ represents $-A_3-Q^3(X^5)X^6$. Preferably, $X^5$ is identical to $X^3$ or $X^1$, and $X^6$ is identical to $X^2$ or $X^4$. More preferably, $X^5$ is identical to both $X^3$ and $X^1$, and $X^6$ is identical to both $X^2$ and $X^4$. Even more preferably, $-A_3-Q^3(X^5)X^6$ is identical to either $-A_1-Q^2(X^1)X^2$ or $-A_2-Q^1(X^3)X^4$. Most preferably, $-A_3-Q^3(X^5)X^6$ is identical to both $-A_1-Q_2(X^1)X^2$ and $-A_2-Q^1(X^3)X^4$.

Most preferably, $K^1$ represents hydrogen in a compound of formula III.

Preferably, in the compound of formula III, $D^1$ represents $-A_4-Q^4(X^7)X^8$, hydrogen, lower alkyl, $CF_3$, phenyl or lower alkylphenyl, and $E^1$ represents $-A_5-Q^5(X^9)X^{10}$, hydrogen, lower alkyl, $CF_3$, phenyl or lower alkylphenyl, or $D^1$ and $E^1$ together with the carbons of the cyclopentadienyl ring to which they are attached form an optionally substituted phenyl ring. More preferably, $D^1$ represents $-A_4-Q^4(X^7)X^8$, hydrogen, phenyl, $C_1-C_6$ alkylphenyl, unsubstituted $C_1-C_6$ alkyl, such as methyl, ethyl, propyl, butyl, pentyl and hexyl, or $CF_3$; $E^1$ represents $-A_5-Q^5(X^9)X^{10}$, hydrogen, phenyl, $C_1-C_6$ alkylphenyl, unsubstituted $C_1-C_6$ alkyl such as methyl, ethyl, propyl, butyl, pentyl and hexyl, or $-CF_3$; or both $D^1$ and $E^1$ together with the carbon atoms of the cyclopentadienyl ring to which they are attached form a phenyl ring which is optionally substituted with one or more groups selected from phenyl, $C_1-C_6$ alkylphenyl, unsubstituted $C_1-C_6$ alkyl or $-CF_3$.

Suitably, when $D^1$ and $E^1$ together with the carbon atoms of the cyclopentadienyl ring to which they are attached form an optionally substituted phenyl ring, the metal M or cation thereof is attached to an indenyl ring system.

In a particular preferred embodiment, $D^1$ in a compound of formula III, represents hydrogen.

In an alternative embodiment where $D^1$ does not represent hydrogen, $D^1$ represents $-A_4-Q^4(X^7)X^8$. Preferably $X^8$ is identical to $X^4$ or $X^2$, and $X^7$ is identical to $X^1$ or $X^3$. More preferably, $X^8$ is identical to both $X^4$ and $X^2$, and $X^7$ is identical to $X^1$ and $X^3$. Even more preferably, $-A_4-Q^4(X^7)X^8$ is identical to either $-A_1-Q^2(X^1)X^2$ or $-A_2-Q^1(X^3)X^4$. Most preferably, $-A_4-Q^4(X^7)X^8$ is identical to both $-A_2-Q^1(X^3)X^4$, and $-A_3-Q^3(X^5)X^6$ if present.

In a particular preferred embodiment, $E^1$ in a compound of formula III represents hydrogen.

In an alternative embodiment where $E^1$ does not represent hydrogen, $E^1$ represents $-A_5-Q^5(X^9)X^{10}$. Preferably $X^{10}$ is identical to $X^4$ or $X^2$, and $X^9$ is identical to $X^1$ or $X^3$. More preferably, $X^{10}$ is identical to both $X^4$ and $X^2$, and $X^9$ is identical to $X^1$ and $X^3$. Even more preferably, $-A_5-Q^5(X^9)X^{10}$ is identical to either $-A_1-Q^2(X^1)X^2$ or $-A_2-Q^1(X^3)X^4$. Most preferably, $-A_5-Q^5(X^9)X^{10}$ is identical to both $-A_1-Q_2(X^1)X^2$ and $-A_2-Q^1(X^3)X^4$, and $-A_3-Q^3(X^5)X^6$ and $-A_4-Q^4(X^7)X^8$ if present.

Preferably, in the compound of formula III, when $D^1$ and $E^1$ together with the carbon atoms of the cyclopentadienyl ring to which they are attached do not form an optionally substituted phenyl ring, each of $K^1$, $D^1$ and $E^1$ represent an identical substituent.

In an alternative preferred embodiment, $D^1$ and $E^1$ together with the carbons of the cyclopentadienyl ring to which they are attached form an unsubstituted phenyl ring.

Highly preferred embodiments of compounds of formula III include those wherein:

$K^1$, $D^1$ and $E^1$ are identical substituents as defined herein, particularly where $K^1$, $D^1$ and $E^1$ represent hydrogen;

$K^1$ represents hydrogen, and $D^1$ and $E^1$ together with the carbons of the cyclopentadienyl ring to which they are attached form an unsubstituted phenyl ring;

$K^1$ represents $-A_3-Q^3(X^5)X^6$ as defined herein and both $D^1$ and $E^1$ represent H;

$K^1$ represents -$A_3$-$Q^3(X^5)X^6$ as defined herein and $D^1$ and $E^1$ together with the carbon atoms of the cyclopentadienyl ring to which they are attached form an unsubstituted phenyl ring;
$K^1$ represents -$A_3$-$Q^3(X^5)X^6$, $D^1$ represents -$A_4$-$Q^4(X^7)X^8$ and $E^1$ represents -$A_5$-$Q^5(X^9)X^{10}$.

Especially preferred compounds of formula III include those where both $D^1$ and $E^1$ represent hydrogen or $D^1$ and $E^1$ together with the carbon atoms of the cyclopentadienyl ring to which they are attached form an unsubstituted phenyl ring, particularly those compounds where both $D^1$ and $E^1$ represent hydrogen.

Preferably, in the compound of formula III, $A_1$ and $A_2$, and $A_3$, $A_4$ and $A_5$ (when present), each independently represent $C_1$ to $C_6$ alkylene which is optionally substituted as defined herein, for example with lower alkyl groups. Suitably, $A_1$ and $A_2$, and $A_3$, $A_4$ and $A_5$ (when present) may include a chiral carbon atom. Preferably, the lower alkylene groups which $A_1$ to $A_5$ may represent are non-substituted. A particular preferred lower alkylene, which $A_1$ to $A_5$ may independently represent, is —$CH_2$— or —$C_2H_4$—. Most preferably, each of $A_1$ and $A_2$, and $A_3$, $A_4$ and $A_5$ (when present), represent the same lower alkylene as defined herein, particularly —$CH_2$—.

In the compound of formula III, preferably each $Q^1$ and $Q^2$, and $Q^3$, $Q^4$ and $Q^5$ (when present) are the same. Most preferably, each $Q^1$ and $Q^2$, and $Q^3$, $Q^4$ and $Q^5$ (when present), represents phosphorus.

It will be appreciated by those skilled in the art that the compounds of formula III may function as ligands that coordinate with the Group VIB or Group VIIIB metal or compound thereof in the formation of the catalyst system of the invention. Typically, the Group VIB or Group VIIIB metal or compound thereof coordinates to the one or more phosphorus, arsenic and/or antimony atoms of the compound of formula III. It will be appreciated that the compounds of formula III may be referred to broadly as "metallocenes".

Suitably, when n=1 and $L_1$ represents an optionally substituted cyclopentadienyl or indenyl group, the compounds of formula III may contain either two cyclopentadienyl rings, two indenyl rings or one indenyl and one cyclopentadienyl ring (each of which ring systems may optionally be substituted as described herein). Such compounds may be referred to as "sandwich compounds" as the metal M or metal cation thereof is sandwiched by the two ring systems. The respective cyclopentadienyl and/or indenyl ring systems may be substantially coplanar with respect to each other or they may be tilted with respect to each other (commonly referred to as bent metallocenes).

Alternatively, when n=1 and $L_1$ represents aryl, the compounds of the invention may contain either one cyclopentadienyl or one indenyl ring (each of which ring systems may optionally be substituted as described herein) and one aryl ring which is optionally substituted as defined herein. Suitably, when n=1 and $L_1$ represents aryl then the metal M of the compounds of formula III as defined herein is typically in the form of the metal cation.

In a particularly preferred embodiment of the present invention, in a compound of formula III, n=1, $L_1$ is as defined herein and m=0.

Preferably, when n=1 in the compound of formula III, $L_1$ represents cyclopentadienyl, indenyl or aryl ring each of which rings are optionally substituted by one or more substituents selected from hydrogen, lower alkyl, halo, cyano, nitro, —$OR^{19}$, —$OC(O)R^{20}$, —$C(O)R^{21}$, —$C(O)OR^{22}$, —$N(R^{23})R^{24}$, —$C(O)N(R^{25})R^{26}$, —$C(S)(R^{27})R^{28}$— $SR^{29}$, —$C(O)SR^{30}$, —$CF_3$ or ferrocenyl (by which we mean the cyclopentadienyl, indenyl or aryl ring which $L_1$ may represent is bonded directly to the cyclopentadienyl ring of the ferrocenyl group), wherein $R^{19}$ to $R^{30}$ is as defined herein. More preferably, if the cyclopentadienyl, indenyl or aryl ring which $L_1$ may represent is substituted it is preferably substituted with one or more substituents selected from unsubstituted $C_1$-$C_6$ alkyl, halo, cyano, —$OR^{19}$, —$OC(O)R^{20}$, —$C(O)R^{21}$, —$C(O)OR^{22}$, —$N(R^{23})R^{24}$ where $R^{19}$, $R^{20}$, $R^{21}$, $R^{22}$, $R^{23}$ and $R^{24}$ each independently represent hydrogen or $C_1$-$C_6$ alkyl. Even more preferably, if the cyclopentadienyl, indenyl or aryl ring which $L_1$ may represent is substituted, it is preferably substituted with one or more substituents selected from unsubstituted $C_1$-$C_6$ alkyl.

Preferably, when n=1, $L_1$ represents cyclopentadienyl, indenyl, phenyl or napthyl optionally substituted as defined herein. Preferably, the cyclopentadienyl, indenyl, phenyl or napthyl groups are unsubstituted. More preferably, $L_1$ represents cyclopentadienyl, indenyl or phenyl, each of which rings are unsubstituted. Most preferably, $L_1$ represents unsubstituted cyclopentadienyl.

Alternatively, when n=0, the compounds of the invention contain only one cyclopentadienyl or indenyl ring (each of which ring systems may optionally be substituted as described herein). Such compounds may be referred to as "half sandwich compounds". Preferably, when n=0 then m represents 1 to 5 so that the metal M of the compounds of formula III has an 18 electron count. In other words, when metal M of the compounds of formula III is iron, the total number of electrons contributed by the ligands $L_2$ is typically five.

In a particularly preferred alternative embodiment of the present invention, in a compound of formula III, n=0, $L_2$ is as defined herein and m=3 or 4, particularly 3.

Preferably, when n is equal to zero and m is not equal to zero in a compound of formula III, $L_2$ represents one or more ligands each of which are independently selected from lower alkyl, halo, —CO, —$P(R^{43})(R^{44})R^{45}$ or —$N(R^{46})(R^{47})R^{48}$.

More preferably, $L_2$ represents one or more ligands each of which are independently selected from unsubstituted $C_1$ to $C_4$ alkyl, halo, particularly chloro, —CO, —$P(R^{43})(R^{44})R^{45}$ or —$N(R^{46})(R^{47})R^{48}$, wherein $R^{43}$ to $R^{48}$ are independently selected from hydrogen, unsubstituted $C_1$ to $C_6$ alkyl or aryl, such as phenyl.

Suitably, the metal M or metal cation thereof in the compounds of formula III is typically bonded to the cyclopentadienyl ring(s), the cyclopentadienyl moiety of the indenyl ring(s) if present, the aryl ring if present, and/or the ligands $L_2$ if present. Typically, the cyclopentadienyl ring or the cyclopentadienyl moiety of the indenyl ring exhibits a pentahapto bonding mode with the metal; however other bonding modes between the cyclopentadienyl ring or cyclopentadienyl moiety of the indenyl ring and the metal, such as trihapto coordination, are also embraced by the scope of the present invention.

Most preferably, in a compound of formula III, n=1, m=0 and $L_1$ is defined herein, particularly unsubstituted cyclopentadienyl.

Preferably M represents a Group VIB or VIIIB metal. In other words the total electron count for the metal M is 18.

Preferably, in the compound of formula III, M represents Cr, Mo, Fe, Co or Ru, or a metal cation thereof. Even more preferably, M represents Cr, Fe, Co or Ru or a metal cation thereof. Most preferably, M is selected from a Group VIIIB metal or metal cation thereof. An especially preferred Group VIIIB metal is Fe. Although the metal M as defined herein may be in a cationic form, preferably it carries essentially no residual charge due to coordination with $L_1$ and/or $L_2$ as defined herein.

Especially preferred compounds of formula III include those wherein:

(1) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represents unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(2) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(3) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
each of $R^1$ to $R^{18}$ independently represent unsubstituted $C_1$-$C_6$ alkyl or trifluoromethyl, particularly where each of $R^1$ to $R^{18}$ is identical, especially where each of $R^1$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(4) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$, wherein each of $R^1$ to $R^{12}$ independently represent unsubstituted $C_1$-$C_6$ alkyl or trifluoromethyl, particularly where each of $R^1$ to $R^{12}$ is identical, especially where each of $R^1$ to $R^{12}$ represents unsubstituted $C_1$-$C_6$ alkyl, particularly methyl;
$A_1$ and $A_2$ are the same and represent —$CH_2$—;
$Q^1$ and $Q^2$ both represent phosphorus;
$K^1$ represents hydrogen or $C_1$-$C_6$ alkyl, particularly hydrogen;

$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(5) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;
each of $R^1$ to $R^{12}$ and $R^{37}$ to $R^{42}$ independently represent unsubstituted $C_1$-$C_6$ alkyl or trifluoromethyl, particularly where each of $R^1$ to $R^{12}$ and $R^{37}$ to $R^{42}$ is identical, especially where each of $R^1$ to $R^{12}$ and $R^{37}$ to $R^{42}$ represents unsubstituted $C_1$-$C_6$ alkyl, particularly methyl;
$A_1$ and $A_2$ are the same and represent —$CH_2$—;
$Q^1$, $Q^2$ and $Q^5$ each represent phosphorus;
$D^1$ and $K^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(6) $X^1$ represents $CR^1(R^2)(R^3)$, $X^2$ represents $CR^4(R^5)(R^6)$, $X^3$ represents $CR^7(R^8)(R^9)$, $X^4$ represents $CR^{10}(R^{11})(R^{12})$;
$K^1$ represents —$CH_2$-$Q^3(X^5)X^6$ wherein $X^5$ represents $CR^{13}(R^{14})(R^{15})$ and $X^6$ represents $CR^{16}(R^{17})(R^{18})$;
$D^1$ represents —$CH_2$-$Q^4(X^7)X^8$ wherein $X^7$ represents $CR^{31}(R^{32})(R^{33})$ and $X^8$ represents $CR^{34}(R^{35})(R^{36})$;
$E^1$ represents —$CH_2$-$Q^5(X^9)X^{10}$ wherein $X^9$ represents $CR^{37}(R^{38})(R^{39})$ and $X^{10}$ represents $CR^{40}(R^{41})(R^{42})$;
each of $R^1$ to $R^{18}$ and $R^{31}$ to $R^{42}$ independently represent unsubstituted $C_1$-$C_6$ alkyl or trifluoromethyl, particularly where each of $R^1$ to $R^{18}$ and $R^{31}$ to $R^{42}$ is identical, especially where each of $R^1$ to $R^{18}$ and $R^{31}$ to $R^{42}$ represents unsubstituted $C_1$-$C_6$ alkyl, particularly methyl;
$A_1$ and $A_2$ are the same and represent —$CH_2$—;
$Q^1$, $Q^2$, $Q^3$, $Q^4$ and $Q^5$ each represent phosphorus
M represents Fe;
n=1 and $L_1$ represents cyclopentadienyl, particularly unsubstituted cyclopentadienyl, and m=0.

(7) $X^1$, $X^2$, $X^3$ and $X^4$ independently represent adamantyl, especially where $X^1$ to $X^4$ represent the same adamantyl group;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(8) $X^1$, $X^2$, $X^3$ and $X^4$ independently represent adamantyl, especially where $X^1$ to $X^4$ represent the same adamantyl group;
$K^1$ represents —$CH_2$-$Q^3(X^5)X^6$ wherein $X^5$ and $X^6$ independently represent adamantyl, especially where $X^1$ to $X^6$ represent the same adamantyl group;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(9) $X^1$, $X^2$, $X^3$ and $X^4$ independently represent adamantyl, especially where $X^1$ to $X^4$ represent the same adamantyl group;
  $K^1$ represents —$CH_2$-$Q^3(X^5)X^6$ wherein $X^5$ and $X^6$ independently represent adamantyl, especially where $X^1$ to $X^6$ represent the same adamantyl group;
  $A_1$ and $A_2$ are the same and represent —$CH_2$—;
  $Q^1$, $Q^2$ and $Q^3$ each represent phosphorus;
  $D^1$ and $E^1$ together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(10) $X^1$, $X^2$, $X^3$ and $X^4$ independently represent adamantyl, especially where $X^1$ to $X^4$ represent the same adamantyl group;
  $A_1$ and $A_2$ are the same and represent —$CH_2$—;
  $Q^1$ and $Q^2$ both represent phosphorus;
  $K^1$ represents hydrogen or unsubstituted $C_1$-$C_6$ alkyl, particularly hydrogen;
  $D^1$ and $E^1$ together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(11) $X^1$, $X^2$, $X^3$ and $X^4$ independently represent adamantyl;
  $K^1$ represents —$CH_2$-$Q^3(X^5)X^6$ wherein $X^5$ and $X^6$ independently represent adamantyl;
  $D^1$ represents —$CH_2$-$Q^4(X^7)X^8$ wherein $X^7$ and $X^8$ independently represents adamantyl;
  $E^1$ represents —$CH_2$-$Q^5$ $(X^9)X^{10}$ wherein $X^9$ and $X^{10}$ independently represents adamantyl, especially where $X^1$ to $X^{10}$ represent the same adamantyl group;
  $A_1$ and $A_2$ are the same and represent —$CH_2$—;
  $Q^1$, $Q^2$, $Q^3$, $Q^4$ and $Q^5$ each represent phosphorus;
  M represents Fe;
  n=1 and $L_1$ represents cyclopentadienyl, particularly unsubstituted cyclopentadienyl, and m=0.
(12) $X^1$ and $X^2$ together with $Q^2$ to which they are attached represents 2-phospha-adamantyl;
  $X^3$ and $X^4$ together with $Q^1$ to which they are attached represents 2-phospha-adamantyl;
  $A_1$ and $A_2$ are the same and represent —$CH_2$—;
  $K^1$, $D^1$ and $E^1$ are the same and represent hydrogen or unsubstituted $C_1$-$C_6$ alkyl, particularly hydrogen;
  $Q^1$ and $Q^2$ both represent phosphorus;
  M represents Fe;
  n=1 and $L_1$ represents cyclopentadienyl, particularly unsubstituted cyclopentadienyl, and m=0.
(13) $X^1$ and $X^2$ together with $Q^2$ to which they are attached represents 2-phospha-adamantyl;
  $X^3$ and $X^4$ together with $Q^1$ to which they are attached represents 2-phospha-adamantyl;
  $K^1$ represents —$CH_2$-$Q^3(X^5)X^6$ wherein $X^5$ and $X^6$ together with $Q^3$ to which they are attached represents 2-phospha-adamantyl;
  $A_1$ and $A_2$ are the same and represent —$CH_2$—;
  $Q^1$, $Q^2$ and $Q^3$ each represent phosphorus;
  $D^1$ and $E^1$ are the same and represent hydrogen or unsubstituted $C_1$-$C_6$ alkyl, particularly hydrogen;
  M represents Fe;
  n=1 and $L_1$ represents cyclopentadienyl, particularly unsubstituted cyclopentadienyl, and m=0.
(14) $X^1$ and $X^2$ together with $Q^2$ to which they are attached represents 2-phospha-adamantyl;
  $X^3$ and $X^4$ together with $Q^1$ to which they are attached represents 2-phospha-adamantyl;
  $K^1$ represents —$CH_2$-$Q^3(X^5)X^6$ wherein $X^5$ and $X^6$ together with $Q^3$ to which they are attached represents 2-phospha-adamantyl;
  $A_1$ and $A_2$ are the same and represent —$CH_2$—;
  $Q^1$, $Q^2$ and $Q^3$ each represent phosphorus;
  $D^1$ and $E^1$ together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(15) $X^1$ and $X^2$ together with $Q^2$ to which they are attached represents 2-phospha-adamantyl;
  $X^3$ and $X^4$ together with $Q^1$ to which they are attached represents 2-phospha-adamantyl;
  $A_1$ and $A_2$ are the same and represent —$CH_2$—;
  $Q^1$ and $Q^2$ both represent phosphorus;
  $K^1$ represents hydrogen or unsubstituted $C_1$-$C_6$ alkyl, particularly hydrogen;
  $D^1$ and $E^1$ together with the carbon atoms of the cyclopentadienyl ring to which they are attached form an unsubstituted phenyl ring;
  M represents Fe;
  n=1 and $L_1$ represents cyclopentadienyl, particularly unsubstituted cyclopentadienyl, and m=0.
(16) $X^1$ and $X^2$ together with $Q^2$ to which they are attached represents 2-phospha-adamantyl;
  $X^3$ and $X^4$ together with $Q^1$ to which they are attached represents 2-phospha-adamantyl;
  $K^1$ represents —$CH_2$-$Q^3(X^5)X^6$ wherein $X^5$ and $X^6$ together with $Q^3$ to which they are attached represents 2-phospha-adamantyl;
  $D^1$ represents —$CH_2$-$Q^4(X^7)X^8$ wherein $X^7$ and $X^8$ together with $Q^4$ to which they are attached represents 2-phospha-adamantyl;
  $E^1$ represents —$CH_2$-$Q^5$ $(X^9)X^{10}$ wherein $X^9$ and $X^{10}$ together with $Q^5$ to which they are attached represents 2-phospha-adamantyl;
  $A_1$ and $A_2$ are the same and represent —$CH_2$—;
  $Q^1$, $Q^2$, $Q^3$, $Q^4$ and $Q^5$ each represent phosphorus
  M represents Fe;
  n=1 and $L_1$ represents cyclopentadienyl, particularly unsubstituted cyclopentadienyl, and m=0.
(17) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
  $A_1$ and $A_2$ are the same and represent —$CH_2$—;
  $K^1$, $D^1$ and $E^1$ are the same and represent hydrogen or unsubstituted $C_1$-$C_6$ alkyl, particularly hydrogen;
  $Q^1$ and $Q^2$ both represent phosphorus;
  M represents Fe;
  n=1 and $L_1$ represents cyclopentadienyl, particularly unsubstituted cyclopentadienyl (referred to as puc) and m=0.
(18) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
  $K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from hydrogen, unsubstituted $C_1$-$C_6$ alkyl or $CF_3$ and $R^{49}$ and $R^{54}$ represent hydrogen;
$A_1$ and $A_2$ are the same and represent —$CH_2$—;
$Q^1$, $Q^2$ and $Q^3$ each represent phosphorus;
$D^1$ and $E^1$ are the same and represent hydrogen or $C_1$-$C_6$ alkyl, particularly hydrogen;
M represents Fe;
n=1 and $L_1$ represents cyclopentadienyl, particularly unsubstituted cyclopentadienyl, and m=0.

(19) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(20) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(21) $X^1$ and $X^2$ together with $Q^2$ to which they are attached form a ring system of formula IIIa, $X^3$ and $X^4$ together with $Q^1$ to which they are attached form a ring system of formula IIIb, wherein $Y^1$ and $Y^2$ both represent oxygen, $R^{50}$ to $R^{53}$ are independently selected from unsubstituted $C_1$-$C_6$ alkyl or $CF_3$, and $R^{49}$ and $R^{54}$ represent hydrogen;
$K^1$ represents —$CH_2$-$Q^3(X^5)X^6$ wherein $X^5$ and $X^6$ together with $Q^3$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;
$D^1$ represents —$CH_2$-$Q^4(X^7)X^8$ wherein $X^7$ and $X^8$ together with $Q^4$ to which they are attached form a ring system of formula IIIc, wherein $Y^3$ represents oxygen, $R^{50}$ to $R^{53}$ are independently selected from unsubstituted $C_1$-$C_6$ alkyl or $CF_3$, and $R^{49}$ and $R^{54}$ represent hydrogen;
$E^1$ represents —$CH_2$-$Q^5$ $(X^9)X^{10}$ wherein $X^9$ and $X^{10}$ together with $Q^5$ to which they are attached form a ring system of formula IIIe, wherein $Y^5$ represents oxygen, and $R^{50}$ to $R^{53}$ are independently selected from unsubstituted $C_1$-$C_6$ alkyl or $CF_3$, and $R^{49}$ and $R^{54}$ represent hydrogen;
$A_1$ and $A_2$ are the same and represent —$CH_2$—;
$Q^1$, $Q^2$, $Q^3$, $Q^4$ and $Q^5$ each represent phosphorus;
M represents Fe;
n=1 and $L_1$ represents cyclopentadienyl;
particularly unsubstituted cyclopentadienyl, and m=0.

(22) $X^1$, $X^2$, $X^3$ and $X^4$ independently represent congressyl, especially where $X^1$ to $X^4$ represent the same congressyl group;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(23) $X^1$, $X^2$, $X^3$ and $X^4$ independently represent congressyl, especially where $X^1$ to $X^4$ represent the same congressyl group;
$K^1$ represents —$CH_2$-$Q^3(X^5)X^6$ wherein $X^5$ and $X^6$ independently represent congressyl, especially where $X^1$ to $X^6$ represent the same congressyl group;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(24) $X^1$, $X^2$, $X^3$ and $X^4$ independently represent congressyl, especially where $X^1$ to $X^4$ represent the same congressyl group;
$K^1$ represents —$CH_2$-$Q^3(X^5)X^6$ wherein $X^5$ and $X^6$ independently represent congressyl, especially where $X^1$ to $X^5$ represent the same congressyl group;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(25) $X^1$, $X^2$, $X^3$ and $X^4$ independently represent congressyl, especially where $X^1$ to $X^4$ represent the same congressyl group;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(26) $X^1$, $X^2$, $X^3$ and $X^4$ independently represent congressyl;
$K^1$ represents —$CH_2$-$Q^3(X^5)X^6$ wherein $X^5$ and $X^6$ independently represent congressyl;
$D^1$ represents —$CH_2$-$Q^4(X^7)X^8$ wherein $X^7$ and $X^8$ independently represents congressyl;
$E^1$ represents —$CH_2$-$Q^5$ $(X^9)X^{10}$ wherein $X^9$ and $X^{10}$ independently represents congressyl, especially where $X^1$ to $X^{10}$ represent the same congressyl group;

$A_1$ and $A_2$ are the same and represent —$CH_2$—;
$Q^1$, $Q^2$, $Q^3$, $Q^4$ and $Q^5$ each represent phosphorus;
M represents Fe;
n=1 and $L_1$ represents cyclopentadienyl, particularly unsubstituted cyclopentadienyl, and m=0.

(27) $X^1$ and $X^3$ independently represent adamantyl, especially where $X^1$ and $X^3$ represent the same adamantyl group;
$X^2$ represents $CR^4(R^5)(R^6)$ and $X^4$ represents $CR^{10}(R^{11})(R^{12})$ wherein each of $R^4$, $R^5$, Re, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;
$A_1$ and $A_2$ are the same and represent —$CH_2$—;
$K^1$, $D^1$ and $E^1$ are the same and represent hydrogen or unsubstituted $C_1$-$C_6$ alkyl, particularly hydrogen;
$Q^1$ and $Q^2$ both represent phosphorus;
M represents Fe;
n=1 and $L_1$ represents cyclopentadienyl, particularly unsubstituted cyclopentadienyl, and m=0.

(28) $X^1$ and $X^3$ independently represent adamantyl, especially where $X^1$ and $X^3$ represent the same adamantyl group;
$K^1$ represents —$CH_2$-$Q^3(X^5)X^6$ wherein $X^5$ represents adamantyl, especially where $X^1$, $X^3$ and $X^5$ represent the same adamantyl group;
$X^2$ represents $CR^4(R^5)(R^6)$, $X^4$ represents $CR^{10}(R^{11})(R^{12})$, $X^6$ represents $CR^{16}(R^{17})(R^{18})$, wherein each of $R^4$ to $R^6$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ are the same and represent hydrogen or unsubstituted $C_1$-$C_6$ alkyl, particularly hydrogen;
M represents Fe;
n=1 and $L_1$ represents cyclopentadienyl, particularly unsubstituted cyclopentadienyl, and m=0.

(29) $X^1$ and $X^3$ independently represent adamantyl, especially where $X^1$ and $X^3$ represent the same adamantyl group;
$K^1$ represents —$CH_2$-$Q^3(X^5)X^6$ wherein $X^5$ represents adamantyl, especially where $X^1$, $X^3$ and $X^5$ represent the same adamantyl group;
$X^2$ represents $CR^4(R^5)(R^6)$, $X^4$ represents $CR^{10}(R^{11})(R^{12})$, $X^6$ represents $CR^{16}(R^{17})(R^{18})$, wherein each of $R^4$ to $R^5$, $R^{10}$ to $R^{12}$ and $R^{16}$ to $R^{18}$ independently represent unsubstituted $C_1$-$C_6$ alkyl or trifluoromethyl, particularly where each of $R^4$ to $R^6$, $R^{10}$ to $R^{12}$, and $R^{16}$ to $R^{18}$ is identical, especially where each of $R^4$ to $R^6$, $R^{10}$ to $R^{12}$ and $R^{16}$ to $R^{18}$ represents unsubstituted $C_1$-$C_6$ alkyl, particularly methyl;
$A_1$ and $A_2$ are the same and represent —$CH_2$—;
$Q^1$, $Q^2$ and $Q^3$ each represent phosphorus;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

(30) $X^1$ and $X^3$ independently represent adamantyl, especially where $X^1$ and $X^3$ represent the same adamantyl group;
$X^2$ represents $CR^4(R^5)(R^6)$ and $X^4$ represents $CR^{10}(R^{11})(R^{12})$ wherein each of $R^4$, $R^5$, $R^6$, $R^{10}$, $R^{11}$ and $R^{12}$ independently represent $C_1$-$C_6$ alkyl or trifluoromethyl, particularly where each of $R^4$ to $R^6$ and $R^{10}$ to $R^{12}$ is identical, especially where each of $R^4$ to $R^6$ and $R^{10}$ to $R^{12}$ represents unsubstituted $C_1$-$C_6$ alkyl, particularly methyl;
$A_1$ and $A_2$ are the same and represent —$CH_2$—;
$Q^1$ and $Q^2$ both represent phosphorus;
$K^1$ represents hydrogen or unsubstituted $C_1$-$C_6$ alkyl, particularly hydrogen;
$D^1$ and $E^1$ together with the carbon atoms of the cyclopentadienyl ring to which they are attached form an unsubstituted phenyl ring;
M represents Fe;
n=1 and $L_1$ represents cyclopentadienyl, particularly unsubstituted cyclopentadienyl, and m=0.

Specific but non-limiting examples of bidentate ligands within this embodiment include the following: 1,2-bis-(dimethylaminomethyl)ferrocene, 1,2-bis-(ditertbutylphosphinomethyl)ferrocene, 1-hydroxymethyl-2-dimethylaminomethylferrocene, 1,2-bis-(ditertbutylphosphinomethyl)ferrocene, 1-hydroxymethyl-2,3-bis-(dimethylaminomethyl)ferrocene, 1,2,3-tris-(ditertbutylphosphinomethyl)ferrocene, 1,2-bis-(dicyclohexylphosphinomethyl)ferrocene, 1,2-bis-(di-isobutylphosphinomethyl)ferrocene, 1,2-bis-(dicyclopentylphosphinomethyl)ferrocene, 1,2-bis-(diethylphosphinomethyl)ferrocene, 1,2-bis(di-isopropylphosphinomethyl)ferrocene, 1,2-bis-(diraethylphosphinomethyl)ferrocene, 1,2-bis-(di-(1,3,5,7-tetramethyl-6,9,10-trioxa-2-phospha-adamantylmethyl))ferrocene, 1,2-bis-(dimethylaminomethyl)ferrocene-bismethyl iodide, 1,2-bis(dihydroxymethylphosphinomethyl)ferrocene, 1,2-bis(diphosphinomethyl)ferrocene, 1,2-bis-α,α-(P-(2,2,6,6,-tetramethylphosphinan-4-one))dimethylferrocene, and 1,2-bis-(di-1,3,5,7-tetramethyl-6,9,10-trioxa-2-phospha-adamantylmethyl))benzene. Nevertheless, the skilled person in the art would appreciate that other bidentate ligands can be envisaged without departing from the scope of the invention.

According to a further aspect, the present invention provides a catalyst system capable of catalysing the carbonylation of an ethylenically unsaturated compound, said system comprising:
a) a metal of Group VIB or Group VIIIB or a compound thereof,
b) a bidentate phosphine, arsine, or stibine ligand, preferably a bidentate phosphine ligand, and
c) an acid,
wherein said ligand is present in at least a 2:1 molar excess compared to said metal or said metal in said metal compound, and that said acid is present in at least a 2:1 molar excess compared to said ligand.

For the avoidance of any doubt, it is hereby stated that any of the features and embodiments described hereinbefore are equally applicable to this aspect.

According to a further aspect, the present invention provides a process for the carbonylation of an ethylenically unsaturated compound comprising contacting an ethylenically unsaturated compound with carbon monoxide and a hydroxyl group containing compound in the presence of a catalyst system as defined in the present invention, such as defined in the first aspect of the present invention. Preferably, the process is a liquid phase continuous process comprising the step noted above. Nevertheless, although the process is preferably operated continuously, batch operation is possible.

According to a yet further aspect, the present invention provides a process for the carbonylation of an ethylenically unsaturated compound comprising contacting an ethylenically unsaturated compound with carbon monoxide and a hydroxyl group containing compound in the presence of a catalyst system, said system comprising:
a) a metal of Group VIB or Group VIIIB or a compound thereof,
b) a bidentate phosphine, arsine, or stibine ligand, preferably a bidentate phosphine ligand, and
c) an acid,
wherein said ligand is present in at least a 2:1 molar excess compared to said metal or said metal in said metal compound, and that said acid is present in at least a 2:1 molar excess compared to said ligand.

Suitably, the hydroxyl group containing compound includes water or an organic molecule having a hydroxyl functional group. Preferably, the organic molecule having a hydroxyl functional group may be branched or linear, and comprises an alkanol, particularly a $C_1$-$C_{30}$ alkanol, including aryl alkanols, which may be optionally substituted with one or more substituents selected from lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{28}$ as defined herein. Highly preferred alkanols are $C_1$-$C_8$ alkanols such as methanol, ethanol, propanol, iso-propanol, iso-butanol, t-butyl alcohol, n-butanol, phenol and chlorocapryl alcohol. Although the monoalkanols are most preferred, poly-alkanols, preferably, selected from di-octa ols such as diols, triols, tetra-ols and sugars may also be utilised. Typically, such polyalkanols are selected from 1,2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol.

The amount of alcohol is not critical. Generally, amounts are used in excess of the amount of ethylenically unsaturated compound to be carbonylated. Thus the alcohol may serve as the reaction solvent as well, although, if desired, separate solvents may also be used.

It will be appreciated that the end product of the reaction is determined at least in part by the source of hydroxyl group containing compound used. If water is used as the hydroxyl group containing compound then the end product is the corresponding carboxylic acid, whereas use of an alkanol produces the corresponding ester.

It will also be appreciated that the process of the present invention may start with a catalyst system having components providing molar ratios above or below those claimed but such ratios will progress to values within said ranges claimed during the course of the reaction.

It will of course also be appreciated that the levels of such components present within the catalyst system may change during the process of the invention as further amounts of some or all of the components are added to maintain the usable levels of components within the catalyst system. Some of the components of the catalyst system may drop out of the system during the reaction process and therefore levels may need to be topped-up to maintain levels within the actual catalyst system.

As stated hereinbefore, it will be appreciated by those skilled in the art that the phosphines described herein may function as ligands that coordinate with the Group VIB or Group VIIIB metal or compound, together with the present acid, to form a complex. This complex may represent part of the effective catalyst in the present invention and hence may represent part of the catalyst system defined herein.

Thus, in a further aspect, the present invention provides a complex capable of catalysing the carbonylation of an ethylenically unsaturated compound, said complex obtainable by combining:
a) a metal of Group VIB or Group VIIIB or a compound thereof,
b) a bidentate phosphine, arsine, or stibine ligand, preferably a bidentate phosphine ligand, and
c) an acid,
wherein said ligand is present in at least a 2:1 molar excess compared to said metal or said metal in said metal compound, and that said acid is present in at least a 2:1 molar excess compared to said ligand.

In a yet further aspect, the present invention provides a process for the carbonylation of an ethylenically unsaturated compound with carbon monoxide and a hydroxyl group containing compound in the presence of a complex, said complex as defined above.

In the process according to the present invention, the carbon monoxide may be used in pure form or diluted with an inert gas such as nitrogen, carbon dioxide or a noble gas such as argon. Small amounts of hydrogen, typically less than 5% by volume, may also be present.

The ratio (volume/volume) of ethylenically unsaturated compound to hydroxyl group containing compound may vary between wide limits and suitably lies in the range of 1:0.1 to 1:10, preferably from between 2:1 to 1:2 and up to a large excess of hydroxyl group containing compounds when the latter is also the reaction solvent such as up to a 50:1 excess of hydroxyl group containing compounds.

The molar ratio of the ethylenically unsaturated compound to carbon monoxide is preferably in the range 1:1 to 100:1 more preferably greater than 1:1, even more preferably at least 3:1, especially from 3:1 to 50:1, and most preferably in the range from 3:1 to 15:1.

The amount of the catalyst of the invention used in the carbonylation process of the ethylenically unsaturated compound is not critical. Good results may be obtained when, preferably, the amount of Group VIB or VIIIB metal is in the range $10^{-7}$ to $10^{-1}$ moles per mole of ethylenically unsaturated compound, more preferably, $10^{-6}$ to $10^{-2}$ moles, most preferably $10^{-5}$ to $10^{-2}$ moles per mole of ethylenically unsaturated compound. Preferably, the amount of bidentate compound of formula I or formula III to unsaturated compound is in the range $10^{-7}$ to $10^{-1}$, more preferably, $10^{-6}$ to $10^{-2}$, most preferably, $10^{-5}$ to $10^{-2}$ moles per mole of ethylenically unsaturated compound.

Suitably, although non-essential to the invention, the carbonylation of an ethylenically unsaturated compound as defined herein may be performed in one or more aprotic solvents. Suitable solvents include ketones, such as for example methylbutylketone; ethers, such as for example anisole (methyl phenyl ether), 2,5,8-trioxanonane (diglyme), diethyl ether, dimethyl ether, tetrahydrofuran, diphenylether, diisopropylether and the dimethylether of di-ethylene-glycol; esters, such as for example methylacetate, dimethyladipate methyl benzoate, dimethyl phthalate and butyrolactone;

amides, such as for example dimethylacetamide, N-methylpyrrolidone and dimethyl formamide; sulfoxides and sulphones, such as for example dimethylsulphoxide, di-isopropylsulphone, sulfolane (tetrahydrothiophene-2,2-dioxide), 2-methylsulfolane, diethyl sulphone, tetrahydrothiophene 1,1-dioxide and 2-methyl-4-ethylsulfolane; aromatic compounds, including halo variants of such compounds eg. benzene, toluene, ethyl benzene o-xylene, m-xylene, p-xylene, chlorobenzene, o-dichlorobenzene, m-dichlorobenzene:alkanes, including halo variants of such compounds eg, hexane, heptane, 2,2,3-trimethylpentane, methylene chloride and carbon tetrachloride; nitriles eg. benzonitrile and acetonitrile.

Very suitable are aprotic solvents having a dielectric constant that is below a value of 50, more preferably in the range of 3 to 8, at 298.15 K and $1 \times 10^5$ Nm$^{-2}$. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, 76$^{th}$ edition, edited by David R. Lide et al, and published by CRC press in 1995, and are usually quoted for a temperature of about 20° C. or 25° C., i.e. about 293.15 k or 298.15 K, and atmospheric pressure, i.e. about $1 \times 10^5$ Nm$^{-2}$, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the hydroxyl group containing compound is an alkanol, an aprotic solvent will be generated by the reaction as the ester carbonylation product of the ethylenically unsaturated compound, carbon monoxide and the alkanol is an aprotic solvent.

The process may be carried out in an excess of aprotic solvent, i.e. at a ratio (v/v) of aprotic solvent to hydroxyl group containing compound of at least 1:1. Preferably, this ratio ranges from 1:1 to 10:1 and more preferably from 1:1 to 5:1. Most preferably the ratio (v/v) ranges from 1.5:1 to 3:1.

Despite the a foregoing it is preferred that the reaction is carried out in the absence of any external added aprotic solvent i.e. an aprotic solvent not generated by the reaction itself.

The catalyst compounds of the present invention may act as a "heterogeneous" catalyst or a "homogeneous" catalyst.

By the term "homogeneous" catalyst we mean a catalyst, i.e. a compound of the invention, which is not supported but is simply admixed or formed in-situ with the reactants of the carbonylation reaction (e.g. the ethylenically unsaturated compound, the hydroxyl containing compound and carbon monoxide), preferably in a suitable solvent as described herein.

By the term "heterogeneous" catalyst we mean a catalyst, i.e. the compound of the invention, which is carried on a support.

Thus according to a further aspect, the present invention provides a process for the carbonylation of ethylenically unsaturated compounds as defined herein wherein the process is carried out with the catalyst comprising a support, preferably an insoluble support.

Preferably, the support comprises a polymer such as a polyolefin, polystyrene or polystyrene copolymer such as a divinylbenzene copolymer or other suitable polymers or copolymers known to those skilled in the art; a silicon derivative such as a functionalised silica, a silicone or a silicone rubber; or other porous particulate material such as for example inorganic oxides and inorganic chlorides.

Preferably the support material is porous silica which has a surface area in the range of from 10 to 700 m$^2$/g, a total pore volume in the range of from 0.1 to 4.0 cc/g and an average particle size in the range of from 10 to 500 µm. More preferably, the surface area is in the range of from 50 to 500 m$^2$/g, the pore volume is in the range of from 0.5 to 2.5 cc/g and the average particle size is in the range of from 20 to 200 µm. Most desirably the surface area is in the range of from 100 to 400 m$^2$/g, the pore volume is in the range of from 0.8 to 3.0 cc/g and the average particle size is in the range of from 30 to 100 µm. The average pore size of typical porous support materials is in the range of from 10 to 1000 Å. Preferably, a support material is used that has an average pore diameter of from 50 to 500 Å, and most desirably from 75 to 350 Å. It may be particularly desirable to dehydrate the silica at a temperature of from 100° C. to 800° C. anywhere from 3 to 24 hours.

Suitably, the support may be flexible or a rigid support, the insoluble support is coated and/or impregnated with the compounds of the process of the invention by techniques well known to those skilled in the art.

Alternatively, the compounds of the process of the invention are fixed to the surface of an insoluble support, optionally via a covalent bond, and the arrangement optionally includes a bifunctional spacer molecule to space the compound from the insoluble support.

The compounds of the invention may be fixed to the surface of the insoluble support by promoting reaction of a functional group present in the compound of formula I or III, for example a substituent K, D, Z and E (or K$^1$, D$^1$ and E$^1$) of the aryl moiety, with a complimentary reactive group present on or previously inserted into the support. The combination of the reactive group of the support with a complimentary substituent of the compound of the invention provides a heterogeneous catalyst where the compound of the invention and the support are linked via a linkage such as an ether, ester, amide, amine, urea, keto group.

The choice of reaction conditions to link a compound of the process of the present invention to the support depend upon the ethylenically unsaturated compound and the groups of the support. For example, reagents such as carbodiimides, 1,1'-carbonyldiimidazole, and processes such as the use of mixed anhydrides, reductive amination may be employed.

According to a further aspect, the present invention provides the use of the process of any aspect of the invention wherein the catalyst is attached to a support.

Conveniently, the process of the invention may be carried out by dissolving the Group VIB or VIIIB metal or compound thereof as defined herein in a suitable solvent such as one of the hydroxyl group containing compounds or aprotic solvents previously described (a particularly preferred solvent would be the ester or acid product of the specific carbonylation reaction e.g. Methyl propionate for ethylene carbonylation) and subsequently admixing with a compound of formula I or III as defined herein and an acid.

The carbon monoxide may be used in the presence of other gases which are inert in the reaction. Examples of such gases include hydrogen, nitrogen, carbon dioxide and the noble gases such as argon.

Suitable Group VIB or VIIIB metals or a compound thereof which may be combined with a compound of formula I or III include cobalt, nickel, palladium, rhodium, platinum, chromium, molybdenum and tungsten, preferably include cobalt, nickel, palladium, rhodium and platinum. Preferably, component a) is a Group VIIIB metal or a compound thereof. Preferably, the metal is a Group VIIIB metal, such as palladium. Preferably, the Group VIIIB metal is palladium or a compound thereof. Thus, component a) is preferably palladium or a compound thereof. Suitable compounds of such Group VIB or VIIIB metals include salts of such metals with, or compounds comprising weakly coordinated anions derived from, nitric acid; sulphuric acid; lower alkanoic (up to $C_{12}$) acids such as acetic acid and propionic acid; sulphonic acids such as methane sulphonic acid, chlorosulphonic acid, fluorosulphonic acid, trifluoromethane sulphonic acid, benzene sulphonic acid, naphthalene sulphonic acid, toluene sulphonic acid, e.g. p-toluene sulphonic acid, t-butyl sulphonic acid, and 2-hydroxypropane sulphonic acid; sulphonated ion exchange resins; perhalic acid such as perchloric acid; halogenated carboxylic acids such as trichloroacetic acid and trifluoroacetic acid; orthophosphoric acid; phosphonic acids such as benzenephosphonic acid; and acids derived from interactions between Lewis acids and Broensted acids. Other sources which may provide suitable anions include the optionally halogenated tetraphenyl borate derivatives, e.g. perfluorotetraphenyl borate. Additionally, zero valent palladium complexes particularly those with labile ligands, e.g. triphenylphosphine or alkenes such as dibenzylideneacetone or styrene or tri(dibenzylideneacetone)dipalladium may be used. Nevertheless, an acid is present in the catalyst system as set out hereinbefore, even if other sources of anion such as those noted above are also present.

Thus, the acid is selected from an acid having a pKa measured in aqueous solution at 18° C. of less than 4, more preferably less than 3, most preferably less than 2. Suitable acids include the acids listed supra. Preferably, the acid is not a carboxylic acid, more preferably the acid is either a sulphonic acid, or some other non-carboxylic acid such as those selected from the list consisting of perchloric acid, phosphoric acid, methyl phosphonic acid, sulphuric acid, and sulphonic acids, even more preferably a sulphonic acid or other non-carboxylic acid (selected from the list above) having a pKa measured in aqueous solution at 18° C. of less than 2, yet even more preferably a sulphonic acid having a pKa measured in aqueous solution at 18° C. of less than 2, still more preferably the acid is selected from the list consisting of the following sulphonic acids: methanesulphonic acid, trifluoromethanesulphonic acid, tert-butanesulphonic acid, p-toluenesulphonic acid, 2-hydroxypropane-2-sulphonic acid, and 2,4,6-trimethylbenzenesulphonic acid, most preferably the acid is methanesulphonic acid.

As mentioned, the catalyst system of the present invention may be used homogeneously or heterogeneously. Preferably, the catalyst system is used homogeneously.

The catalyst system of the present invention is preferably constituted in the liquid phase which may be formed by one or more of the reactants or by the use of a suitable solvent.

The molar ratio of the amount of ethylenically unsaturated compound used in the reaction to the amount of hydroxyl providing compound is not critical and may vary between wide limits, e.g. from 0.001:1 to 100:1 mol/mol.

The product of the carbonylation reaction using the ligand of the invention may be separated from the other components by any suitable means. However, it is an advantage of the present process that significantly fewer by-products are formed thereby reducing the need for further purification after the initial separation of the product as may be evidenced by the generally significantly higher selectivity. A further advantage is that the other components which contain the catalyst system which may be recycled and/or reused in further reactions with minimal supplementation of fresh catalyst.

Preferably, the carbonylation is carried out at a temperature of between −10 to 150° C., more preferably 0° C. to 140° C., even more preferably 15° C. to 140° C., most preferably 20° C. to 120° C. An especially preferred temperature is one chosen between 80° C. to 120° C. Advantageously, the carbonylation can be carried out at moderate temperatures, it is particularly advantageous to be able to carry out the reaction at room temperature (20° C.).

Preferably, when operating a low temperature carbonylation, the carbonylation is carried out between −30° C. to 49° C., more preferably, −10° C. to 45° C., still more preferably 0° C. to 45° C., even more preferably 10° C. to 45° C., most preferably 15° C. to 45° C. Especially preferred is a range of 15 to 35° C.

Preferably, the carbonylation is carried out at a CO partial pressure of between $0.80 \times 10^5$ N·m$^{-2}$–$90 \times 10^5$ N·m$^{-2}$, more preferably $1 \times 10^5$ N·m$^{-2}$–$65 \times 10^5$ N·m$^{-2}$, most preferably $1$–$30 \times 10^5$ N·m$^{-2}$. Especially preferred is a CO partial pressure of 5 to $20 \times 10^5$ N·m$^{-2}$.

Preferably, a low pressure carbonylation is also envisaged. Preferably, when operating a low pressure carbonylation the carbonylation is carried out at a CO partial pressure of between 0.1 to $5 \times 10^5$ N·m$^{-2}$, more preferably 0.2 to $2 \times 10^5$ N·m$^{-2}$, most preferably 0.5 to $1.5 \times 10^5$ N·m$^{-2}$.

The ethylenically unsaturated compounds may be substituted or non-substituted with groups as defined above for the "aryl" group above. Particularly suitable substituents include alkyl and aryl groups as well as groups containing heteroatoms such as halides, sulphur, phosphorus, oxygen and nitrogen. Examples of substituents include chloride, bromide, iodide and hydroxy, alkoxy, carboxy, amino, amido, nitro, cyano, thiol or thioalkoxy groups. Suitable ethylenically unsaturated compounds include ethene, propene, hexene, vinyl compounds such as vinyl acetates, heptene, octene, nonene, decene, undecene, dodecene, etc up to $C_{30}$, i.e. having from 2 to 30 carbon atoms, which may be linear or branched, cyclic or uncyclic or part cyclic and in which the double bond may take any suitable position in the carbon chain and which includes all stereisomers thereof.

Moreover, the unsaturated compound may have one or more unsaturated bonds and therefore, for example, the range of ethylenically unsaturated compounds extends to dienes. The unsaturated bond(s) may be internal or terminal, the catalyst system of the invention being particularly advantageous in the conversion of internal olefins.

Particularly preferred are olefins having from 2 to 22 carbon atoms per molecule, such as ethene, propene, 1-butene, 2-butene, isobutene, pentenes, hexenes, octenes, e.g. oct-2-ene, oct-3-ene, oct-4-ene, decenes and dodecenes, triisobutylene, tripropylene, internal $C_{14}$ olefins, and internal $C_{15}$-$C_{18}$ olefins, 1,5-cyclooctadiene, cyclododecene, methyl pentenoate and pentene nitriles, e.g. pent-2-ene nitrile.

The ethylenically unsaturated compound is preferably an alkene having 1 to 3 carbon-carbon double bonds per molecule. Non-limiting examples of suitable dienes include the following: 1,3-butadiene, 2-methyl-1,3-butadiene, 1,5- cyclooctadiene, 1,3-cyclohexadiene, 2,4-heptadiene, 1,3-pentadiene, 1,3-hexadiene, particularly 1,3-butadiene.

Another preferred category of unsaturated compounds consists of unsaturated esters of carboxylic acids and esters of unsaturated carboxylic acids. For example, the starting material may be a vinyl ester of a carboxylic acid such as acetic acid or propanoic acid, or it may be an alkyl ester of an unsaturated acid, such as the methyl or ethyl ester of acrylic acid or methacrylic acid.

A further preferred category of unsaturated compounds consists of cycloalkadienes, which will ordinarily refuse carbonylation. For example, the starting material may be dicyclopentadiene or norbornadiene, to give diesters, diamides or diacids, etc., which may find subsequent use as monomers in polymerisation reactions.

The use of stabilising compounds with the catalyst system may also be beneficial in improving recovery of metal which has been lost from the catalyst system. When the catalyst system is utilized in a liquid reaction medium such stabilizing compounds may assist recovery of the Group VI or VIIIB metal.

Preferably, therefore, the catalyst system includes in a liquid reaction medium a polymeric dispersant dissolved in a liquid carrier, said polymeric dispersant being capable of stabilising a colloidal suspension of particles of the Group VI or VIIIB metal or metal compound of the catalyst system within the liquid carrier.

The liquid reaction medium may be a solvent for the reaction or may comprise one or more of the reactants or reaction products themselves. The reactants and reaction products in liquid form may be miscible with or dissolved in a solvent or liquid diluent.

The polymeric dispersant is soluble in the liquid reaction medium, but should not significantly increase the viscosity of the reaction medium in a way which would be detrimental to reaction kinetics or heat transfer. The solubility of the dispersant in the liquid medium under the reaction conditions of temperature and pressure should not be so great as to deter significantly the adsorption of the dispersant molecules onto the metal particles.

The polymeric dispersant is capable of stabilising a colloidal suspension of particles of said Group VI or VIIIB metal or metal compound within the liquid reaction medium such that the metal particles formed as a result of catalyst degradation are held in suspension in the liquid reaction medium and are discharged from the reactor along with the liquid for reclamation and optionally for re-use in making further quantities of catalyst. The metal particles are normally of colloidal dimensions, e.g. in the range 5-100 nm average particle size although larger particles may form in some cases. Portions of the polymeric dispersant are adsorbed onto the surface of the metal particles whilst the remainder of the dispersant molecules remain at least partially solvated by the liquid reaction medium and in this way the dispersed Group VI or VIIIB metal particles are stabilised against settling on the walls of the reactor or in reactor dead spaces and against forming agglomerates of metal particles which may grow by collision of particles and eventually coagulate. Some agglomeration of particles may occur even in the presence of a suitable dispersant but when the dispersant type and concentration is optimised then such agglomeration should be at a relatively low level and the agglomerates may form only loosely so that they may be broken up and the particles redispersed by agitation.

The polymeric dispersant may include homopolymers or copolymers including polymers such as graft copolymers and star polymers.

Preferably, the polymeric dispersant has sufficiently acidic or basic functionality to substantially stabilise the colloidal suspension of said Group VI or VIIIB metal or metal compound.

By substantially stabilise is meant that the precipitation of the Group VI or VIIIB metal from the solution phase is substantially avoided.

Particularly preferred dispersants for this purpose include acidic or basic polymers including carboxylic acids, sulphonic acids, amines and amides such as polyacrylates or heterocycle, particularly nitrogen heterocycle, substituted polyvinyl polymers such as polyvinyl pyrrolidone or copolymers of the aforesaid.

Examples of such polymeric dispersants may be selected from polyvinylpyrrolidone, polyacrylamide, polyacrylonitrile, polyethylenimine, polyglycine, polyacrylic acid, polymethacrylic acid, poly(3-hydroxybutyricacid), poly-L-leucine, poly-L-methionine, poly-L-proline, poly-L-serine, poly-L-tyrosine, poly(vinylbenzenesulphonic acid) and poly (vinylsulphonic acid).

Preferably, the polymeric dispersant incorporates acidic or basic moieties either pendant or within the polymer backbone. Preferably, the acidic moieties have a dissociation constant ($pK_a$) of less than 6.0, more preferably, less than 5.0, most preferably less than 4.5. Preferably, the basic moieties have a base dissociation constant ($pK_b$) being of less than 6.0, more preferably less than 5.0 and most preferably less than 4.5, $pK_a$ and $pK_b$ being measured in dilute aqueous solution at 25° C.

Suitable polymeric dispersants, in addition to being soluble in the reaction medium at reaction conditions, contain at least one acidic or basic moiety, either within the polymer backbone or as a pendant group. We have found that polymers incorporating acid and amide moieties such as polyvinylpyrollidone (PVP) and polyacrylates such as polyacrylic acid (PAA) are particularly suitable. The molecular weight of the polymer which is suitable for use in the invention depends upon the nature of the reaction medium and the solubility of the polymer therein. We have found that normally the average molecular weight is less than 100,000. Preferably, the average molecular weight is in the range 1,000-200,000, more preferably, 5,000-100,000, most preferably, 10,000-40,000 e.g. Mw is preferably in the range 10,000-80,000, more preferably 20,000-60,000 when PVP is used and of the order of 1,000-10,000 in the case of PAA.

The effective concentration of the dispersant within the reaction medium should be determined for each reaction/catalyst system which is to be used.

The dispersed Group VI or VIIIB metal may be recovered from the liquid stream removed from the reactor e.g. by filtration and then either disposed of or processed for re-use as a catalyst or other applications. In a continuous process the liquid stream may be circulated through an external heat-exchanger and in such cases it may be convenient to locate filters for the palladium particles in these circulation apparatus.

Preferably, the polymer:metal mass ratio in g/g is between 1:1 and 1000:1, more preferably, between 1:1 and 400:1, most preferably, between 1:1 and 200:1. Preferably, the polymer:metal mass ratio in g/g is up to 1000, more preferably, up to 400, most preferably, up to 200.

According to a further aspect there is provided a reaction medium comprising one or more reactants, and a catalyst system comprising, or obtainable by combining, at least a Group VIB or VIIIB metal or metal compound, a bidentate phosphine, arsine, or stibine ligand, and an acid, as defined herein, wherein said ligand is present in at least a 2:1 molar excess compared to said metal or said metal in said metal compound, and that said acid is present in at least a 2:1 molar excess compared to said ligand.

Preferably, said reaction medium is a liquid-phase reaction medium, more preferably a liquid-phase continuous-system reaction system.

Preferably, within said reaction medium, the amount of free acid present in the medium, that is acid which is not directly combined with the phosphine ligand, is greater than 500 ppm, more preferably greater than 1000 ppm, most preferably greater than 2000 ppm.

According to a further aspect the invention provides a process for preparing the catalyst systems of the invention comprising combining components a), b) and c) as defined herein, preferably in the aforementioned ratios.

According to a yet further aspect the present invention provides the use of a system comprising, or obtainable by combining:

a) a metal of Group VIB or Group VIIIB or a compound thereof, b) a bidentate phosphine, arsine, or stibine ligand, preferably a bidentate phosphine ligand, and c) an acid, wherein said ligand is present in at least a 2:1 molar excess compared to said metal or said metal in said metal compound, and that said acid is present in at least a 2:1 molar excess compared to said ligand, as a catalyst in the carbonylation of an ethylenically unsaturated compound, preferably the liquid-phase carbonylation of an ethylenically unsaturated compound, more preferably the liquid-phase continuous-system carbonylation of an ethylenically unsaturated compound.

For the avoidance of any doubt, each and every feature described hereinbefore is equally applicable to any or all of the various aspects of the present invention as set out herein, unless such features are incompatible with the particular aspect or are mutually exclusive.

All documents mentioned herein are incorporated by reference thereto.

The following examples further illustrate the present invention. These examples are to be viewed as being illustrative of specific materials falling within the broader disclosure presented above and are not to be viewed as limiting the broader disclosure in any way.

Example 1

Preparation of 1,2 bis(diadamantylphosphinomethyl)benzene

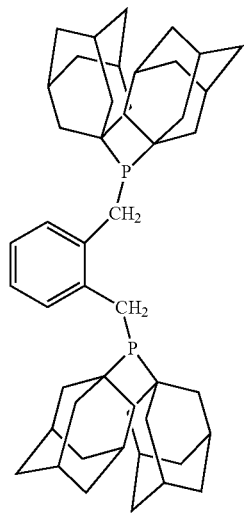

1,2 bis(diadamantylphosphinomethyl) benzene (Method 1)

The preparation of this ligand was carried out as follows.

1.1 Preparation of (1-Ad)$_2$P(O)Cl

Phosphorous trichloride (83 cm$^3$, 0.98 mol) was added rapidly via cannula to a combination of aluminium chloride (25.0 g, 0.19 mol) and adamantane (27.2 g, 0.20 mol) affording a tan suspension. The reaction was heated to reflux. After 10 mins, a yellow-orange suspension was formed. The reaction was refluxed for a total of 6 h. The excess PCl$_3$ was removed by distillation at atmospheric pressure (BP 75° C.). On cooling to ambient temperature, an orange solid was formed. Chloroform (250 cm$^3$) was added yielding an orange suspension, which was cooled to 0° C. Water (150 cm$^3$) was added slowly: initially the suspension viscosity increased, but on full addition of water the viscosity lessened. From this point the reaction was no longer kept under an atmosphere of Ar. The suspension was Buchner filtered to remove the yellow-orange solid impurity. The filtrate consisted of a two phase system. The lower phase was separated using a separating funnel, dried over MgSO$_4$ and Buchner filtered. The volatiles were removed via rotary evaporation, drying finally in-vacuo, affording an off-white powder. Yield 35.0 g, 99%. $^{31}$P NMR: δ=85 ppm, 99% pure. FW=352.85.

1.2 Preparation of (1-Ad)$_2$PH

LiAlH$_4$ (2.54 g, 67.0 mmol) was added over 90 minutes to a chilled (−10° C.) solution of (1-Ad)$_2$P(O)Cl (10.00 g, 28.3 mmol) in THF. (120 cm$^3$). The reaction was allowed to warm to ambient temperature then stirred for 20 h. The grey suspension was cooled to −10° C. HCl (aq., 5 cm$^3$ c. HCl in 50 cm$^3$ degassed water) was added slowly via syringe (initially very slowly due to exotherm of reaction), yielding a two phase system, with some solid material in the lower phase. Further HCl (~5 cm$^3$ c. HCl) was added to improve the separation of the layers. The upper phase was removed via flat ended cannula, dried over MgSO$_4$ and filtered via cannula. The volatiles were removed in-vacuo affording the product as a white powder, isolated in the glovebox. Yield 6.00 g, 70%. $^{31}$P NMR: δ=17 ppm, 100% pure. FW=302.44.

1.3 Preparation of (1-Ad)$_2$PCl

A solution of Ad$_2$PH (10.5 g, 34.7 mmol) and DBU (6.12 cm$^3$, 40.9 mmol) in toluene (250 cm$^3$) was chilled to −10° C. Phosgene solution (30.0 cm$^3$, 56.7 mmol, was added slowly via cannula, transferring via a measuring cylinder. This afforded a highly viscous pale yellow suspension. Additional toluene (100 cm$^3$) was added via cannula to lessen the viscosity and ease the stirring. The reaction was filtered via cannula affording a yellow filtrate. The residue was washed with additional toluene (2×100 cm$^3$) and the washings combined with the original filtrate. The volatiles were removed in-vacuo affording a pale yellow solid, which was washed with pentane (2×30 cm$^3$, washings practically colourless). The product was dried in-vacuo and isolated in the glovebox as a lemon yellow powder. Yield 7.84 g, 67%. $^{31}$P NMR: δ=139 ppm, 99+% pure. FW=336.88.

1.4 Preparation of 1,2-bis(di-1-adamantylphosphinomethyl)benzene 1.4.1 Preparation of DI-SODIO-ORTHO-XYLENE(DISOD)

Bu$''$Li (2.5 M in hexanes, 11.28 cm$^3$, 28.2 mmol) was added dropwise via syringe over 15 minutes to a stirred suspension of NaOBu$^t$ (crushed, 2.71 g, 28.2 mmol), o-xylene (1.15 cm$^3$, 9.4 mmol) and N,N,N',N'-tetramethyl ethylene diamine (TMEDA) (4.26 cm$^3$, 28.2 mmol) in heptane (100 cm$^3$). The reaction was heated at 60° C. for 2 h, then allowed to cool/settle, affording a bright orange solid (DISOD) and pale yellow solution. The solution was removed via cannula filtration and the solid washed with additional heptane (50 cm$^3$) and dried in-vacuo. 90% yield assumed, 8.47 mmol.

1.4.2 Reaction of DI-SODIO-ORTHO-XYLENE with 2 equiv (1-Ad)$_2$PCl

A suspension of DISOD (8.47 mmol) in Et$_2$O (100 cm$^3$) was prepared at −78° C. A suspension of Ad$_2$PCl (5.70 g, 16.9 mmol) in Et$_2$O (120 cm$^3$) was stirred rapidly at −78° C. and added via wide-bore cannula to the DISOD suspension. The reaction was allowed to warm to ambient temperature and stirred for 18 h, affording a pale yellow turbid solution. Water (degassed, 100 cm$^3$) added via cannula affording a two phase system, with a great deal of white solid present (product) due to the low solubility of this material. The upper phase (Et$_2$O) was removed via cannula. The solid in the aqueous phase was extracted using dichloromethane (200 cm$^3$), forming two clear phases. The lower phase (CH$_2$Cl$_2$) was removed via cannula and combined with the original Et$_2$O phase. The volatiles were removed in-vacuo yielding a slightly sticky solid. The solid was washed with pentane (200 cm$^3$) with attrition being performed, the washings being removed via cannula filtration. The white solid was dried in-vacuo and isolated in the glovebox as a friable white powder. Yield 3.5 g, 59%. FW=707.01.

$^{31}$P {$^{1}$H} NMR data: δ 24 ppm.

$^{1}$H NMR data: (400 MHz, CDCl$_3$, 298 K) δ 7.59-7.50 (m, 2H, Ar—H), 7.09-6,99 (m, 2H, Ar—H), 3.01 (d, 4H, $^2J_{PH}$=3.2 Hz, CH$_2$), 2.07-1.57 (m, 60H, C$_{10}$H$_{15}$) ppm.

$^{13}$C {$^{1}$H} NMR data: (100 MHz, CDCl$_3$, 298 K) Γ 139.4 (dd, $J_{PC}$=10.7 Hz, $J_{PC}$=2.3 Hz, Ar—C), 131.0 (d, $J_{PC}$=16.8 Hz, Ar—C), 125.0 (s, Ar—C), 41.1 (d, $^2J_{PC}$=10.7 Hz, Ad-C$^2$), 37.2 (s, Ad-C$^4$), 36.9 (d, $^1J_{PC}$=22.9 Hz, Ad-C$^1$), 28.8 (d, $^3J_{PC}$=7.6 Hz, Ad-C$^3$), 22.0 (dd, $^1J_{PC}$=22.9 Hz, $^4J_{PC}$=3.1 Hz, CH$_2$).

Example 2

Preparation of 1,2 bis(diadamantylphosphinomethyl)benzene (method 2)

2.1 Di-1-adamantyl phosphinic chloride was prepared in accordance with the method of Example 1.1.

2.2 Di-1-adamantyl phosphine was prepared in accordance with the method of Example 1.2.

2.3 (Di-1-adamantyl phosphine)trihydro boron. Borane (THP) adduct (10 cm$^3$, 10 mmol) was added to stirred solution of di-1-adamantyl phosphine (1.36 g, 4.5 mmol) in THP (30 cm$^3$). Stirring for a further 5 hrs afforded a slightly turbid solution. The volatiles were then removed in-vacuo to yield the product as a pure white solid. Yield: 1.39 g, 98%, 99% pure. FW: 315.25. $^{31}$P NMR: δ 41 ppm (d, $J_{PB}$ 64 Hz).

2.4 Synthesis of 1,2 bis(di-1-adamantylphosphor(borane)methyl)benzene via deprotonation with $^{sec}$BuLi and reaction with αα dichloro o-xylene. To a stirred, cooled (−78°) THF solution (60 cm$^3$) of di-1-adamantyl phosphine trihydroboron (5 g, 15.8 mmol), was slowly added (via syringe) $^{sec}$BuLi (12.3 cm$^3$, 16.6 mmol), upon full addition the solution had a noticeable yellow colouration. The solution was stirred for 30 minutes at −78° and then allowed to warm to room temperature and stir for a further 120 minutes. The solution was then cooled to −78° and a THF solution (20 cm$^3$) of αα dichloro o-xylene was added via cannula. The solution was then allowed to warm to room temperature and stirred for 15 hrs. The volatiles where then removed in-vacuo. No further work up was required as LiCl and excess organics are removed during the deprotection procedure. Yield: 100% 85% pure.

$^{31}$P {$^{1}$H} NMR (CDCl$_3$, 298K) δ (d, br) 41 ppm.

$^{11}$B {$^{1}$H} NMR δ −43 ppm (d, $J_{BP}$ 44 Hz)

$^{1}$H NMR (CDCl$_3$, 298K) δ 7.8-7.50 ppm (m, br Ar—H), δ 7.49-7.00 ppm (m, br Ar—H), δ 3.3 ppm (d, CH$_2$), δ 2.2-1.2 ppm (m, C$_{10}$H$_{15}$)

2.5 Synthesis of 1,2-bis(di-adamantylphosphinomethyl)benzene via deprotection of 1,2 bis(di-adamantylphosphor(borane)methyl)benzene with HBF$_4$.O(ME)$_2$.

Tetrafluoroboric acid dimethyl ether complex (5 equivalents, 12.5 mmols, 1.5 cm$^3$) was added slowly via syringe to a cooled (0° C.) stirred solution of 1,2 bis(di-adamantylphosphor(borane)methyl benzene (70 cm$^3$ dichloromethane). The solution was stirred at 0° C. for 1 hour and then allowed to warm to ambient temperature and stir for a further 12 hours. The reaction mixture was then added to a cooled (0° C.) saturated solution (degassed) NaHCO$_3$ solution (5*excess NaHCO$_3$) and stirred vigorously for 50 minutes. The organic phase was then extracted with 2*30 cm$^3$ portions of diethyl ether, and added to the DCM extract. The organic layers were then washed with 2×30 cm$^3$ portions of degassed water and dried over MgSO$_4$. The volatiles were then removed in-vacuo.

$^{31}$P {$^{1}$H} NMR: δ 26.4 ppm (s).

H$^1$ NMR (CDCl$_3$, 298K) δ 7.54 ppm (q, Ar—H, $J_{HH}$ 3.4 Hz), 7.0 ppm (q, Ar—H, $J_{HH}$ 3.4 Hz), 3.0 ppm (d, br CH$_2$) 1.6-2.1 ppm (m, br C$_{10}$H$_{15}$).

Example 3

Preparation of 1,2 bis(di-3,5-dimethyladamantylphosphinomethyl)benzene (method 2)

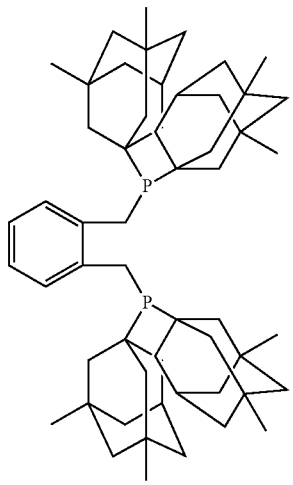

1,2-bis(di-1-(3,5-dimethyl-adamantyl) phosphinomethyl) benzene 3.1 Di-1-(3,5-dimethyladamantyl)phosphinic chloride was prepared in accordance with the method of Example 2.1 except using 1,3 dimethyladamantane 21.7 g (0.132 mol) instead of adamantane, and $AlCl_3$ (18.5 gg, 0.14 mol). Yield 23.5 g FW: 409.08. $^{31}P$ NMR: δ: 87 ppm (s).

3.2 Di-1-(3,5-dimethyladamantyl)phosphine was prepared as per Example 2.2 above except using 25.0 g Di-1-(3,5-dimethyladamantyl)phosphinic chloride instead of di-1-adamantyl phosphonic chloride Yield 15.7 g FW: 358.58. $^{31}P$ NMR: δ: 15.7 ppm (s).

3.3 Di-1-(3,5-dimethyladamantyl)phosphine}trihydroboron was prepared as per Example 2.3 above except using 10.0 g Di-1-(3,5-dimethyladamantyl)phosphine instead of di-1-adamantyl phosphine. Yield 9.5 g $^{31}P$ NMR: δ: 40.5 ppm (br).

3.4 Synthesis of 1,2 bis(di-3,5-dimethyladamantyl(borane)methyl)benzene via deprotonation with $^{sec}BuLi$ and reaction with αα dichloro o-xylene was prepared as per Example 2.4 above except using equimolar amounts of di-3,5-dimethyl adamantyl phosphine trihydroboron instead of di-1-adamantyl phosphine trihydroboron.

3.5 Synthesis of 1,2 bis(di-3,5-dimethyladamantylphosphinomethyl)benzene via deprotection of 1,2 bis(di-3,5-dimethyladamantyl phosphor(borane)methyl)benzene with $HBF_4.O(ME)_2$ was prepared as per 1,2 bis(di-1-adamantylphosphinomethyl)benzene (Example 2.5) above except by using equimolar amounts of 1,2 bis(di-3,5-dimethyadamantylphosphor(borane)methyl)benzene instead of 1,2 bis(di-adamantylphosphor(borane)methyl)benzene.

Example 4

Preparation of 1,2 bis(di-5-tert-butyladamantylphosphinomethyl)benzene (method 2)

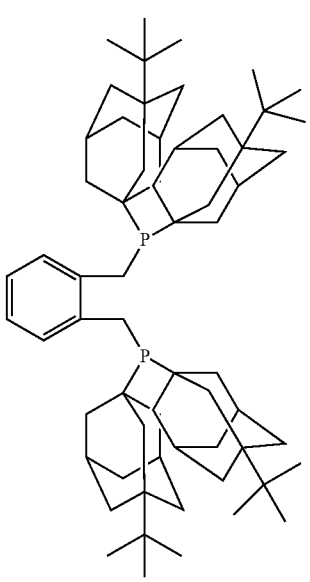

1,2-bis(di-1-(5-tert-butyl-adamantyl) phosphinomethyl) benzene 4.1 Di-1-(5-tert-butyladamantyl)phosphinic chloride was prepared as per Di-1-adamantyl phosphinic chloride above except using tert-butyladamantane 25.37 g (0.132 mol) instead of adamantane, and $AlCl_3$ (18.5 gg, 0.14 mol). Yield 22.6 g FW: 464.98. $^{31}P$ NMR: δ: 87 ppm (s).

4.2.1 Di-1-(5-tert-butyladamantyl)phosphine was prepared as per Di-1-adamantyl phosphine above except using 13.5 g Di-1-(5-tert-butyladamantyl)phosphinic chloride instead of di-1-adamantyl phosphinic chloride. Yield 9.4 g FW: 414.48. $^{31}P$ NMR: δ: 18.62 ppm (s).

4.2.2 Di-1-(5-tert-butyladamantyl)phosphine)trihydroboron was prepared as per Di-1-adamantyl phosphine above except using 10.0 g Di-1-(5-tert-butyladamantyl)phosphine instead of di-1-adamantyl phosphine. Yield 9.5 g $^{31}P$ NMR: δ: 41.6 ppm (br).

4.2.3 Synthesis of 1,2 bis(di-5-tert-butyladamantylphosphor(borane)methyl)benzene via deprotonation with $^{sec}BuLi$ and reaction with αα dichloro o-xylene was prepared as per 1,2 bis(di-1-adamantylphosphor(borane)methyl)benzene above except using equimolar amounts of di-1-(5-tert-butyladamantyl)phosphine trihydroboron instead of di-1-adamantyl phosphine trihydroboron.

4.3 Synthesis of 1,2 bis(di-5-tert-butyladamantylphosphinomethyl)benzene via deprotection of 1,2 bis(di-4-tert-butyladamantyl phosphor(borane)methyl)benzene with $HBF_4.O(ME)_2$ was prepared as per 1,2 bis(di-1-adamantylphosphinomethyl)benzene above except 1,2 bis(di-5-tertbutyladamantylphosphor(borane)methyl)benzene was used instead of 1,2 bis(di-adamantylphosphor(borane)methyl) benzene in equimolar amounts.

Example 5

Preparation of 1,2 bis(1-adamantyl tert-butyl-phosphinomethyl)benzene (method 2)

5.1. 1-adamantylphosphonic acid dichloride. This compound was synthesised according to the method of Olah et al (J. Org. Chem. 1990, 55, 1224-1227).

5.2 1-adamantyl phosphine. LiAlH$_4$ (3.5 g, 74 mmol) was added over 2 hrs to a cooled solution (0° C.) of 1-adamantylphosphonic acid dichloride (15 g, 59 mmol) in THF (250 cm$^3$). The reaction was then allowed to warm to ambient temperature and was stirred for 20 hrs. The grey suspension was then cooled (0° C.) and HCl (75 cm$^3$, 1M) was slowly added via syringe, to afford a two phase system with some solid present in the lower phase. Concentrated HCl (8 cm$^3$, 11M) was then added to improve the separation of the two layers. The (upper) THF phase was removed via cannula and dried over magnesium sulphate. After filtration via cannula, the volatiles were removed in-vacuo to afford the product.

5.3 (1-adamantyl-tert-butyl phosphine)trihydro boron. nBuLi (20 cm$^3$, 32 mmol 1.6M soln) was added over 1 hour to a cooled solution of 1-adamantyl phosphine (5.0 g 3.0 mmol) in THF (100 cm$^3$). The solution was allowed to warm to room temperature and stirred for a further 2 hours. The solution was recooled to 0° C. and tert-butylchloride (2.78 g, 30 mmol) was added and stirring continued for a further 16 hours at room temperature. The material was isolated as the borane adduct by addition of Borane (THF) adduct (30 cm$^3$, 30 mmol) followed by removal of the solvent. The material was isolated as a white solid which was a mixture of isomers.

5.4 Synthesis of 1,2 bis(1-adamantyl-tert-butyl phosphor (borane)methyl)benzene via deprotonation with $^{sec}$BuLi and reaction with αα dichloro o-xylene. The synthesis was carried out as per 1,2 bis(di-1-adamantylphosphor(borane) methyl)benzene above except equimolar amounts of 1-adamantyl-tert-butyl(phosphine)trihydroboron were used instead of the di-1-adamantyl phosphine trihydroboron.

5.5 Synthesis of 1,2 bis(1-adamantyl-tert-butylphosphinomethyl)benzene via deprotection of 1,2 bis(1-adamantyl-tert-butyl phosphor(borane)methyl)benzene with HBF$_4$.O (ME)$_2$. As per 1,2 bis(di-adamantylphosphorinomethyl) benzene except using equimolar amounts of 1,2 bis(1-adamantyl-tert-butyl phosphor(borane)methyl)benzene instead of 1,2 bis) (di-adamantylphosphor(borane)methyl) benzene.

Example 6

Preparation of 1,2 bis(di-1-diamantanephosphinomethyl) benzene. Diamantane=congressane

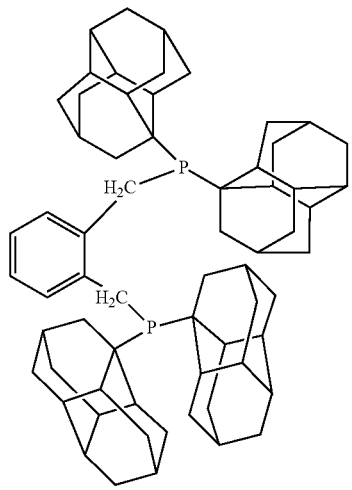

1,2 bis(dicongressylphosphinomethyl) benzene 6.1 Diamantane. This was synthesised according to the method of Tamara et al. Organic Syntheses, CV 6, 378

6.2 Di-1-(diamantane)phosphinic chloride. Prepared as per Di-1-adamantyl phosphinic chloride except using diamantane 20.0 g (0.106 mol) and AlCl$_3$ (16.0 g, 0.12 mol). Yield 25.5 g FW: 456.5. $^{31}$P NMR: δ: 87 ppm (s).

6.3 Di-1-(diamantane)phosphine. Prepared as per Di-1-adamantyl phosphine except using 25.0 g Di-1-(diamantane) phosphinic chloride. Yield 14.0 g FW: 406. $^{31}$P NMR: δ: 16.5 ppm (s).

6.4 Di-1-(diamantane)phosphine}trihydro boron. Prepared as per Di-1-adamantyl phosphine trihydro boron except using 15.0 g Di-1-(diamantane)phosphine. Yield 14.5 g. $^{31}$P NMR: δ: 42.1 ppm (br).

6.5 Synthesis of 1,2 bis(diamantane phosphor(borane) methyl)benzene via deprotonation with $^{sec}$BuLi and reaction with αα dichloro o-xylene. Prepared as per 1,2 bis(di-1-adamantylphosphor(borane)methyl)benzene except using an equimolar amount of diamantane phosphine trihydroboron instead of di-1-adamantyl phosphine trihydroboron.

6.6 Synthesis of 1,2 bis(diamantanephosphinomethyl) benzene via deprotection of 1,2 bis(diamantane(borane) methyl)benzene with HBF$_4$.O(ME)$_2$. Prepared as per 1,2 bis(di-1-adamantylphosphino methyl)benzene except using an equimolar amount of 1,2 bis diamantine phosphor(borane)methyl)benzene instead of 1,2 bis(di-adamantylphosphor(borane)methyl)benzene.

Example 7

Preparation of 1,2-bis-(ditertbutylphosphinomethyl)benzene

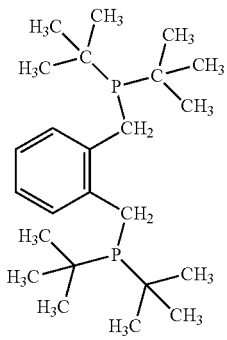

1,2-bis-(di-tert-butylphosphinomethyl)benzene

The preparation of this ligand was carried out in the manner disclosed in WO 99/47528 in accordance with Example 18.

Example 8 (Comparative)

Preparation of 1,3 bis(diadamantylphosphino)propane

Preparation of 1,3-bis-(di-1-adamantylphosphino)propane (2)

8.1 Preparation of (1-Ad)$_2$PLi

Bu"Li (2.5 M in hexanes, 42.02 cm$^3$, 105.1 mmol) was added dropwise via syringe to a stirred solution of Ad$_2$PH (10.59 g, 35.0 mmol) in THF (150 cm$^3$). This resulted in a darkening of the solution to yellow and the precipitation of a large quantity of yellow solid, in a mildly exothermic reaction. The reaction was stirred at ambient temperature for 3 h. The volatiles were removed in-vacuo, affording a very pale orange solid. The solid was washed with pentane (2×50 cm$^3$) to remove excess Bu"Li, resulting in the isolation of a white powder (washings orange) which was dried in-vacuo. The yield for this step was assumed to be quantitative, on the basis of previous NMR experiments.

8.2 Reaction of 1,3-dibromopropane with 2 equiv (1-Ad)$_2$PLi 1,3-dibromopropane (degassed, 1.78 cm$^3$, 17.5 mmol) was added dropwise via syringe to a stirred suspension of Ad$_2$PLi (35.0 mmol, prepared as above) in THF (150 cm$^3$). Initially a yellow solution was formed, then a great deal of white solid crashed out (product). The volatiles were removed in-vacuo and dichloromethane (300 cm$^3$) added via cannula affording a turbid solution. The turbidity was lost on addition of water (degassed, 100 cm$^3$), a two phase system being formed. The lower phase was removed via cannula filtration. The volatiles were removed in-vacuo, affording a white powder, which was washed with pentane (100 cm$^3$), dried and isolated in the glovebox. Yield 6.45 g, 57%. $^{31}$P NMR: δ=24 ppm, 95+% pure. FW=644.94.

Example 9

Preparation of 1,2-bis-(dimethylaminomethyl)ferrocene n-Butyllithium (Aldrich, 2.5 molar in hexane, 24 ml, 54 mmol) is added to a solution of (dimethylaminomethyl) ferrocene (Aldrich, 13.13 g, 10.69 ml, 48.97 mmol) in diethyl ether (80 ml) under nitrogen at a temperature of 25° C. and the reaction mixture stirred for 4 hours. The resulting red solution is then cooled to approximately −70° C. in a dry ice/acetone bath and Eschenmosers salt (ICH$_2$NMe$_2$) (Aldrich, 10 g, 54 mmol) is added. The reaction is allowed to warm to room temperature and stirred overnight.

The resultant solution is quenched with excess aqueous sodium hydroxide and the resulting product extracted with diethyl ether (3×80 ml) dried over anhydrous magnesium sulfate, filtered over celite, and volatiles removed in vacuo to yield the crude title compound as a light orange crystalline solid. The crude product is recrystallised from light petrol with cooling to −17° C. and the recrystallised product washed with cold petrol to yield the title compound as a light orange solid (13.2 g, 74%). The compound can be further purified by sublimation to give 8.5 g (52%) of the title compound (mpt 74° C.).

$^1$H NMR (250 MHz; CDCl$_3$): δ4.23 (brd, 2H); 4.11-4.10 (t, 1H); 4.04 (s, 5H); 3.43, 3.38, 3.23, 3.18 (AB quartet, 2H); 2.22 (s, 6H).

$^{13}$C NMR (63 MHz; CDCl$_3$): δ83.81; 70.40; 69.25; 66.84; 57.35; 45.23.

Elemental analysis: Found: C, 63.7%; H, 8.9%; N, 9.5%. Calculated: C, 64.0%; H, 8.1%; N, 9.4%.

Example 10

Preparation of 1,2-bis-(ditertbutylphosphinomethyl)ferrocene

Di-tertbutylphosphine (Aldrich, 0.616 ml, 3.33 mmol) was added to a solution of 1,2-bis(dimethylaminomethyl) ferrocene (Example 9, 0.5 g, 1.66 mmol) in anhydrous acetic acid (100 ml) under nitrogen and the resulting mixture is stirred at 80° C. for 72 hours. The anhydrous acetic acid is removed in vacuo at approximately 70° C. to yield the crude title product as an orange/yellow solid. The crude product is recrystallised from ethanol with cooling to −17° C., filtered and the filtrate washed with cold ethanol to yield the title compound as a pale yellow solid (0.365 g, 44%, 84° C.).

$^1$H NMR (250 MHz; CDCl$_3$): δ4.4 (2H, d, J=2 Hz); 3.95 (5H, S); 3.75 (1H, t, 2 Hz); 2.8 (2H, dd, 12 Hz, 2 Hz); 2.6 (2H, dd, 12 Hz, 2 Hz); 1.1 (36H, m).

$^{13}$C NMR (63 MHz; CDCl$_3$): δ86.73 (d, 5.46 Hz); 70.08 (d, 4.41 Hz); 69.4665 (s); 63.75 (s); 31.80 (d, 2 Hz); 31.45 (d, 1.98 Hz); 29.89 (d, 1.88 Hz).

$^{31}$P NMR (101 MHz; CDCl$_3$): δ15.00 ppm.

Elemental analysis: Found: C, 66.79%; H, 9.57%. Calculated: C, 66.93%; H, 9.63%.

Example 11

Preparation of 1-hydroxymethyl-2-dimethylaminomethyl ferrocene n-Butyl lithium (Aldrich, 1.6 molar in diethyl ether, 5.14 ml, 8.24 mmol) is added to a solution of 1-dimethylaminomethyl ferrocene (Aldrich, 1.0 g, 4.12 mmol) in diethyl ether (20 mL) under argon. The reaction is stirred for 3 hours and develops a reddish colour. The solution is then cooled in a dry ice/acetone bath, calcined para-formaldehyde (0.247 g, 2 times excess) added and the resultant mixture stirred overnight at room temperature.

The reaction is then quenched with water, extracted with diethyl ether, dried over MgSO$_4$, and filtered over celite. The solvent is removed in vacuo to yield crude title compound. The crude product is applied to a neutral alumina column, which is eluted with petrol/diethyl ether (9:1 ratio) to remove the starting material, 1-dimethylaminomethyl ferrocene. The column is then eluted with substantially pure ethyl acetate to elute the title compound. The ethyl acetate is removed in vacuo, to yield the title compound as an orange oil/crystalline mass.

$^1$H NMR (250 MHz; CDCl$_3$) δ2.131 (s, 6H), δ2.735 (d, 1H, 12.512 Hz), δ3.853 (d, 1H, 12.512 Hz), δ3.984 (dd, 1H, 2.156 Hz), δ4.035 (s, 5H), δ4.060 (dd, 1H, 2.136 Hz) δ4.071 (d, 1H, 12.207 Hz), δ4.154 (m, 1H), δ4.73 (d, 1H, 12.207 Hz).

$^{13}$C NMR (61 MHz; CDCl$_3$) δ7.688, δ84.519, δ70.615, δ68.871, δ68.447, δ865.369, δ60.077, δ58.318, δ44.414

COSY 2D $^1$H NMR

Partly obscured doublet at 4.071 ppm and its coupling to the doublet at 4.73 ppm confirmed.

Infrared spectra (CHCl$_3$) (c.a. 0.06 g/0.8 mL)

2953.8 cm$^{-1}$, 2860.6 cm$^{-1}$, 2826.0 cm$^{-1}$, 2783.4 cm$^{-1}$, 1104.9 cm$^{-1}$

Example 12

Preparation of 1,2-bis-(ditertbutylphosphinomethyl)ferrocene

Di-tertbutylphosphine (Aldrich, 0.54 ml, 2.93 mmol) is added to a solution of 1-hydroxymethyl-2-dimethylaminomethyl ferrocene (Example 11, 0.2 g, 0.753 mmol) in anhydrous acetic acid (15 ml) and acetic anhydride (0.753 mmol) under argon and the resulting mixture is stirred at 80° C. for 72 hours. The anhydrous acetic acid is removed in vacuo at approximately 70° C. to yield the crude title product as an orange/yellow solid. The crude product is recrystallised from ethanol with cooling to −17° C., filtered and the filtrate washed with cold ethanol to yield the title compound as an orange solid (0.23 g)

$^1$H NMR (250 MHz; CDCl$_3$) δ4.351 (d, 2H, 2 Hz), δ4.022 (s, 5H), δ3.827 (t, 1H, 2 Hz), δ2.858 (ddd, 2H, J$_{HH}$ 15.869 Hz, J$_{HP1}$ 3.320 Hz, J$_{HP2}$ 1.831 Hz), δ2.679 (dd, 2H, J$_{HH}$ 15.869 Hz, J$_{HP}$ 2.441 Hz), δ1.166 (d, 18H, 12.817 Hz), δ1.123 (d, 18H, 12.512 Hz)

FTIR (Chloroform, NaCl plates)

1104.1 cm$^{-1}$, 2863 cm$^{-1}$, 2896.0 cm$^{-1}$, 2940.0 cm$^{-1}$, 2951.8 cm$^{-1}$ $^{31}$P NMR (101 MHz; CDCl$_3$): δ15.00 ppm.

Elemental analysis: Found: C, 66.5%; H, 9.6%.

Calculated: C, 66.9%; H, 9.6%.

Example 13

Preparation of 1-hydroxymethyl-2,3-bis-(dimethylaminomethyl)ferrocene

To a stirred solution of 1,2-bis-(dimethylaminomethyl)ferrocene (Example 9, 0.70 g, 2.32 mmol) in diethyl ether (15 cm$^3$) under argon is added 1.2 equivalents n-butyl lithium (Aldrich, 1.75 mL, 1.6M in diethyl ether) and the mixture stirred for three hours to yield a red solution. The reaction mixture is cooled in a dry ice/acetone bath, calcined paraformaldehyde added in 2:1 excess, and the resultant mixture stirred at room temperature overnight. The mixture is quenched with water and extracted with diethyl ether. The ethereal extracts are dried over MgSO$_4$, filtered over celite and the solvent removed in vacuo, to yield the title compound (0.7 g, 2.12 mmol, 91%) as an orange oil., which partially crystallized on cooling.

$^1$H NMR (250 MHz; CDCl$_3$) δ 2.133 (s, 6H), δ 2.171 (s, 6H), δ 2.910 (d, 1H, 12.817 Hz), δ 2.998 (d, 1H, 12.512 Hz), δ 3.425 (d, 1H, 12.817 Hz), δ 3.812 (d, 1H, 12.512 Hz), δ 3.962 (s, 5H), δ 3.99 (d, 1H, 12.207 Hz) (partly obscured by large cp-ring peak at δ 3.962), δ 4.068 (d, 1H, δ2.136 Hz), δ 4.125) d, 1H, δ 2.136 Hz), δ 4.747 (d, 1H, 12.207 Hz)

$^{13}$C NMR (60 MHz; CDCl$_3$) δ44.529, δ45.244, δ55.798, δ57.906, δ60.271, δ67.944, δ68.277, δ69.612, δ84.850, δ88.322

Infrared spectra (CDCl$_3$/thin film NaCl plates)

3380.6 cm$^{-1}$ (br), 2955.7 cm$^{-1}$ (m), 2862.6 cm$^{-1}$, 2825.9 cm$^{-1}$ (m), 2774.3 cm$^{-1}$ (m), 1353.5 cm$^{-1}$ (m), 1104.9 cm$^{-1}$ (m), 1038.9 cm$^{-1}$ (m), 1006.8 cm$^{-1}$ (s)

Elemental analysis: Found: C, 62.3%; H, 7.8%; N, 8.8%.

Calculated: C, 61.8%; H, 7.9%; N, 8.5%.

Example 14

Preparation of 1,2,3-tris-(ditertbutylphosphinomethyl)ferrocene

Di-tert-butylphosphine (Aldrich, 2.60 mL, 13.98 mmol) and acetic anhydride (0.24 mL, 2.33 mmol) is added to a solution of 1-hydroxymethyl-2,3-bis-(dimethylaminomethyl)ferrocene (Example 13, 0.70 g, 2.12 mmol) in acetic acid (freshly distilled from acetic anhydride 25 cm$^3$), under argon. The solution is then stirred at 80° C. for 7 days, during which time the solution becomes a dark orange colour. The solvent is then removed in vacuo and recrystallisation effected from refluxing ethanol together with cooling to −17° C. overnight to yield the title compound (0.43 g, 0.7 mmol, 31%) as a yellow/orange powder.

$^1$H NMR (250 MHz, CDCl$_3$) δ 1.12 (dd-pseudo triplet, 36H, 12.1 Hz), δ1.26 (d, 18H, 10.7 Hz), δ2.68 (d, 2H, 17.7 Hz), δ2.95 (s, 2H), δ3.07, (m, 2H), δ4.01 (s, 5H) δ 4.33 (s, 2H)

Infrared spectra (CHCl$_3$/thin film NaCl plates)

1365.5 cm$^{-1}$, 1470.3 cm$^{-1}$, 2357.1 cm$^{-1}$, 2862.8 cm$^{-1}$, 2896.7 cm$^{-1}$, 2939.1 cm$^{-1}$

Example 15

Preparation of 1,2-bis-(dicyclohexylphosphinomethyl) ferrocene

The title compound was prepared in accordance with the procedure of Example 10 employing dicyclohexylphosphine (Strem of 48 High Street Orwell, Royston, United Kingdom SG8 5 QW, 659 mg, 3.33 mmol), 1,2-bis(dimethylaminomethyl)ferrocene (0.5 g, 1.66 mmol) and anhydrous acetic acid (100 ml). Yield 0.421 g.

Example 16

Preparation of 1,2-bis-(di-iso-butylphosphinomethyl)ferrocene

The title compound was prepared in accordance with the procedure of Example 10 employing di-iso-butylphosphine (Strem 486 mg, 3.33 mmol), 1,2-bis(dimethylaminomethyl) ferrocene (0.5 g, 1.66 mmol) and anhydrous acetic acid (100 ml). Yield 0.372 g.

Example 17

Preparation of 1,2-bis-(dicyclopentylphosphinomethyl) ferrocene

The title compound was prepared in accordance with the procedure of Example 10 employing dicyclopentylphosphine (Strem 566 mg, 3.33 mmol), 1,2-bis(dimethylaminomethyl)ferrocene (0.5 g, 1.66 mmol) and anhydrous acetic acid (100 ml). Yield 0.432 g.

Example 18

Preparation of 1,2-bis-(diethylphosphinomethyl)ferrocene

The title compound was prepared in accordance with the procedure of Example 10 employing diethylphosphine (Strem 299 mg, 3.33 mmol), 1,2-bis(dimethylaminomethyl)ferrocene (0.5 g, 1.66 mmol) and anhydrous acetic acid (100 ml). Yield 0.254 g.

Example 19

Preparation of 1,2-bis(di-isopropylphosphinomethyl)ferrocene

The title compound was prepared in accordance with the procedure of Example 10 employing di-iso-propylphosphine (Digital Speciality Chemicals 392 mg, 3.33 mmol), 1,2-bis(dimethylaminomethyl)ferrocene (0.5 g, 1.66 mmol) and anhydrous acetic acid (100 ml). Yield 0.262 g.

Example 20

Preparation of 1,2-bis-(dimethylphosphinomethyl)ferrocene

The title compound was prepared in accordance with the procedure of Example 10 employing dimethylphosphine (Digital Speciality Chemicals, 206 mg, 3.33 mmol), 1,2-bis(dimethylaminomethyl)ferrocene (0.5 g, 1.66 mmol) and anhydrous acetic acid (100 ml). Yield 0.285 g.

Example 21

Preparation of 1,2-bis-(diadamantylphosphinomethyl)ferrocene-bis-methanesulphonate Di-adamantylphosphine (prepared according to J. R. Goerlich, R. Schmutzler; Phosphorus Sulphur and Silicon; 1995, 102, 211-215, 20.0 g, 0.066 mol) was added to a solution of 1,2-bis(dimethylaminomethyl)ferrocene (Example 9, 10 g, 0.033 mol) in anhydrous acetic acid (100 ml) under nitrogen and the resulting mixture is stirred at 80° C. for 72 hours. The orange yellow precipitate which forms is filtered and dried in vacuo at approximately 70° C. to yield the title compound as an orange/yellow solid. The title compound is insoluble in a range of organic solvents and it is therefore purified by conversion to the bis-methanesulphonate salt by addition of excess methanesulphonic acid to a methanol slurry of the crude product. This resulted in complete dissolution of the product salt which was then isolated by removal of the methanol in vacuo followed by washing with ether and drying to give the title compound as a pale yellow solid (14.0 g, 54%).

$^1$H NMR (250 MHz; CD$_3$CN): δ4.57 (2H, d, J=2 Hz); 4.35 (5H, S); 4.27 (1H, t, 2 Hz); 3.34 (4H, br); 2.6 (6H, br); 2.35-2.18 (18H br); 2.16-2.0 (18H, br); 1.92-1.72 (24H, br).

$^{31}$P NMR (101 MHz; CD$_3$CN): δ26.58 ppm.

Elemental analysis: Found: C, 64.15%; H, 7.88%. Calculated: C, 64.29%; H, 7.94%.

Example 22

Preparation of 1,2 bis(di-1-adamantylphosphinomethyl)ferrocene-bis-methane sulphonate The preparation of this ligand was carried out as follows:
22.1 Preparation of (1-Ad)$_2$P(O)Cl
The di-1-adamantyl phosphine chloride was prepared in accordance with the method of Example 1.1.

22.2 Preparation of (1-Ad)$_2$PH
The di-1-adamantyl phosphine was prepared in accordance with the method of Example 1.2.

22.3 Preparation of 1,2-bis(di-1-adamantylphosphinomethyl)ferrocene-bis-methanesulphonate
The title compound was prepared in accordance with the procedure exemplified in Example 21.

Example 23

Preparation of 1,2-bis(di-1-(3,5-dimethyladamantyl)phosphinomethyl)ferrocene-bis-methanesulphonate 23.1 Di-1-(3,5-dimethyladamantyl)phosphinic chloride was prepared in accordance with the method of Example 3.1.

23.2 Di-1-(3,5-dimethyladamantyl)phosphine was prepared in accordance with the method of Example 3.2.

23.3 1,2-bis-(di-1-(3,5-dimethyl-adamantylphosphinomethyl) ferrocene-bis-methanesulphonate
The title compound was prepared in accordance with the procedure exemplified in Example 21 except using di-1-2 (3,5-dimethyl-adamantyl)phosphine (23.69 g, 0.066 mol) instead of di-adamantylphosphine. Yield 15 g.

Example 24

Preparation of 1,2-bis(di-1-(5-tert-butyl-adamantyl)phosphinomethyl)ferrocene-bis-methanesulphonate 24.1 Di-1-(5-tert-butyladamantyl)phosphinic chloride was prepared as per Example 4.1 above.

24.2 Di-1-(5-tert-butyladamantyl)phosphine was prepared as per Example 4.2 above.

24.3 1,2-bis(di-1-(4-tert-butyl-adamantyl)phosphinomethyl)ferrocene-bis-methanesulphonate
The title compound was prepared in accordance with the procedure exemplified in Example 21 except using di-1-(4-tert-butyladamantyl)phosphine (27.39 g, 0.066 mol) instead of di-adamantyl phosphine. Yield 14.52 g.

Example 25

Preparation of 1,2-bis-(1-adamantyl tert-butyl-phosphinomethyl)ferrocene-bis-methanesulphonate 25.1 1-adamantylphosphonic acid dichloride
This compound was synthesised according to the method of Olah et al (J. Org. Chem. 1990, 55, 1224-1227).

25.2 1-adamantyl phosphine
LiAlH$_4$ (3.5 g, 74 mmol) was added over 2 hours to a cooled solution (0° C.) of 1-adamantylphosphonic acid dichloride (15 g, 59 mmol) in THF (250 cm$^3$). The reaction was then allowed to warm to ambient temperature and was stirred for 20 hours. The grey suspension was then cooled (0° C.) and HCl (75 cm$^3$, 1M) was slowly added via syringe, to afford a two phase system with some solid present in the lower phase. Concentrated HCl (8 cm$^3$, 11M) was then added to improve the separation of the two layers. The (upper) THF phase was removed via cannula and dried over magnesium sulphate. After filtration via cannula, the volatiles were removed in-vacuo to afford the product.

25.3 1-adamantyl tert-butyl phosphine
nBuLi (20 cm$^3$, 32 mmol 1.6M soln) was added over 1 hour to a cooled solution of 1-adamantyl phosphine (5.0 g, 30 mmol) in THF (100 cm$^3$). The solution was allowed to warm to room temperature and stirred for a further 2 hours. The solution was recooled to 0° C. and tert-butylchloride (2.78 g, 30 mmol) was added and stirring continued for a further 16 hours at room temperature. The reaction mixture was quenched with water and the aqueous phase extracted with dichloromethane (2×50 ml). The organic phase was dried over sodium sulphate and evaporated in-vacuo to yield the title compound.

25.4 1,2-bis-(-1-adamantyl tert-butyl-phosphinomethyl)ferrocene-bis-methanesulphonate The title compound was prepared in accordance with the procedure exemplified in Example 21 except using 1-adamantyl tert-butyl phosphine (14.78 g, 0.066 mol) instead of di-adamantyl phosphine. Yield 9.80 g.

Example 26

Preparation of 1,2-bis-(di-1-diamantylphosphinomethyl)ferrocene-bis-methanesulphonate 26.1 Diamantane This was synthesised according to the method of Tamara et al. Organic Syntheses, CV 6, 378.

26.2 Di-1-(diamantane)phosphinic chloride

Prepared as per Di-1-adamantyl phosphinic chloride of Example 1.1 except using diamantane 20.0 g (0.106 mol) and $AlCl_3$ (16.0 g, 0.12 mol). Yield 25.5 g FW: 456.5. $^{31}P$ NMR: δ: 87 ppm (s).

26.3 Di-1-(diamantane)phosphine

Prepared as per Di-1-adamantyl phosphine of Example 1.2 except using 25.0 g Di-1-(diamantane)phosphinic chloride. Yield 14.0 g FW: 406. $^{31}P$ NMR: δ: 16.5 ppm (s).

26.4 1,2-bis-(di-1-diamantylphosphinomethyl)ferrocene-bis-methanesulphonate

The title compound was prepared in accordance with the procedure exemplified in Example 21 except using di-1-diamantane phosphine (26.79 g, 0.066 mol) instead of di-adamantyl phosphine. Yield 12.5 g.

Example 27

Preparation of 1,2-bis-(di-(1,3,5,7-tetramethyl-6,9,10-trioxa-2-phospha-adamantylmethyl))ferrocene 1,3,5,7-tetramethyl-2,4,8-trioxa-6-phospha-adamantane (obtained from Cytec, 14.0 g, 0.066 mol) was added to a solution of 1,2-bis(dimethylaminomethyl)ferrocene (Example 9, 10 g, 0.033 mol) in anhydrous acetic acid (100 ml) under nitrogen and the resulting mixture is stirred at 80° C. for 72 hours. The anhydrous acetic acid is removed in vacuo at approximately 70° C. to yield the crude title product as an orange/yellow solid. This is washed with hot methanol to give the product as a mixture of isomers as an orange solid. (12.0 g, 58%).

1H NMR (250 MHz; $CDCl_3$): δ4.25-3.95 (8H, br, m); 3.46 (4H, br); 1.57-2.0 (8H, br, m); 1.43-1.23 (24H, br m).

$^{31}P$ NMR (101 MHz; $CDCl_3$): δ −27.41 (br), −29.01 (s), −33.9 (br) ppm.

Elemental analysis: Found: C, 57.80%; H, 7.35%. Calculated: C, 57.87%; H, 7.40%.

Example 28

Preparation of 1,2-bis-(dimethylaminomethyl)ferrocene-bis methyl iodide

Methyl iodide (23.28 g, 0.164 mol) is added to a solution of 1,2-bis-(dimethylaminomethyl)ferrocence (Example 9, 20 g, 0.082 mol) in degassed methanol (100 ml), and the mixture stirred at room temperature under a nitrogen atmosphere for 24 hours. The resulting precipitate is removed by filtration, washed with ether and dried to yield the title compound (43.0 g).

Elemental analysis: Found: C, 36.8%; H, 5.1%; N, 4.8%. Calculated: C, 37.0%; H, 5.2%; N, 4.8%.

$^{13}C$ NMR ($D_2O$): δ53.27, δ53.21, δ53.15, δ64.68, δ71.77, δ73.24, δ74.13, δ74.95

Example 29

Preparation of 1,2-bis(dihydroxymethylphosphinomethyl)ferrocene

Potassium hydroxide (8.52 g, 0.152 mol) is added to a solution of tetrakis(hydroxymethyl)phosphonium chloride (Aldrich, 38.54 g of 80% w/w aqueous solution, 0.162 mol) in degassed methanol (40 ml), and stirred at room temperature under a nitrogen atmosphere for 1 hour. The resultant mixture is added dropwise to a degassed solution of 1,2-bis-(dimethylaminomethyl)ferrocene-bis-methyl iodide (Example 28, 19.98 g, 52.2 mmol) in methanol (40 ml) under nitrogen at room temperature with stirring. The resultant mixture is refluxed under nitrogen for 20 hours, and the solvent removed in vacuo to form a red precipitate. Water (30 ml), diethyl ether (85 ml) and triethylamine (35 ml) is added to the precipitate and the solution stirred at room temperature for 1 hour. The aqueous layer is removed and re-extracted with diethyl ether (2×30 ml). The combined ethereal extracts are washed with water (3×20 ml) dried over sodium sulphate and filtered. The ether is removed in vacuo to yield the crude title compound (14.33 g, 94% yield) as a microcrystalline orange solid. The crude product is recrystallised from a warm dicholormethane/methanol solution with the addition of light petroleum and cooling to yield the title compound (10.69 g, 70% yield) as yello-orange crystals.

Elemental analysis: Found: C, 48.44%; H, 4.12%; N, 0.0%.

Calculated: C, 48.24%; H, 4.02%; N, 0.0%.

$^1H$ NMR: δ1.75 (s, br), δ2.70 (dd, 2H, $J^2_{HH}$ 14.2 Hz, $J^2_{HP}$ 6.6 Hz), δ2.85 (dd, 2H, $J^2_{HH}$ 14.2 Hz, $J^2_{HP}$ 7.9 Hz), δ3.71 (t, 1H, $J_{HH}$ 2.44 Hz), δ3.58 (s, 5H), δ3.98 (d, 2H, $J_{HH}$ 2.40 Hz), 4.06 (m, 8H).

$^1H\{^{31}P\}$ NMR: δ1.75 (s, br), δ2.70 (d, 14.3 Hz), δ2.85 (d, 14.3 Hz), δ4.04 (m, 1H), δ4.06 (s, 8H), δ4.08 (s, 5H), δ4.1 (m, 2H)

$^{13}C$ NMR: 523.7 (d, $J^1_{PC}$ 15.6 Hz), δ63.0 (d, $J^1_{PC}$ 15.6 Hz), δ66.0 (s), δ67.2 (d, $J^3_{PC}$ 9.2 Hz), δ69.6 (s), δ82.6 (d, $J^2_{PC}$ 14.7 Hz)

$^{31}P$ NMR: δ−14.7

Infrared spectra ($CHCl_3$/thin film NaCl plates)

3337.8 $cm^{-1}$ (st, br), further peaks 1104 $cm^{-1}$ 2929.0 $cm^{-1}$, 3603.7 $cm^{-1}$, 3683.7 $cm^{-1}$.

Example 30

Preparation of 1,2-bis(diphosphinomethyl)ferrocene 1,2-bis(dihydroxymethylphosphinomethyl)ferrocene (Example 29, 5.45 g, 13.70 mmol) and sodium metabisulfite (5.21 g, 27.4 mmol) is added to a two-phase solvent system consisting of distilled water (60 ml) and light petroleum (60 ml). The mixture is refluxed for 3 hours in air. The resultant mixture is cooled stirred and the aqueous layer removed. The organic layer is washed with distilled water and the organic solvent removed in vacuo to yield the title compound (2.66 g, 70% yield) as an orange crystalline solid.

Elemental analysis: Found: C, 51.65%; H, 5.75%.

Calculated: C, 51.80%; H, 5.76%.

$^1H$ NMR (250 MHz; $CDCl_3$): δ 2.7-2.8 (m, 4H), δ 3.17 (m, 2H), δ 3.18 (m, 2H), δ 4.04 (t, 1H, J=2.54 Hz), δ 4.09 (d, 5H, $J_{HP}$ 0.4 Hz), δ 4.13 (d, 2H, J=2.54 Hz)

$^{31}$P NMR (101 MHz; CDCl$_3$): δ130.0 (t, J$_{HP}$ 193.0 Hz)
$^{13}$C NMR (60 MHz; CDCl$_3$): δ12.9, δ 65.6, δ 67.3, δ 69.4, δ 86.9
$^{13}$C DEPT NMR (CDCl$_3$): δ 12.9 (CH$^2$), δ 65.6 (CH), δ 67.3 (CH), δ 69.40 (5×CH)
FTIR (Chloroform, NaCl plates): 2298.5 cm$^{-1}$ (strong)
Mass spectrum: Found m/z: 278.0088; Calculated m/z 278.0077

Example 31

Preparation of —(P-(2,2,6,6,-tetramethylphosphinan-4-one))dimethylferroce☐,☐1,2-bis-ne

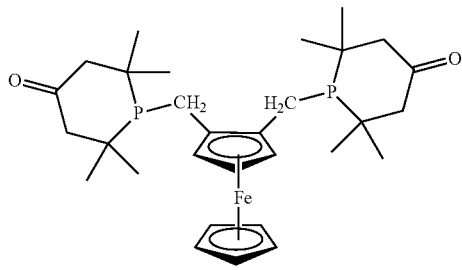

1,2-bis-,-(P-(2,2,6,6,-tetramethylphosphinan-4-one))dimethylferrocene 2,6-Dimethyl-2,5-heptadiene-4-one (14.6 g, 0.106 mol) is added to 1,2-bis-(diphosphinomethyl)ferrocene (Example 30, 14.7 g, 0.053 mol) and the mixture heated to 120° C. under nitrogen for 20 hours. The reaction mixture is cooled, the crude title compound removed by filtration, washed with pentene (20 ml) and dried in vacuo to yield the title compound as a yellow-orange solid (24.9 g, 85% yield). The title compound was characterised by $^{31}$P NMR and mass spectrum.
$^1$H NMR (250 MHz; CDCl$_3$): d 4.32 (1H, br); 4.08 (5H, br); 4.02 (1H, br); 3.94 (1H br); 2.84 (4H, br); 1.8-2.5 (8H, br); 1.05-1.4 (24H, br).
$^{31}$P NMR (101 MHz; CDCl$_3$): s 4.15 ppm.
Elemental analysis: Found: C, 64.26%; H, 7.88%.
Calculated: C, 65.03%; H, 7.94%.

Example 32

Preparation of 1,2-bis-(di-1,3,5,7-tetramethyl-6,9,10-trioxa-2-phospha-adamantylmethyl))benzene The preparation of this ligand was carried out in the manner disclosed in WO-A-03/070370 in accordance with Example 4 therein.

Example 33

Preparation of Methyl Propanoate from Ethylene, Carbon Monoxide and Methanol Catalysed by a Compound of the Present Invention Condition 1 ratio of ligand:palladium=5.2:1, ratio of acid:palladium=160:1 and ratio acid:ligand=30:1
Condition 2 ratio of ligand:palladium=5.2:1, ratio of acid:palladium=480:1 and ratio acid:ligand=90:1
A mechanically stirred autoclave (Hastelloy) of 2 liter capacity was evacuated of air and then charged with a solution of tri(dibenzylideneacetone)dipalladium (1.44× 10$^{-5}$ moles), 1,2-bis-(di-tertbutylphosphinomethyl)ferrocene of Example 10, (7.61×10$^{-5}$ moles) and methane sulfonic acid (2.30×10$^{-3}$ moles condition 1, 6.90×10$^{-3}$ moles condition 2) in 300 ml of methyl propanoate/methanol (70 wt % methyl propanoate). The autoclave was heated to 100° C. and when at that temperature, ethylene (8×10$^5$ Nm$^{-2}$) was added on top of the vapour pressure of the solvents and immediately an equimolar mixture of carbon monoxide and ethylene (2×10$^5$ Nm$^{-2}$) added to the system through a pressure regulating valve set to 10×10$^5$ Nm$^{-2}$ above the solvent vapour pressure. Suitably, the molar ratio of ethylene to carbon monoxide in the reactor is approximately 9:1. The temperature of the reactor was maintained at 100° C. and as the reaction proceeded additional carbon monoxide and ethylene was added (on an equimolar basis) through the pressure regulating Tescom valve. No catalyst precipitation was observed.

Initial reaction rates measured in moles of methyl propanoate (MeP) per mole of palladium per hour and turnover measured in moles of methyl propanoate per mole of palladium were determined for the catalyst. This may be accomplished by an analysis of the amount of gas consumed per unit time (rate) and the total amount of gas consumed during the reaction, assuming ideal gas behaviour and 100% selectivity to methyl propanoate.

Table 1 shows the effect in increasing the relative acid concentration compared to phosphine ligand concentration (and metal concentration) for a batch process on both the maximum initial rate and the turnover number (TON) after 1 hour, wherein initial reaction rates are measured in moles of methyl propanoate (MeP) per mole of palladium per hour and TON is measured as moles of methyl propanoate per mole of palladium. For both TON and maximum initial rate, values are significantly increased passing from condition 1 to condition 2, i.e. when increasing both the acid:palladium and acid:ligand ratios at constant ligand:palladium values.

TABLE 1

| | Maximum Initial Rate (moles MeP/ mole Pd/hr) | Turnover Number after 1 hour (moles MeP/mole Pd) |
|---|---|---|
| 1,2-bis-(di-tert-butylphosphinomethyl)benzene - condition 2 | 66261 | 50786 |
| 1,2-bis-(di-tert-butylphosphinomethyl)benzene - condition 1 | 42103 | 32397 |
| 1,2-bis-(di-tert-butylphosphinomethyl)benzene - condition 2 | 94957 | 62635 |
| 1,2-bis-(di-tert-butylphosphinomethyl)benzene - condition 1 | 45421 | 29465 |
| 1,2-bis-(di-(1,3,5,7-tetramethyl-6,9,10-trioxa-2-phospha-adamantylmethyl))ferrocene - condition 2 | 55799 | 51997 |
| 1,2-bis-(di-(1,3,5,7-tetramethyl-6,9,10-trioxa-2-phospha-adamantylmethyl))ferrocene - standard | 8490 | 4814 |
| -(P-(2,2,6,6,-tetramethylphosphinan-4-one))dimethylferroce☐☐☐1,2-bis-ne - condition 2 | 29839 | 24270 |
| -(P-(2,2,6,6,-tetramethylphosphinan-4-one))dimethylferroce☐☐☐1,2-bis-ne - condition 1 | 21591 | 17676 |
| 1,2-bis-(di-(1,3,5,7-tetramethyl-6,9,10-trioxa-2-phospha-adamantylmethyl))benzene - condition 2 | 29839 | 24270 |

TABLE 1-continued

| | Maximum Initial Rate (moles MeP/ mole Pd/hr) | Turnover Number after 1 hour (moles MeP/mole Pd) |
|---|---|---|
| 1,2-bis-(di-(1,3,5,7-tetramethyl-6,9,10-trioxa-2-phospha-adamantylmethyl))benzene - condition 1 | 12041 | 11444 |
| 1,2-bis-(di-(1,3,5,7-tetramethyl-6,9,10-trioxa-2-phospha-adamantylmethyl))benzene - condition 2 | 20177 | 16610 |
| 1,2-bis(di-1-adamantylphosphinomethyl)ferrocene-bis-methanesulphonate - condition 2 | 67599 | 68141 |
| 1,2-bis(di-1-adamantylphosphinomethyl)ferrocene-bis-methanesulphonate - condition 1 | 41167 | 33798 |

Example 34

Pd(OAc)$_2$ (22 mg, 0.1 mmol) and the respective phosphine ligand (0.5 mmol) were weighed out in the inert atmosphere glove box into 500 mL 3-neck round bottom flasks. On removal, 300 mL of degassed MeOH were added and the mixture stirred for 1 hour. To the solution methanesulphonic acid (640 μl, 10 mmol) was added. The weight of the catalyst solution was taken. The autoclave was charged with the solution and heated to 100 C with stirring (3.0 barg vapour pressure). The reaction was started by the introduction of CO/ethylene (1:1) gaseous mixture to the autoclave. The total pressure of the autoclave was controlled by a TESCOM (9.8 barg). This resulted in a 9:1 ratio of ethylene to CO. The temperature and pressure were maintained 3 hours during which period these values were recorded.

The gases were isolated and the unit cooled to room temperature. The depressurised unit was emptied and the final weight of the solution taken.

Ligand 1=1,2-bis(di-tert-butylphosphinomethyl)benzene
Ligand 2=1,2-bis(di-tert-butylphosphinomethyl)ferrocene
Ligand 3=1,2-bis(diadamantylphosphinomethyl)ferrocene
Ligand 4=1,2-bis(diphospha-adamantylphosphinomethyl)ferrocene
Ligand 5=1,3-bis(di-tert-butylphosphino)2-methylene-propane (comparative), prepared as in WO-A-03/040159 (Example 1 therein).

The results are shown in the tables below.

TABLE 2

| Ligand | Ratio Pd:Lig:Acid | Wt Gain (g) | Avg. Wt Gain (g) |
|---|---|---|---|
| 1 | 1:5:100 | 268.65 | 257.304 |
| 1 | 1:5:100 | 244.47 | |
| 1 | 1:5:100 | 258.98 | |
| 1 | 1:5:100 | 252.13 | |
| 1 | 1:5:100 | 262.29 | |

TABLE 3

| Ligand | Ratio Pd:Lig:Acid | Wt Gain (g) | Avg. Wt. Gain (g) |
|---|---|---|---|
| 2 | 1:5:100 | 302.64 | 300.9 |
| 2 | 1:5:100 | 306.84 | |
| 2 | 1:5:100 | 293.4 | |

TABLE 3-continued

| Ligand | Ratio Pd:Lig:Acid | Wt Gain (g) | Avg. Wt. Gain (g) |
|---|---|---|---|
| 2 | 1:5:100 | 303.09 | |
| 2 | 1:5:100 | 298.54 | |

TABLE 4

| Ligand | Ratio Pd:Lig:Acid | Wt gain (g) | Avg Wt Gain (g) |
|---|---|---|---|
| 3 | 1:5:100 | 364.97 | 347.54 |
| 3 | 1:5:100 | 340.18 | |
| 3 | 1:5:100 | 345.15 | |
| 3 | 1:5:100 | 339.88 | |

TABLE 5

| Ligand | Ratio Pd:Lig:Acid | Wt gain (g) | Avg Wt Gain (g) |
|---|---|---|---|
| 4 | 1:5:25 | 126.31 | Av 1:5:300 |
| 4 | 1:5:100 | 165.21 | 249.67 |
| 4 | 1:5:100 | 189.83 | |
| 4 | 1:5:300 | 221.61 | |
| 4 | 1:5:300 | 261.28 | |
| 4 | 1:5:300 | 281.81 | |
| 4 | 1:5:300 | 233.99 | |

TABLE 6

| Run No. | Ligand | Wt gain (g) | Ratio Pd:Lig:Acid |
|---|---|---|---|
| 1 | 5 | 33.3 | 1:5:100 |
| 2 | 5 | 83.16 | 1:1:100 |
| 3[a] | 5 | 165.1 | 1:1:4 |
| 4[a] | 5 | 235.97 | 1:1:4 |
| 5[a] | 5 | 82.53 | 1:6:4 |

[a]run at 3 × palladium concentration {67.3 mg Pd(OAc)$_2$}

For the ligand 1,3-bis(di-tert-butylphosphino)2-methylene-propane (ligand 5) additional ligand with or without excess acid results in a drop in catalyst performance. The optimum conditions of low ligand and acid, e.g. Run Nos. 3 and 4, result in the highest catalyst productivity under the conditions studied. Addition of excess ligand at high acid ratio as in Run No. 1 results in a significant drop in performance, as does addition of excess ligand at low acid ratios.

The following two tables contain data for the ligand 1,2-Bis(di-tert-butylphosphinomethyl)benzene. The data was collected at 80 C hence the rates and turnover numbers are lower than the data we have already included. However, the data shows that at constant acid:ligand[b] levels, an increase in ligand:Pd ratio provides large increases in initial rate and TON values. This data also used the preformed catalyst [(L-L)Pd(dba)] (for details see below) and adds the ligand excess as the protonated salt. The experimental detail is provided below.

TABLE 7

| Ligand | Ratio Pd:Lig:Acid | Ratio Acid:Ligand[b] | Initial rate | TON after 4 hours |
|---|---|---|---|---|
| 1 | 1:5:36 | 10.9 | 5000 | 12000 |
| 1 | 1:5:72 | 20 | 17000 | 25000 |
| 1 | 1:5:143 | 37 | 22000 | 30000 |

[b] in this ratio the "acid" includes both the acid from the protonated phosphine ligand together with the additional acid added (i.e., "free" acid) and the ligand is simply the protonated phosphine ligand.

TABLE 8

| Ligand | Ratio Pd:Lig:Acid | Ratio Acid:Ligand[b] | Initial rate | TON after 4 hours |
|---|---|---|---|---|
| 1 | 1:10:90 | 10.9 | 22000 | 42000 |
| 1 | 1:10:182 | 20 | 33000 | 52000 |
| 1 | 1:10:352 | 37 | 41500 | 71000 |

The number of moles of palladium is equal to the number of moles of $L_2Pd(dba)$.

The work described in these examples was carried out in 2 L capacity autoclaves. In each test 10 mg of $L_2Pd(dba)$ catalyst and 32 mg (4 equivalents) or 72 mg (9 equivalents) of protonated phosphine were added to the preparation flask in a nitrogen purged glove box. 175 mL of azeotrope product consisting of 50:50 wt % methanol and methyl propanoate and 125 mL of methyl propanoate were then degassed and added to the flask to provide a reaction solution which was close to 70 wt % methyl propanoate. After addition of the required quantity of methanesulphonic acid the solution was transferred to the evacuated autoclave and heated to 80° C. in vacuo. During this period and at all subsequent times the autoclave was stirred at ~1000 r.p.m. When this temperature had been reached the total pressure of the system was increased to 9 bar (from the vapour pressure baseline of ~1 bar) by the addition of ethylene and then topped up with 2 bar of 1:1 $C_2H_4/CO$ such that the total pressure was ~11 bar and the headspace $C_2H_4/CO$ ratio was 9:1. After this time only the 1:1 gas was fed to the system at the rate which was required to hold the pressure within the system constant. Reaction rates and catalyst TONs were calculated from the rate of removal of gas from the feed reservoir assuming ideal gas behaviour and 100% selectivity for methyl propanoate formation.

Preparation of 1,2-bis(di-1-adamantylphosphinomethyl) benzene palladium (dba)

THF (100 cm$^3$) was added to a combination of ligand (2.05 g, 2.90 mmol) and palladium dba (1.61 g, 2.90 mmol [Pd]) affording a deep red-orange turbid solution. The reaction was stirred for 3 h. The reaction was filtered via cannula, yielding a deep red-orange filtrate and a small quantity of [Pd] residue. The volatiles were removed in-vacuo affording a deep red powdery solid. Pentane (50 cm$^3$) was added via cannula and attrition performed with a spatula, resulting in an orange powder separating out. The amber pentane washings were removed via cannula filtration, and the solid washed with $Et_2O$ at −10° C. (3×50 cm$^3$). The resultant orange powder was dried in-vacuo and isolated in the glovebox. Yield 2.68 g, 88%. $^{31}$P NMR: δ=46, 42 ppm (1:1 ratio), essentially phosphorus pure. FW=1047.73.

Preparation of 1,3-bis-(di-1-adamantylphosphino)propane palladium (dba)

As above, except using ligand (1.96 g, 3.04 mmol) and palladium dba (1.69 g, 3.04 mmol [Pd]) in THF (70 cm$^3$).

After 3 h, the deep red-orange solution was fairly turbid in appearance; an additional 50 cm$^3$ THF was added to further dissolve the product. The reaction was worked-up as above, except the $Et_2O$ washing was performed at ambient temperature. The solid was isolated in the glovebox as an orange powder. Yield 2.08 g, 69%. 31P NMR: δ=42, 38 ppm (1:1 ratio, noisy). FW=985.66.

Also see "Studies on the Palladium Catalysed Methoxycarbonylation of Ethene", thesis submitted to the University of Durham by G. R. Eastham (1998), for details on the preparation of $L_2Pd(dba)$ complexes.

Example 35

Preparation of Methyl Propanoate from Ethylene, Carbon Monoxide and Methanol Catalysed by a Compound of the Present Invention The continuous process exemplified involved the reaction of purified streams of carbon monoxide, ethylene and methanol in the liquid phase, in the presence of a catalyst system, to generate the desired product, methyl propanoate.

The reaction was carried out at 100° C. and at 12 barg pressure in the reactor vessel.

The catalyst system was made up of three components, being a palladium salt, a phosphine ligand and an acid. The three catalyst components, when combined together and dissolved in the reaction mixture, constitute the reaction catalyst or catalyst system, a homogeneous catalyst, which converted dissolved reactants to the product methyl propanoate in the liquid phase.

During continuous operation, the catalyst decomposed at a slow but steady rate, and was replaced by adding fresh catalyst, or the rate of generation of the product, methyl propanoate reduces.

The reactor vessel was fitted with an agitator, and also a means of re-circulating the unreacted gas that collected in the upper headspace area of the reactor. The unreacted gas from the reactor vessel headspace, which was made up of a mixture of ethylene and carbon monoxide, was returned continuously to the reactor via an entry pipe at the base, such that the gas passed up through the reaction mixture continuously.

Upon entering into the reactor vessel the gas was dispersed by the agitator into fine bubbles. In this way the ethylene and carbon monoxide were dissolved in the reaction mix.

Fresh ethylene and carbon monoxide gases were added to the re-circulating gas to make up for the amount of the two gases that have been used up by the reaction. Fresh methanol was also added continuously to the reactor vessel, in order to replace the methanol that has been used up in the reaction.

The reactor vessel held the bulk liquid reaction mixture, along with the three components of the homogeneous catalyst, being a palladium salt, a phosphine ligand, and a sulphonic acid.

In order to recover the product methyl propanoate, a stream of reaction mixture was passed continuously out of the reactor and into the distillation column.

The distillation column, being a single stage 'flash' type distillation column, provided a means of separating a fraction of the methyl propanoate and methanol components of the reaction mixture from the non-volatile dissolved catalyst components. This was achieved by vaporising a fraction of the reaction mixture as it passed through the flash column. The part of the reaction mixture which remained as liquid after passing through the flash column, and which still contained useful catalyst components, was returned to the reactor vessel so that the catalyst components could take part in the on-going reaction.

If the methyl propanoate product was required free of methanol, a second distillation column was required. In this case, the vapour stream from the flash column, which is a mixture of methyl propanoate and methanol was passed into the second distillation column, where the pure methyl propanoate was generated as the heavier product, and taken off from the base of the column. A low boiling mixture of methanol and methyl propanoate was generated as the light product, and was removed continuously from the top of the MeP purification column. In order to utilise the methanol as efficiently as possible in the process, the low boiling mixture of methanol and methyl propanoate was returned continuously to the reactor vessel.

After start up of the continuous reactor unit, when the desired rate of generation of methyl propanoate had been achieved, a process of gradual reduction of the feed rates of the catalyst components was undertaken.

In order to sustain the rate of generation of methyl propanoate it was necessary to continuously replace the palladium catalyst component which was lost to decomposition with fresh palladium at a rate which balanced the rate of loss.

This led to the situation where the standing concentrations of catalyst components became constant for a given rate of generation of methyl propanoate, and just able to sustain flow sheet reaction rate, as indicated by constant concentrations of carbon monoxide and ethylene in the headspace area of the reactor vessel. This was called the balance point, because under these conditions the rate of palladium decomposition was balanced exactly by the rate of addition of fresh palladium.

From the rate of addition of fresh palladium catalyst component under balance point conditions, the palladium turnover number (TON) was calculated. This is defined as the number of mol of methyl propanoate generated per hour, for each mol of palladium consumed by the decomposition process per hour.

Upon reaching a steady rate at a pre-determined set of control conditions, the instantaneous values of all of the variables were recorded, and used as representative data to show the performance of the process under the conditions in use at the time.

To gather data on the effect of levels of phosphine ligand and acid present in the reaction mixture on palladium turnover number, all variables were held constant except the background levels of ligand and acid in the reaction mixture. These levels were changed by making small additions of these compounds to the reaction vessel via a dedicated tank and pumping system. The additions were then followed by careful adjustment of the catalyst solution feed rate to re-establish the balance position.

The experimental design was such that after collecting each new set of balance point data, the system was returned to a previous set of conditions to check for any drifting of performance before moving on to the next set of experimental conditions.

In this way, comparative sets of results were drawn up which showed clearly the changes to catalyst stability that were caused by the variations in the background levels of phosphine ligand and acid levels.

The amount of palladium in the feed to the reactor is critical to calculation of turnover number results. Assurance on the rate of fresh catalyst being fed to the system was provided by analysis of each batch of catalyst prior to transfer to the catalyst feed tanks for palladium content. Further assurance was gained by determination of the actual feed rate of catalyst from timing of the fall in the level in a burette, which is part of the catalyst feed system.

Table 9 shows the effect on palladium turnover number (TON) when increasing the acid:ligand ratio and the ligand:metal ratio.

In this Example, the acid used was methanesulphonic acid, the bidentate phosphine ligand was 1,2-bis-(ditertbutylphosphinomethyl)benzene, and the palladium compound was tri(dibenzylideneacetone)dipalladium.

TABLE 9

| ligand:Pd mol ratio | acid:ligand mol ratio | Free acid in reactor (ppm) | Turnover Number (moles MeP/moles Pd) |
|---|---|---|---|
| 6.29 | 9.93 | 676 | $2.02 \times 10^6$ |
| 10.33 | 13.38 | 988 | $3.30 \times 10^6$ |
| 13.49 | 21.73 | 1682 | $3.41 \times 10^6$ |
| 17.16 | 34.65 | 2834 | $3.42 \times 10^6$ |
| 17.16 | 7.40 | 837 | $5.00 \times 10^6$ |

Figure 2:
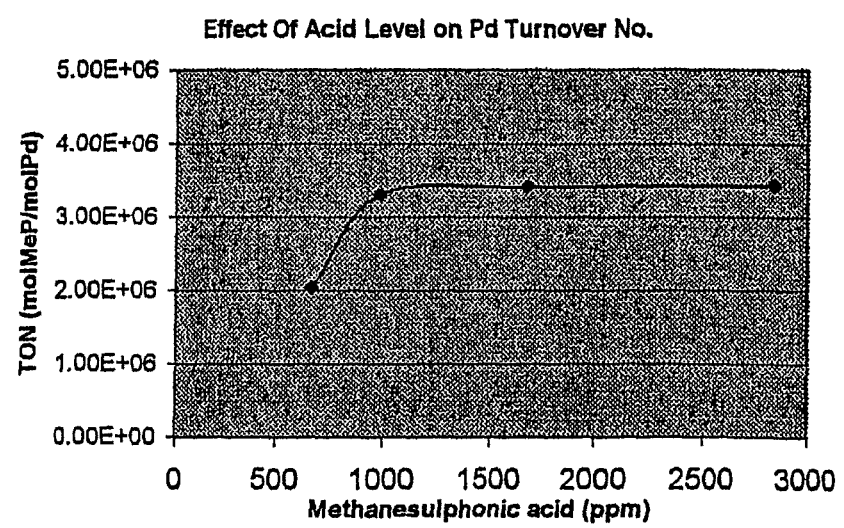
FIG. 2 shows TON versus amount of methanesulphonic acid present free in the reactor.
Figure 3:
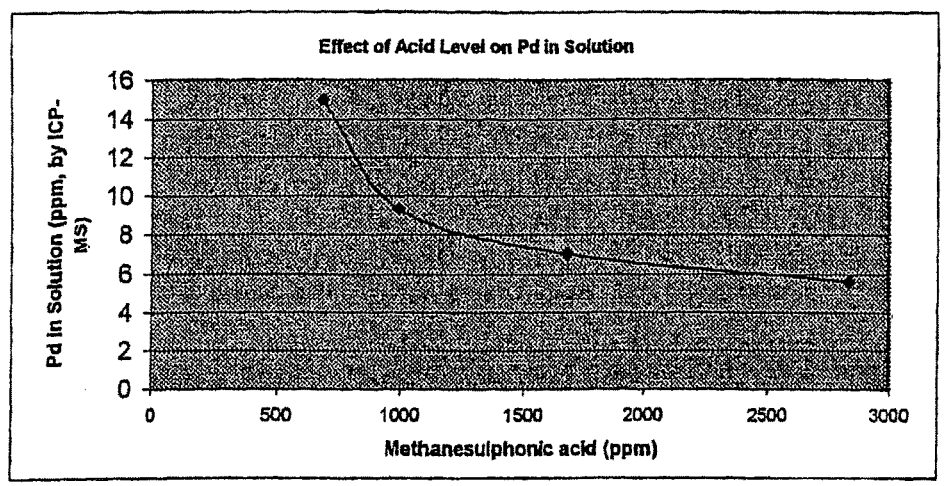
FIG. 3 shows Pd amount in solution versus amount of methanesulphonic acid.

Further trends are seen in FIG. 1-3 of the accompanying figures.

FIG. 1 shows TON versus acid:ligand mol ratio. Clearly, as the acid:ligand ratio increases above about 10, there is a large increase in TON for this particular catalyst system.

FIG. 2 shows TON versus amount of methanesulphonic acid present free in the reactor. Clearly, as the level of acid increases, there is a large increase in TON for this particular catalyst system.

FIG. 3 shows Pd amount in solution versus amount of methanesulphonic acid. Clearly, as the level of acid increases, there is a decrease in the amount of Pd in solution for this particular catalyst system, whilst the reaction rate remains constant. Therefore, working at these elevated acid levels, reaction rates can be maintained even as the palladium levels decrease. The advantages in view of the relative cost of the palladium component of the catalyst system is clear.

Although some preferred embodiments have been shown and described, it will be appreciated by those skilled in the art that various changes and modifications might be made without departing from the scope of the present invention, as defined in the appended claims.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the carbonylation of an ethylenically unsaturated compound comprising contacting ethene with carbon monoxide and a hydroxyl group containing compound in the presence of a catalyst system, which system is obtained by combining:
   a) palladium or a compound thereof,
   b) a bidentate phosphine, arsine, or stibine ligand, and
   c) an acid,
   wherein said ligand is present in at least a 2:1 molar excess compared to said palladium metal or said palladium metal in said metal compound, and said acid is present in at least a 2:1 molar excess compared to said ligand.

2. A process as claimed in claim 1 wherein the ratio of said ligand to said metal is in the range 5:1 to 750:1.

3. A process as claimed in claim 1 wherein the ratio of said ligand to said metal is in the range 10:1 to 500:1.

4. A process as claimed in claim 1 wherein the ratio of said ligand to said metal is in the range 20:1 to 40:1.

5. A process as claimed in claim 1 wherein the ratio of said acid to said ligand is in the range 20:1 to 40:1.

6. A process as claimed in claim 1 wherein the molar ratio of said acid to said metal is in the range 10:1 to 75000:1.

7. A process as claimed in claim 1 wherein the molar ratio of said acid to said metal is in the range 100:1 to 25000:1.

8. A process as claimed in claim 1 wherein the molar ratio of said acid to said metal is in the range 200:1 to 400:1.

9. A process as claimed in claim 1 wherein said ligand is a bidentate phosphine ligand.

10. A process as claimed in claim 1 wherein said ligand is of general formula (I)

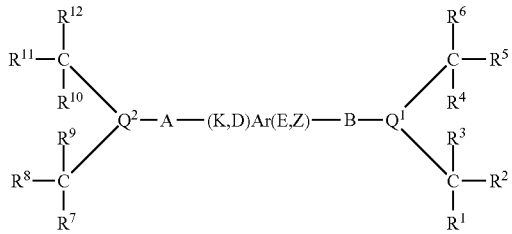

wherein:
Ar is a bridging group comprising an optionally substituted aryl moiety to which the phosphorus atoms are linked on available adjacent carbon atoms;
A and B each independently is lower alkylene;
K, D, E and Z are substituents of the aryl moiety (Ar) and each independently is hydrogen, lower alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$, $C(O)SR^{27}$, or $-J-Q^3(CR^{13}(R^{14})(R^{15})CR^{16}(R^{17})(R^{18})$ where J is lower alkylene; or two adjacent groups selected from K, Z, D and E together with the carbon atoms of the aryl ring to which they are attached form a further phenyl ring, which is optionally substituted by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$;

$R^1$ to $R^{18}$ each independently is lower alkyl, aryl, Het or at least one $(CR^xR^yR^z)$ group attached to $Q^1$, $Q^2$ and/or $Q^3$, i.e. $CR^1R^2R^3$, $CR^4R^5R^6$, $CR^7R^8R^9$, $CR^{10}R^{11}R^{12}$, $CR^{13}R^{14}R^{15}$, or $CR^{16}R^{17}R^{18}$, is the group (Ad) wherein:
Ad each independently is an optionally substituted adamantyl or congressyl radical bonded to the phosphorus atom via any one of its tertiary carbon atoms, the said optional substitution being by one or more substituents selected from hydrogen, lower alkyl, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)R^{25}R^{26}$, $SR^{27}$ or $C(O)SR^{27}$; or if both $(CR^xR^yR^z)$ groups attached to either or both $Q^1$ and/or $Q^2$, or $Q^3$ (if present) together with either $Q^1$ or $Q^2$ (or $Q^3$) as appropriate, form an optionally substituted 2-phospha-tricyclo[3.3.1.1{3,7}]decyl group or derivative thereof, or form a ring system of formula

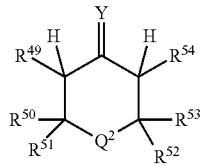

wherein
$R^{49}$ and $R^{54}$ each independently is hydrogen, lower alkyl or aryl;
$R^{50}$ to $R^{53}$, when present, each independently is hydrogen, lower alkyl, aryl or Het; and
Y is oxygen, sulfur or N—$R^{55}$; and
$R^{55}$, when present, is hydrogen, lower alkyl or aryl;
$R^{19}$ to $R^{27}$ each independently represent is hydrogen, lower alkyl, aryl or Het; and
$Q^1$, $Q^2$ and $Q^3$ (when present) each independently is phosphorus, arsenic or antimony and in the latter two cases references to phosphorus above are amended accordingly.

11. A process as claimed in claim 10 wherein $R^1$ to $R^{18}$ each independently is lower alkyl, aryl, or Het.

12. A process as claimed in claim 10 wherein said ligand is:

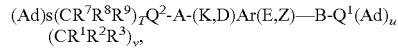

wherein K, D, E and Z is $-J-Q^3(Ad)_w(CR^{13}(R^{14})(R^{15})_x$, wherein S and U are 0, 1 or 2 provided that S+U≥1;
wherein T and V are 0, 1 or 2 provided that T+V≤3; and
wherein W and X are 0, 1 or 2.

13. A process as claimed in claim 1 wherein said ligand is of general formula (III):

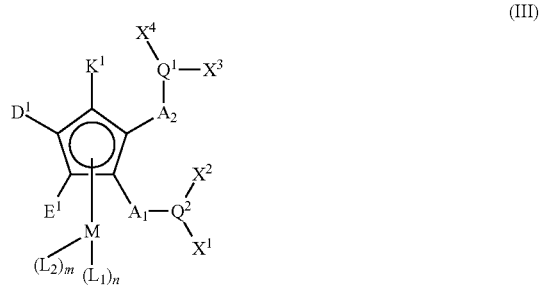

wherein:

$A_1$ and $A_2$, and $A_3$, $A_4$ and $A_5$ (when present), each independently is lower alkylene;

$K^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_3-Q^3(X^5)X^6$;

$D^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $-A_4-Q^4(X^7)X^8$;

$E^1$ is selected from the group consisting of hydrogen, lower alkyl, aryl, Het, halo, cyano, nitro, $-OR^{19}$, $-OC(O)R^{20}$, $-C(O)R^{21}$, $-C(O)OR^{22}$, $-N(R^{23})R^{24}$, $-C(O)N(R^{25})R^{26}$, $-C(S)(R^{27})R^{28}$, $-SR^{29}$, $-C(O)SR^{30}$, $-CF_3$ or $A_5-Q^5(X^9)X_{10}$;

or both $D^1$ and $E^1$ together with the carbon atoms of the cyclopentadienyl ring to which they are attached form an optionally substituted phenyl ring:

$X^1$ is $CR^1(R^2)(R^3)$, congressyl or adamantyl, $X^2$ is $CR^4(R^5)(R^6)$, congressyl or adamantyl, or $X^1$ and $X^2$ together with $Q^2$ to which they are attached form an optionally substituted 2-phospha-tricyclo[3.3.1.1{3,7}]decyl group or derivative thereof, or $X^1$ and $X^2$ together with $Q^2$ to which they are attached form a ring system of formula IIIa

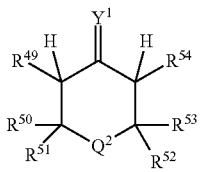

(IIIa)

$X^3$ is $CR^7(R^8)(R^9)$, congressyl or adamantyl, $X^4$ is $CR^{10}(R^{11})(R^{12})$, congressyl or adamantyl, or $X^3$ and $X^4$ together with $Q^1$ to which they are attached form an optionally substituted 2-phospha-tricyclo[3.3.1.1{3,7}]decyl group or derivative thereof, or $X^3$ and $X^4$ together with $Q^1$ to which they are attached form a ring system of formula IIIb

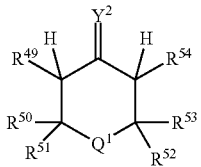

(IIIb)

$X^5$ is $CR^{13}(R^{14})(R^{15})$, congressyl or adamantyl, $X^6$ is $CR^{16}(R^{17})(R^{18})$, congressyl or adamantyl, or $X^5$ and $X^6$ together with $Q^3$ to which they are attached form an optionally substituted 2-phospha-tricyclo[3.3.1.1{3,7}]decyl group or derivative thereof, or $X^5$ and $X^6$ together with $Q^3$ to which they are attached form a ring system of formula IIIc

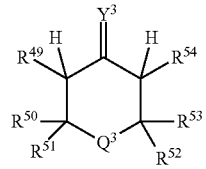

(IIIc)

$X^7$ is $CR^{31}(R^{32})(R^{33})$, congressyl or adamantyl, $X^8$ is $CR^{34}(R^{35})(R^{36})$, congressyl or adamantyl, or $X^7$ and $X^8$ together with $Q^4$ to which they are attached form an optionally substituted 2-phospha-tricyclo[3.3.1.1{3,7}]decyl group or derivative thereof, or $X^7$ and $X^8$ together with $Q^4$ to which they are attached form a ring system of formula IIId

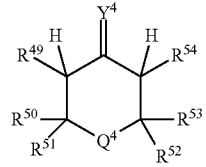

(IIId)

$X^9$ is $CR^{37}(R^{38})(R^{39})$, congressyl or adamantyl, $X^{10}$ is $CR^{40}(R^{41})(R^{42})$, congressyl or adamantyl, or $X^9$ and $X^{10}$ together with $Q^5$ to which they are attached form an optionally substituted 2-phospha-tricyclo[3.3.1.1.{3,7}]decyl group or derivative thereof, or $X^9$ and $X^{10}$ together with $Q^5$ to which they are attached form a ring system of formula IIIe

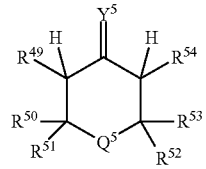

(IIIe)

$Q^1$ and $Q^2$, and $Q^3$, $Q^4$ and $Q^5$ (when present), each independently is phosphorus, arsenic or antimony;

M is a Group VIB or VIIIB metal or metal cation thereof;

$L_1$ is an optionally substituted cyclopentadienyl, indenyl or aryl group;

$L_2$ is one or more ligands each of which are independently selected from hydrogen, lower alkyl, alkylaryl, halo, CO, $P(R^{43})(R^{44})R^{45}$ or $N(R^{46})(R^{47})R^{48}$;

$R^1$ to $R^{18}$ and $R^{31}$ to $R^{42}$, when present, each independently is hydrogen, lower alkyl, aryl, halo or Het;

$R^{19}$ to $R^{30}$ and $R^{43}$ to $R^{48}$, when present, each independently is hydrogen, lower alkyl, aryl or Het;

$R^{49}$, $R^{54}$ and $R^{55}$, when present, each independently is hydrogen, lower alkyl or aryl;

$R^{50}$ to $R^{53}$, when present, each independently is hydrogen, lower alkyl, aryl or Het; $Y^1$, $Y^2$, $Y^3$, $Y^4$ and $Y^5$, when present, each independently is oxygen, sulfur or $N-R^{55}$;

n=0 or 1;

and m=0 to 5;

provided that when n=1 then m equals 0, and when n equals 0 then m does not equal 0.

14. A process as claimed in claim 13 wherein if both $K^1$ is $-A_3-Q^3(X^5)X^6$ and $E^1$ is $A_5-Q^5(X^9)X^{10}$, then $D^1$ is $-A_4-Q^4(X^7)X^8$.

15. A process as claimed in claim 10 or 13, wherein adamantyl is unsubstituted adamantyl or adamantyl substituted with one or more unsubstituted $C_1$-$C_8$ alkyl substituents, or a combination thereof.

16. A process as claimed in claim 10 or 13, wherein 2-phospha-adamantyl is unsubstituted 2-phospha-adamantyl or 2-phospha-adamantyl substituted with one or more unsubstituted $C_1$-$C_8$ alkyl substituents, or a combination thereof.

17. A process as claimed in claim 10 or 13, wherein 2-phospha-adamantyl includes one or more oxygen atoms in the 2-phospha-adamantyl skeleton.

18. A process as claimed in claim 10 or 13, wherein congressyl is unsubstituted congressyl.

19. A process according to claim 1 wherein the palladium is in the metal form.

20. A process according to claim 1, wherein the catalyst system includes in a liquid reaction medium a polymeric dispersant dissolved in a liquid carrier, said polymeric dispersant being capable of stabilising a colloidal suspension of particles of the Group VI or VIIIB metal or metal compound of the catalyst system within the liquid carrier.

21. A process according to claim 1, wherein the carbonylation of ethene is performed in one or more aprotic solvents.

22. A process according to claim 10, wherein $Q^1$, $Q^2$ and $Q^3$ (when present) is phosphorus.

\* \* \* \* \*